United States Patent
Schnute et al.

(10) Patent No.: US 10,336,748 B2
(45) Date of Patent: Jul. 2, 2019

(54) METHYOXY-SUBSTITUTED PYRROLOPYRIDINE MODULATORS OF RORC2 AND METHODS OF USE THEREOF

(71) Applicant: Pfizer Inc., New York, NY (US)

(72) Inventors: Mark Edward Schnute, Acton, MA (US); Andrew Christopher Flick, East Lyme, CT (US); Peter Jones, Arlington, MA (US); Neelu Kaila, Lexington, MA (US); Scot Richard Mente, Arlington, MA (US); John David Trzupek, Medford, MA (US); Michael L. Vazquez, Billerica, MA (US); Goran Mattias Wennerstal, Hagersten (SE); Li Xing, Lexington, MA (US); Edouard Zamaratski, Uppsala (SE); Liying Zhang, Lexington, MA (US); Rayomand J. Unwalla, Bedford, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/546,887

(22) PCT Filed: Jan. 29, 2016

(86) PCT No.: PCT/IB2016/050473
§ 371 (c)(1),
(2) Date: Jul. 27, 2017

(87) PCT Pub. No.: WO2016/120849
PCT Pub. Date: Aug. 4, 2016

(65) Prior Publication Data
US 2018/0002330 A1    Jan. 4, 2018

Related U.S. Application Data

(60) Provisional application No. 62/110,138, filed on Jan. 30, 2015.

(51) Int. Cl.
*C07D 471/04* (2006.01)

(52) U.S. Cl.
CPC ................ *C07D 471/04* (2013.01)

(58) Field of Classification Search
CPC .................................. C07D 471/04
See application file for complete search history.

(56) References Cited

U.S. PATENT DOCUMENTS

| | | | |
|---|---|---|---|
| 4,742,057 A | 5/1988 | Ueda et al. | |
| 5,962,473 A | 10/1999 | Johnson | |
| 6,391,891 B1 | 5/2002 | Gaster et al. | |
| 7,842,692 B2 * | 11/2010 | Kugimiya ............ | C07D 471/04 514/234.5 |
| 2016/0046597 A1 | 2/2016 | Schnute et al. | |
| 2016/0090381 A1 | 3/2016 | Schnute et al. | |

FOREIGN PATENT DOCUMENTS

| | | | |
|---|---|---|---|
| WO | 99/64044 A1 | 12/1999 | |
| WO | 2005/095400 | 10/2005 | |
| WO | WO-2007010965 A1 * | 1/2007 | ........... C07D 471/04 |
| WO | 2014/086894 | 6/2014 | |
| WO | WO-2015015378 A2 * | 2/2015 | ........... C07D 401/14 |
| WO | 16/120850 A1 | 8/2016 | |

OTHER PUBLICATIONS

Lopez-Rodriguez et al, "AThree-Dimensional Pharmacophore Model 5-Hydroxytryptamine-6 (5-HT6) Receptor Antagonists," Journal of Medicinal Chemistry 48(13):4216-4219 (2005).

* cited by examiner

*Primary Examiner* — David K O'Dell
(74) *Attorney, Agent, or Firm* — James T. Wasicak

(57) ABSTRACT

The present invention provides methoxy-substituted pyrrolopyridines, pharmaceutical compositions thereof, methods of modulating RORγ activity and/or reducing the amount of IL-17 in a subject, and methods of treating various medical disorders using such pyrrolopyridines and pharmaceutical compositions thereof.

11 Claims, No Drawings
Specification includes a Sequence Listing.

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

METHYOXY-SUBSTITUTED PYRROLOPYRIDINE MODULATORS OF RORC2 AND METHODS OF USE THEREOF

BACKGROUND OF THE INVENTION

Retinoid-related orphan receptors (ROR) are reported to have an important role in numerous biological processes. Scientific investigations relating to each of retinoid-related orphan receptors RORα, RORβ, and RORγ have been described in the literature. Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. Two isoforms of RORγ have been identified and are referred to as γ1 and γ2 (also referred to as RORγt). Expression of the γ2 isoform has been reported to appear in, for example, double-positive thymocytes. Compounds capable of modulating RORγt activity are contemplated to provide a therapeutic benefit in the treatment of multiple medical disorders, including immune and inflammatory disorders.

Numerous immune and inflammatory disorders continue to afflict millions of patients worldwide. Significant advances have been made in treating these disorders. However, current therapies do not provide satisfactory results for all patients due to, for example, detrimental side effects or insufficient efficacy. Treatments for immune and inflammatory disorders vary depending on the particular medical disorder, and often involve use of immunosuppressive drugs. Surgery (e.g., splenectomy), plasmapheresis, or radiation can be used in certain instances.

One exemplary immune disorder in need of better therapy is psoriasis. Psoriasis is a T cell-mediated inflammatory disease that affects approximately 2% to 3% of adults and has a substantial adverse impact on the quality of life for patients suffering from this disorder. Plaques resulting from psoriasis can be painful and are visually unappealing. Various therapeutics have been developed in an attempt to treat psoriasis. However, the traditional therapies for psoriasis often have toxic adverse effects. Accordingly, a need exists for improved treatments for psoriasis as well as other immune and inflammatory disorders.

SUMMARY

The present invention provides compounds, pharmaceutical compositions, methods of inhibiting RORγ activity and/or reducing the amount of IL-17 in a subject, and methods of treating various medical disorders using such compounds. In particular, one aspect of the invention relates to compounds represented by Formula I:

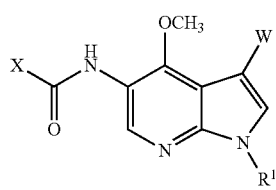

I and pharmaceutically acceptable salts, pharmaceutically active metabolites, pharmaceutically acceptable prodrugs, and pharmaceutically acceptable solvates thereof; wherein $R^1$, X and W are as defined in the Detailed Description.

Another aspect of the invention provides a method of treating a subject suffering from a medical disorder. The method comprises administering to the subject a therapeutically effective amount of a compound of Formula I or a pharmaceutically acceptable salt or solvate thereof, as described in the Detailed Description. A large number of disorders may be treated using the compounds described herein. For example, the compounds described herein may be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein.

DETAILED DESCRIPTION

The invention provides compounds, pharmaceutical compositions, methods of modulating RORγ activity and/or reducing the amount of IL-17 in a subject, and therapeutic uses of said compounds and pharmaceutical compositions. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein.

Chemical names, common names, and chemical structures may be used interchangeably to describe the same structure. If a chemical compound is referred to using both a chemical structure and a chemical name, and an ambiguity exists between the structure and the name, the structure predominates.

Definitions

"ROR" stands for Retinoic acid receptor-related Orphan Receptor. There are three forms of ROR, ROR-α, -β, and -γ and each is encoded by a separate gene (RORA, RORB, and RORC respectively). There are two subtypes of RORC: 1 and 2. Subtype 2 is also called "t". The human RORC gene is also called TOR; RORG; RZRG; NRIF3; and RZR-GAMMA. The human protein RORC is also called nuclear receptor ROR-gamma; nuclear receptor RZR-gamma; retinoic acid-binding receptor gamma; retinoid-related orphan receptor gamma; RAR-related orphan receptor C, isoform a; RAR-related orphan nuclear receptor variant 2; nuclear receptor subfamily 1 group F member 3. As used herein, "RORγ" and "RORC2" are used interchangeably to refer to a protein from a RORC subtype 2 gene.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "alkyl" refers to a substituent obtained by removing a hydrogen from a saturated, straight (i.e. unbranched) or branched carbon chain (or carbon), or combination thereof, which has the number of carbon atoms designated (i.e. $C_1$-$C_6$ means one to six carbons). Examples of alkyl substituents include methyl, ethyl, propyl (including n-propyl and isopropyl), butyl (including n-butyl, isobutyl, sec-butyl and tert-butyl), pentyl, isoamyl, hexyl and the like.

The term "haloalkyl" is an alkyl in which at least one hydrogen on the alkyl is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "cycloalkyl" refers to a substituent obtained by removing a hydrogen atom from a saturated carbocycle having the number of carbon atoms designated (i.e. $C_3$-$C_8$ means three to eight carbons). Cycloalkyl refers to both a radical of a single ring saturated carbocycle, such as cyclopropyl, cyclobutyl, cyclopentyl and cyclohexyl. as well as a radical of a two or three ring bridged, fused or spiro saturated carbocycle, such as bicyclo[4.2.0]octane and decalinyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described such that it "may be substituted" or as being "optionally substituted" with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

As used herein compounds of Formula I may be referred to as a "compound(s) of the invention." Such terms are also defined to include all forms of the Formula I including hydrates, solvates, isomers, crystalline and non-crystalline forms, isomorphs, polymorphs, and metabolites thereof. For example, the compounds of Formula I and pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

In some embodiments, compounds described herein could be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

The compounds of the invention may have asymmetric carbon atoms. The carbon-carbon bonds of the compounds of the invention may be depicted herein using a solid line, a solid wedge or a dotted wedge. The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Stereoisomers of compounds of the invention include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes isotopically-labeled compounds, which are identical to those recited in Formula I herein, but for the fact that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of Formula (I), for example those into which radioactive isotopes such as $^{3}H$ and $^{14}O$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds the invention may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Compounds

In the following description of compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

In certain embodiments, the compounds of the invention described herein are selective for RORγ over RORα and/or RORβ.

Generally, an inhibitor compound of RORγ used in the methods described herein is identified or characterized in an in vitro assay, e.g., an acellular biochemical assay or a cellular functional assay. Such assays are useful to determine an in vitro $IC_{50}$ for said compounds. In some embodiments, the RORγ inhibitor compound used for the methods described herein inhibits RORγ activity with an in vitro $IC_{50}$ of less than 25 μM (e.g., less than 20 μM, less than 10 μM, less than 1 μM, less than 0.5 μM, less than 0.4 μM, less than 0.3 μM, less than 0.1, less than 0.08 μM, less than 0.06 μM, less than 0.05 μM, less than 0.04 μM, less than 0.03 μM, less than less than 0.02 μM, less than 0.01, less than 0.008 μM, less than 0.006 μM, less than 0.005 μM, less than 0.004 μM, less than 0.003 μM, less than less than 0.002 μM, less than 0.001, less than 0.00099 μM, less than 0.00098 μM, less than 0.00097 μM, less than 0.00096 μM, less than 0.00095 μM, less than 0.00094 μM, less than 0.00093 μM, less than 0.00092, or less than 0.00090 μM). In some embodiments, the RORγ inhibitor compound is a compound described in the Exemplification.

Described herein are compounds of Formula I. Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by Formula I are also provided.

One aspect of the invention relates to a compound of Formula I:

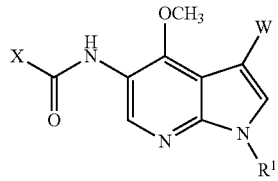

I or a pharmaceutically acceptable salt, pharmaceutically active metabolite, pharmaceutically acceptable prodrug, or pharmaceutically acceptable solvate thereof, wherein, X is phenyl optionally substituted with one, two, three, four or five substituents independently selected from the group consisting of —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN;

$R^1$ is —$CH_3$ or —$CH_2CH_3$;

W is

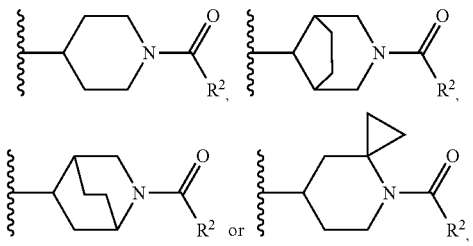

each optionally substituted with one, two, three, four or five —$CH_3$; and $R^2$ is ($C_1$-$C_6$)alkyl, ($C_3$-$C_{10}$)cycloalkyl, phenyl, tetrahydrothiophenyl, thietanyl or indanyl, optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_8$)cycloalkyl.

In certain embodiments, the present invention relates to any of the aforementioned compounds, wherein $R^1$ is —$CH_3$.

In certain embodiments, the present invention relates to any of the aforementioned compounds, wherein $R^1$ is —$CH_2CH_3$.

In certain embodiments, the present invention relates to any of the aforementioned compounds, wherein W is

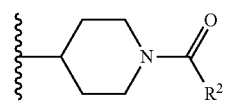

optionally substituted with one, two, three, four or five —$CH_3$.

In certain embodiments, the present invention relates to any of the aforementioned compounds, wherein W is

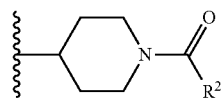

optionally substituted with one, two, three, four or five —$CH_3$; and $R^1$ is —$CH_3$.

In certain embodiments, the present invention relates to any of the aforementioned compounds, wherein W is

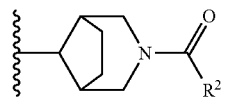

optionally substituted with one, two, three, four or five —$CH_3$.

In certain embodiments, the present invention relates to any of the aforementioned compounds, wherein W is

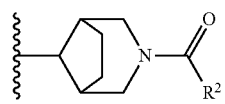

optionally substituted with one, two, three, four or five —$CH_3$; and $R^1$ is —$CH_3$.

In certain embodiments, the present invention relates to any of the aforementioned compounds, wherein W is

optionally substituted with one, two, three, four or five —$CH_3$.

In certain embodiments, the present invention relates to any of the aforementioned compounds, wherein W is

optionally substituted with one, two, three, four or five —$CH_3$; and $R^1$ is —$CH_3$.

In certain embodiments, the present invention relates to any of the aforementioned compounds, wherein W is

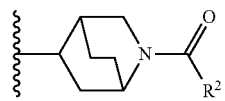

optionally substituted with one, two, three, four or five —$CH_3$.

In certain embodiments the present invention relates to any of the aforementioned compounds, wherein W is

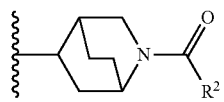

optionally substituted with one, two, three, four or five —CH$_3$; and R$^1$ is —CH$_3$.

In certain embodiments, the present invention relates to any of the aforementioned compounds, wherein W is

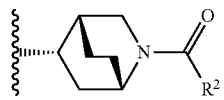

optionally substituted with one, two, three, four or five —CH$_3$.

In certain embodiments, the present invention relates to any of the aforementioned compounds, wherein W is

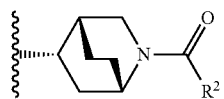

optionally substituted with one, two, three, four or five —CH$_3$; and R$^1$ is —CH$_3$.

In certain embodiments, the present invention relates to any of the aforementioned compounds, wherein W is

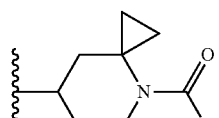

optionally substituted with one, two, three, four or five —CH$_3$.

In certain embodiments, the present invention relates to any of the aforementioned compounds, wherein W is

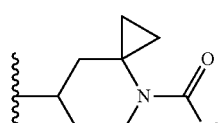

optionally substituted with one, two, three, four or five —CH$_3$; and R$^1$ is —CH$_3$.

In certain embodiments, the present invention relates to any of the aforementioned compounds, wherein W is

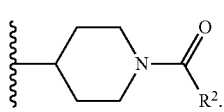

In certain embodiments, the present invention relates to any of the aforementioned compounds, wherein W is

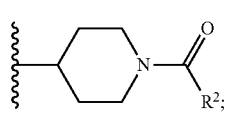

and R$^1$ is —CH$_3$.

In certain embodiments, the present invention relates to any of the aforementioned compounds, wherein W is

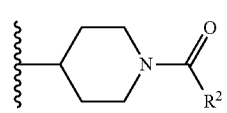

substituted with one —CH$_3$.

In certain embodiments, the present invention relates to any of the aforementioned compounds, wherein W is

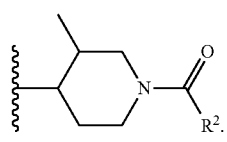

In certain embodiments, the present invention relates to any of the aforementioned compounds, wherein W is

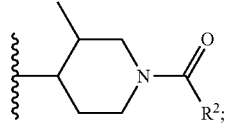

and R$^1$ is —CH$_3$.

In certain embodiments, the present invention relates to any of the aforementioned compounds, wherein W is

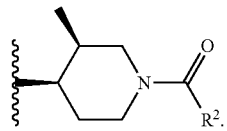

In certain embodiments, the present invention relates to any of the aforementioned compounds, wherein W is

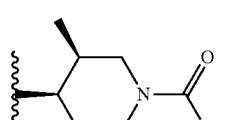

and R$^1$ is —CH$_3$.

In certain embodiments, the present invention relates to any of the aforementioned compounds, wherein W is

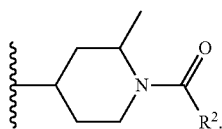

In certain embodiments, the present invention relates to any of the aforementioned compounds, wherein W is

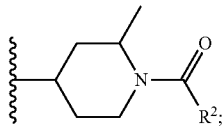

and $R^1$ is —$CH_3$.

In certain embodiments, the present invention relates to any of the aforementioned compounds, wherein W is

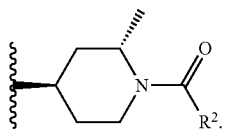

In certain embodiments, the present invention relates to any of the aforementioned compounds, wherein W is

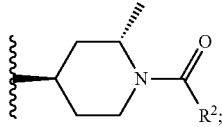

and $R^1$ is —$CH_3$.

In certain embodiments, the present invention relates to any of the aforementioned compounds, wherein W is

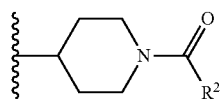

substituted with two —$CH_3$.

In certain embodiments, the present invention relates to any of the aforementioned compounds, wherein W is

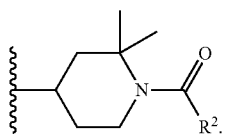

In certain embodiments, the present invention relates to any of the aforementioned compounds, wherein W is

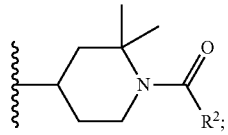

and $R^1$ is —$CH_3$.

In certain embodiments, the present invention relates to any of the aforementioned compounds, wherein W is

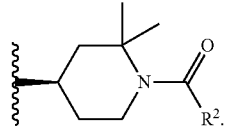

In certain embodiments, invention relates to any of the aforementioned compounds, wherein W is

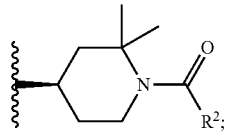

and $R^1$ is —$CH_3$.

In certain embodiments, the present invention relates to any of the aforementioned compounds, wherein X is unsubstituted phenyl.

In certain embodiments, the present invention relates to any of the aforementioned compounds, wherein X is phenyl substituted with one, two, three, four or five substituents independently selected from the group consisting of —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN.

In certain embodiments, the present invention relates to any of the aforementioned compounds, wherein X is phenyl substituted with one substituent selected from the group consisting of with —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN.

In certain embodiments, the present invention relates to any of the aforementioned compounds, wherein X is phenyl substituted with two substituents independently selected from the group consisting of —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN.

In certain embodiments, the present invention relates to any of the aforementioned compounds, wherein X is phenyl substituted with three substituents independently selected from the group consisting of —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN.

In certain embodiments, the present invention relates to any of the aforementioned compounds, wherein X is phenyl substituted with four substituents independently selected from the group consisting of —$CH_3$, —$CH_2CH_3$, —OH, —$OCH_3$, —$SCH_3$, —$OCH_2CH_3$, —$OCH_2CH_2OH$, —$OCH_2CH_2OCH_3$, —F, —Cl, —Br and —CN.

In certain embodiments, the present invention relates to any of the aforementioned compounds, wherein X is phenyl substituted with five substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with —CN and optionally substituted with one or two substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with —Cl and optionally substituted with one or two substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

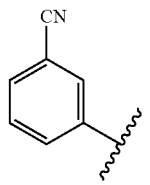 [SMILES: *c1cccc(Cl)c1]

optionally substituted with one additional substituent selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

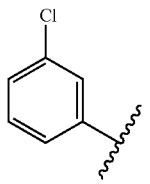

substituted with one additional substituent selected from the group consisting of —CH₃, —CH₂CH₂, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

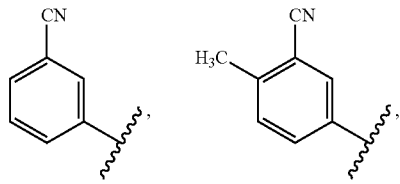

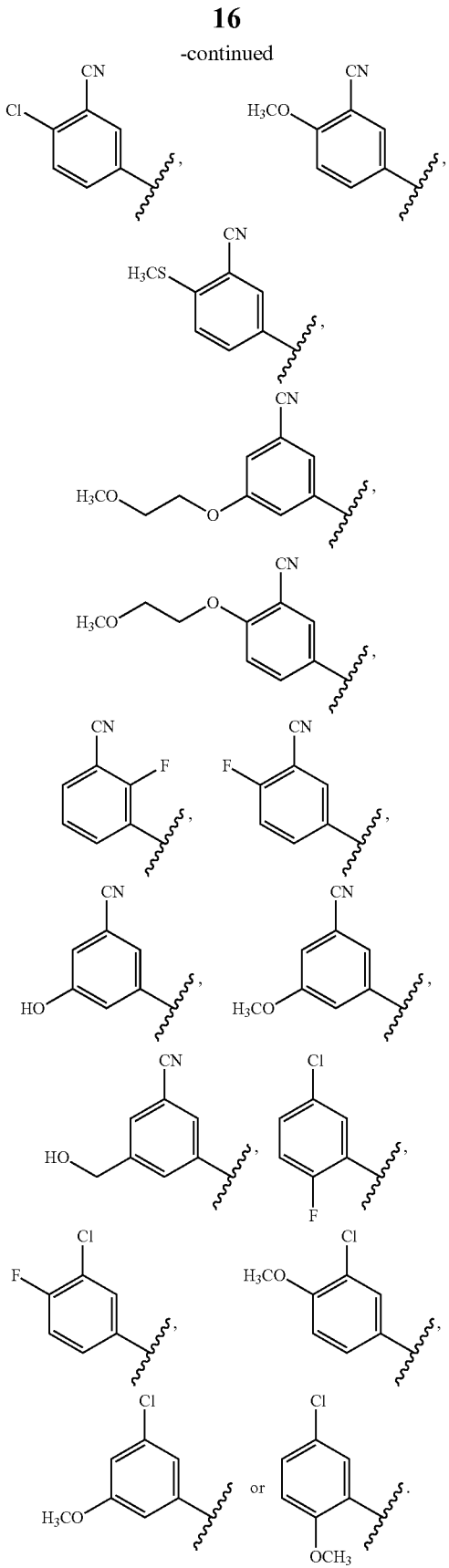

In certain embodiments, the present invention relates to any of the aforementioned compounds, wherein X is

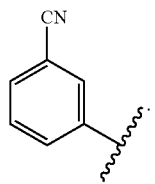 [SMILES: *c1cccc(C#N)c1]

In certain embodiments, the present invention relates to any of the aforementioned compounds, wherein X is

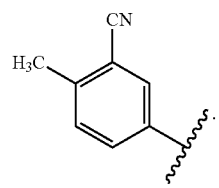

In certain embodiments, the present invention relates to any of the aforementioned compounds, wherein X is

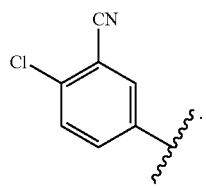 [SMILES: *c1ccc(Cl)c(C#N)c1]

In certain embodiments, the present invention relates to any of the aforementioned compounds, wherein X is

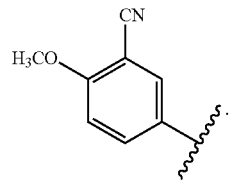

In certain embodiments, the present invention relates to any of the aforementioned compounds, wherein X is

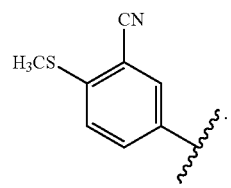

In certain embodiments, the present invention relates to any of the aforementioned compounds, wherein X is

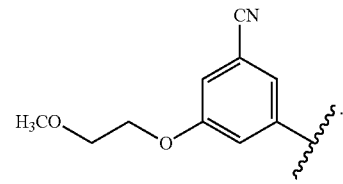

In certain embodiments, the present invention relates to any of the aforementioned compounds, wherein X is

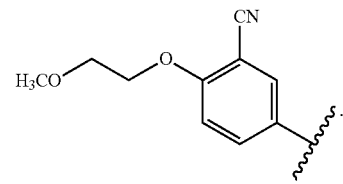 [SMILES: *c1ccc(OCCOC)c(C#N)c1]

In certain embodiments, the present invention relates to any of the aforementioned compounds, wherein X is

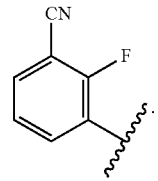 [SMILES: *c1cccc(C#N)c1F]

In certain embodiments, the present invention relates to any of the aforementioned compounds, wherein X is

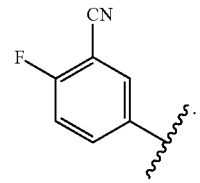

In certain embodiments, the present invention relates to any of the aforementioned compounds, wherein X is

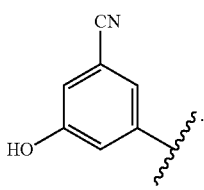 [SMILES: *c1cc(O)cc(C#N)c1]

In certain embodiments, the present invention relates to any of the aforementioned compounds, wherein X is

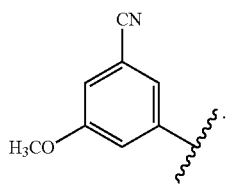

In certain embodiments, the present invention relates to any of the aforementioned compounds, wherein X is

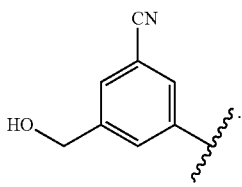

In certain embodiments, the present invention relates to any of the aforementioned compounds, wherein X is

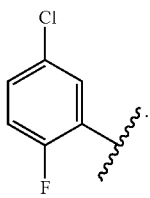 [SMILES: *c1cc(Cl)ccc1F]

In certain embodiments, the present invention relates to any of the aforementioned compounds, wherein X is

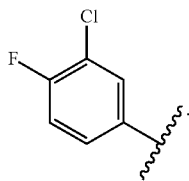

In certain embodiments, the present invention relates to any of the aforementioned compounds, wherein X is

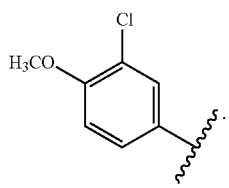

In certain embodiments, the present invention relates to any of the aforementioned compounds, wherein X is

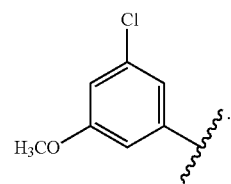

In certain embodiments, the present invention relates to any of the aforementioned compounds, wherein X is

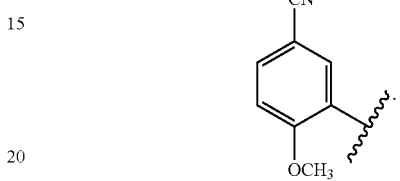

In certain embodiments, the present invention relates to any of the aforementioned compounds, wherein $R^2$ is ($C_1$-$C_6$)alkyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is unsubstituted ($C_1$-$C_6$)alkyl. In certain embodiments, the present invention relates to any of the aforementioned compounds, wherein $R^2$ is unsubstituted branched ($C_1$-$C_6$)alkyl.

In certain embodiments, the present invention relates to any of the aforementioned compounds, wherein $R^2$ is ($C_1$-$C_3$)alkyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is methyl optionally substituted with one, two or three substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is ethyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is n-propyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is i-propyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is methyl substituted with ($C_3$-$C_6$)cycloalkyl.

In certain embodiments, the present invention relates to any of the aforementioned compounds, wherein $R^2$ is ethyl substituted with —$CF_3$.

In certain embodiments, the present invention relates to any of the aforementioned compounds, wherein $R^2$ is ethyl substituted with —OH and —$CF_3$.

In certain embodiments, the present invention relates to any of the aforementioned compounds, wherein $R^2$ is ethyl substituted with cycoalkyl.

In certain embodiments, the present invention relates to any of the aforementioned compounds, wherein $R^2$ is ($C_3$-$C_{10}$)cycloalkyl optionally substituted with one, two, three, four or five substituents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is unsubstituted ($C_3$-$C_{10}$)cycloalkyl.

In certain embodiments, the present invention relates to any of the aforementioned compounds, wherein $R^2$ is cyclopropyl optionally substituted with one, two, three or four substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is cyclobutyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is cyclopentyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is cyclohexyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is cycloheptyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is cyclooctyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is phenyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is phenyl optionally substituted with one, two, three, four or five substitutents independently selected for each occurrence from the group consisting of —F, —Cl, —Br, —OH and —$CH_3$.

In certain embodiments, the present invention relates to any of the aforementioned compounds, wherein $R^2$ is indanyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is unsubstituted indanyl.

In certain embodiments, the present invention relates to any of the aforementioned compounds, wherein $R^2$ is tetrahydrothiophenyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is unsubstituted tetrahydrothiophenyl.

In certain embodiments, the present invention relates to any of the aforementioned compounds, wherein $R^2$ is thietanyl optionally substituted with one, two, three, four or five substitutents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

In certain embodiments, the present invention relates to any of the aforementioned compounds, wherein $R^2$ is unsubstituted thietanyl.

In certain embodiments, the present invention relates to any of the aforementioned compounds, wherein $R^2$ is

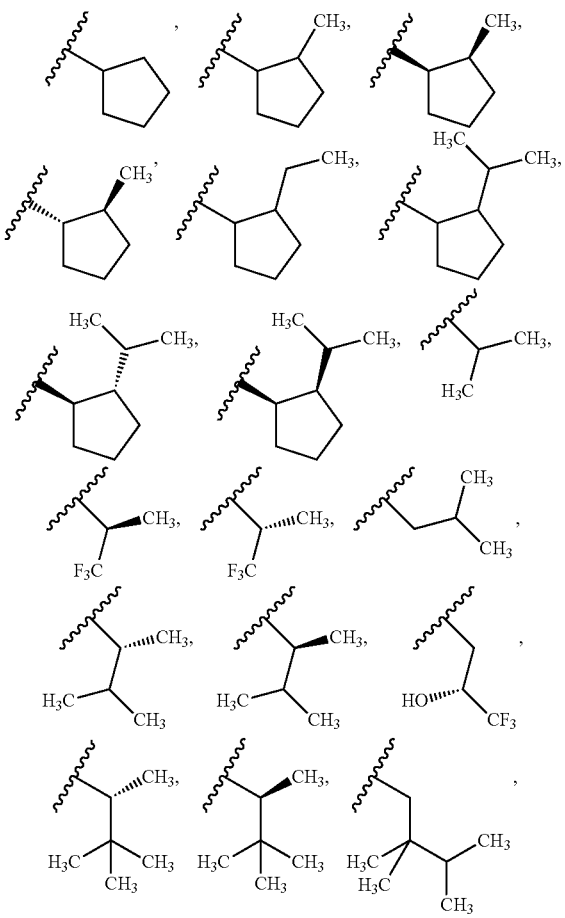

-continued

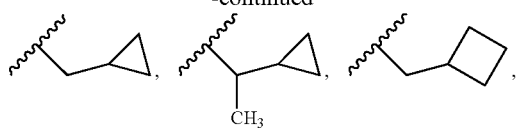

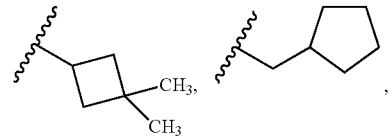

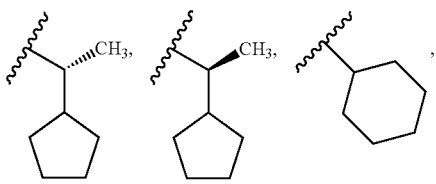

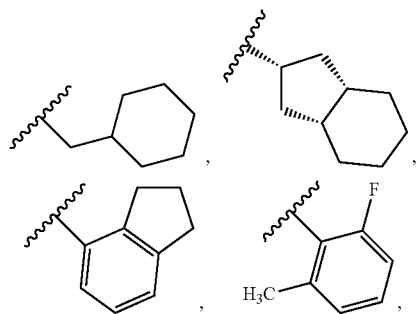

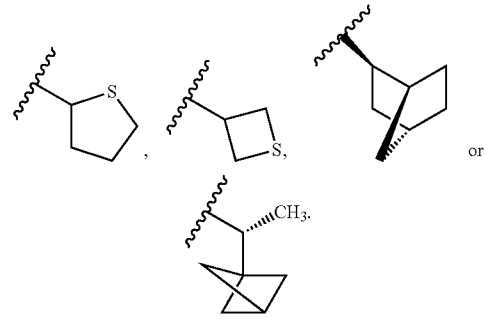

In certain embodiments, the present invention relates to any of the aforementioned compounds, wherein $R^2$ is

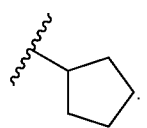

In certain embodiments, the present invention relates to any of the aforementioned compounds, wherein $R^2$ is

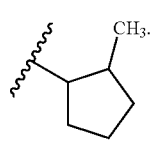 [SMILES: *C1CCCC1C]

In certain embodiments, the present invention relates to any of the aforementioned compounds, wherein $R^2$ is

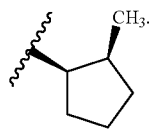 [SMILES: *[C@@H]1CCC[C@@H]1C]

In certain embodiments, the present invention relates to any of the aforementioned compounds, wherein $R^2$ is

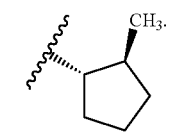 [SMILES: *[C@H]1CCC[C@@H]1C]

In certain embodiments, the present invention relates to any of the aforementioned compounds, wherein $R^2$ is

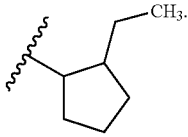 [SMILES: *C1CCCC1CC]

In certain embodiments, the present invention relates to any of the aforementioned compounds, wherein $R^2$ is

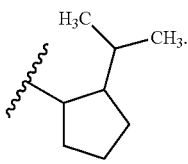 [SMILES: *C1CCCC1C(C)C]

In certain embodiments, the present invention relates to any of the aforementioned compounds, wherein $R^2$ is

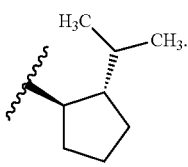 [SMILES: *[C@@H]1CCC[C@H]1C(C)C]

In certain embodiments, the present invention relates to any of the aforementioned compounds, wherein $R^2$ is

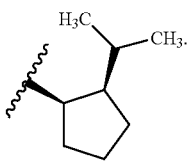 [SMILES: *[C@@H]1CCC[C@@H]1C(C)C]

In certain embodiments, the present invention relates to any of the aforementioned compounds, wherein $R^2$ is

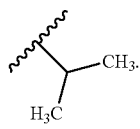

In certain embodiments, the present invention relates to any of the aforementioned compounds, wherein R² is

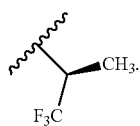

In certain embodiments, the present invention relates to any of the aforementioned compounds, wherein R² is

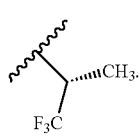

In certain embodiments, the present invention relates to any of the aforementioned compounds, wherein R² is

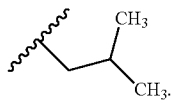

In certain embodiments, the present invention relates to any of the aforementioned compounds, wherein R² is

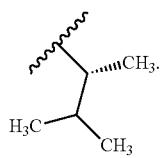

In certain embodiments, the present invention relates to any of the aforementioned compounds, wherein R² is

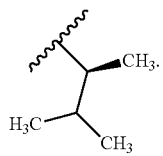

In certain embodiments, the present invention relates to any of the aforementioned compounds, wherein R² is

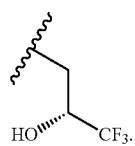

In certain embodiments, the present invention relates to any of the aforementioned compounds, wherein R² is

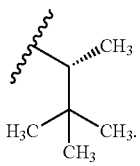

In certain embodiments, the present invention relates to any of the aforementioned compounds, wherein R² is

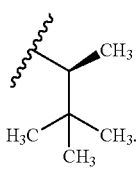

In certain embodiments, the present invention relates to any of the aforementioned compounds, wherein R² is

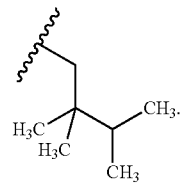

In certain embodiments, the present invention relates to any of the aforementioned compounds, wherein R² is

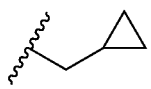

In certain embodiments, the present invention relates to any of the aforementioned compounds, wherein R² is

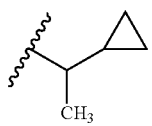

In certain embodiments, the present invention relates to any of the aforementioned compounds, wherein R² is

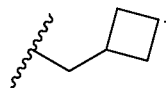

In certain embodiments, the present invention relates to any of the aforementioned compounds, wherein $R^2$ is

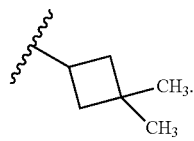

In certain embodiments, the present invention relates to any of the aforementioned compounds, wherein $R^2$ is

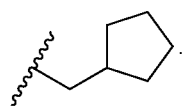 [SMILES: *CC1CCCC1]

In certain embodiments, the present invention relates to any of the aforementioned compounds, wherein $R^2$ is

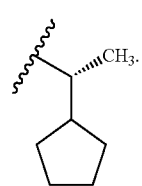 [SMILES: *[C@H](C)C1CCCC1]

In certain embodiments, the present invention relates to any of the aforementioned compounds, wherein $R^2$ is

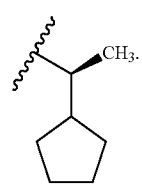 [SMILES: *[C@@H](C)C1CCCC1]

In certain embodiments, the present invention relates to any of the aforementioned compounds, wherein $R^2$ is

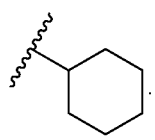

In certain embodiments, the present invention relates to any of the aforementioned compounds, wherein $R^2$ is

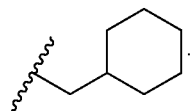 [SMILES: *CC1CCCCC1]

In certain embodiments, the present invention relates to any of the aforementioned compounds, wherein $R^2$ is

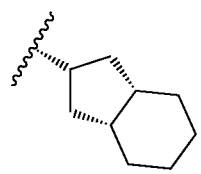

In certain embodiments, the present invention relates to any of the aforementioned compounds, wherein $R^2$ is

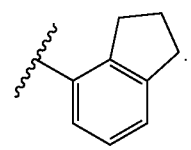 [SMILES: *c1cccc2c1CCC2]

In certain embodiments, the present invention relates to any of the aforementioned compounds, wherein $R^2$ is

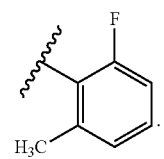

In certain embodiments, the present invention relates to any of the aforementioned compounds, wherein $R^2$ is

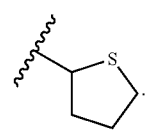

In certain embodiments, the present invention relates to any of the aforementioned compounds, wherein $R^2$ is

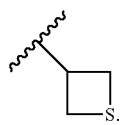

In certain embodiments, the present invention relates to any of the aforementioned compounds, wherein $R^2$ is

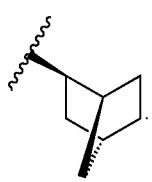 [SMILES: *[C@@H]1C[C@@H]2CC[C@H]1C2]

In certain embodiments, the present invention relates to any of the aforementioned compounds, wherein $R^2$ is

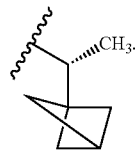 [SMILES: *[C@H](C)C12CC(C1)C2]

Another embodiment of the invention is a compound selected from the group consisting of the compounds of Examples 1-35 and pharmaceutically acceptable salts thereof.

Therapeutic Applications

It is contemplated that the compounds of Formula I provide therapeutic benefits to subjects suffering from an immune disorder or inflammatory disorder. Accordingly, one aspect of the invention provides a method of treating a disorder selected from the group consisting of an immune disorder or inflammatory disorder. The method comprises administering a therapeutically effective amount of a compound of Formula I to a subject in need thereof to ameliorate a symptom of the disorder, wherein Formula I are as described above. In certain embodiments, the particular compound of Formula I is a compound defined by one of the embodiments described above.

In certain embodiments, the disorder is an immune disorder. In certain other embodiments, the disorder is an inflammatory disorder. In certain other embodiments, the disorder is an autoimmune disorder. In certain other embodiments, the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

In certain other embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myositis, polymyositis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, giant cell arteritis, nonalcoholic hepatic steatosis, or an immune disorder associated with or arising from activity of pathogenic lymphocytes.

In certain embodiments, the psoriasis is plaque psoriasis, guttate psoriasis, inverse psoriasis, pustular psoriasis, or erythrodermic psoriasis.

In certain other embodiments, the disorder is noninfectious uveitis, Behcet's disease or Vogt-Koyanagi-Harada syndrome.

Another aspect of the invention provides for the use of a compound of Formula I in the manufacture of a medicament. In certain embodiments, the medicament is for treating a disorder described herein.

Another aspect of the invention provides for the use of a compound of Formula I for treating a medical disorder, such a medical disorder described herein.

Further, it is contemplated that compounds of Formula I can inhibit the activity of RORγ. Accordingly, another aspect of the invention provides a method of inhibiting the activity of RORγ. The method comprises exposing a RORγ to an effective amount of a compound of Formula I to inhibit said RORγ, wherein Formula I is as described above. In certain embodiments, the particular compounds of Formula I are the compound defined by one of the embodiments described herein.

Further, it is contemplated that compounds of Formula I can reduce the amount of interleukin-17 (IL-17) in a subject. IL-17 is a cytokine that affects numerous biological functions, including inducing and mediating pro-inflammatory responses. Accordingly, another aspect of the invention provides a method of reducing the amount of IL-17 in a subject. The method comprises administering to a subject an effective amount of a compound of I to reduce the amount of IL-17 in the subject, wherein Formula I is as described above. In certain embodiments, the particular compounds of Formula I are the compounds defined by one of the embodiments described herein.

In certain embodiments, the subject is a human. In certain embodiments, administering the compound reduces the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that compounds of Formula I may inhibit the synthesis of IL-17 in a subject. Accordingly, another aspect of the invention provides a method of inhibiting the synthesis IL-17 in a subject. The method comprises administering to a subject an effective amount of a compound of Formula I to inhibit the synthesis IL-17 in the subject, wherein Formula I is as described above. In certain embodiments, the particular compounds of Formula I are the compounds defined by one of the embodiments described herein.

The description above describes multiple embodiments providing definitions for variables used herein. The application specifically contemplates all combinations of such variables.

Combination Therapy

Another aspect of the invention provides for combination therapy. For example, the compounds of Formula I or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-a inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (ariflo) or roflumilast; (8) an antihistamine H1 receptor antagonist; (9) an od- and oc2-adrenoceptor agonist; (10) an anticholinergic agent; (11) a β-adrenoceptor agonist; (12) an insulin-like growth factor type I (IGF-1) mimetic; (13) a glucocorticosoid; (14) a kinase inhibitor such as an inhibitor of a Janus Kinase (e.g., JAK 1 and/or JAK2 and/or JAK 3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab, and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

In certain embodiments, the additional therapeutic agent is selected from the group consisting of corticosteroids, vitamin D3, anthralin and retinoids. In certain embodiments, the additional therapeutic agent is a corticosteroid. In certain embodiments, the additional therapeutic agent is vitamin D3. In certain embodiments, the additional therapeutic agent is anthralin. In certain embodiments, the additional therapeutic agent is a retinoid.

The amount of the compounds of Formula I and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a compound of Formula I may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the compound of Formula I and the additional therapeutic agent(s) are administered in doses commonly employed when such agents are used as monotherapy for treating the disorder. In other embodiments, the compound of Formula I and the additional therapeutic agent(s) are administered in doses lower than the doses commonly employed when such agents are used as monotherapy for treating the disorder. In certain embodiments, a compound of Formula I and the additional therapeutic agent(s) are present in the same composition, which is suitable for oral administration.

In certain embodiments, the compound of Formula I and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of a compound of Formula I, a pharmaceutically acceptable carrier, vehicle or diluent, and optionally at least one additional therapeutic agent listed above.

Pharmaceutical Compositions and Dosing Considerations

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The invention also includes pharmaceutical compositions utilizing one or more of the present compounds along with one or more pharmaceutically acceptable carriers, excipients, vehicles, etc.

Topical formulations of the presently disclosed compounds may be administered topically, (intra)dermally, or transdermally to the skin or mucosa. Topical administration using such preparations encompasses all conventional methods of administration across the surface of the body and the inner linings of body passages including epithelial and mucosal tissues, including transdermal, epidermal, buccal, pulmonary, ophthalmic, intranasal, vaginal and rectal modes of administration. Typical formulations for this purpose include gels, hydrogels, lotions, solutions, creams, colloid, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Such topical formulations may be prepared in combination with additional pharmaceutically acceptable excipients.

In certain embodiments, a penetration enhancer may be used. Examples of penetration enhancers include, for example, saturated C10-C18 fatty alcohols (such as decyl alcohol, lauryl alcohol, myristyl alcohol, cetyl alcohol and stearyl alcohol), cis-unsaturated C10-C18 fatty alcohols (such as oleyl alcohol, linoleyl alcohol, γ-linolenyl alcohol and linolenyl alcohol), C10-C18 fatty acids (which when saturated may include capric acid, lauric acid, myristic acid, palmitic acid, stearic acid and arachidic acid), cis-unsaturated fatty acids (such as palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid)). In certain embodiments, the penetration enhancers may be used amounts ranging from about 0.1 to about 5% (w/v).

In certain embodiments, topical formulations which contain one or more compounds of the invention in therapeutically effective amounts that may be given in daily or twice daily doses to patients in need.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Other excipients which enhance the stability of the formulations include aldehyde scavengers, such as glycerine and propylene glycol, and antioxidants, such as butyl hydroxyanisole (BHA), butyl hydroxytoluene (BHT), propyl gallate, ascorbic acid (Vitamin C), polyphenols, tocopherols (Vitamin E), and their derivatives.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg.

When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. In certain embodiments, preferred dosing is one administration per day.

The invention further provides a unit dosage form (such as a tablet or capsule) comprising a compound of Formula I or a specific compound described herein, or pharmaceutically acceptable salts thereof, in a therapeutically effective amount for the treatment of an immune or inflammatory disorder, such as one of the particular immune disorders or inflammatory disorders described herein.

General Synthetic Schemes and Procedures

The compounds of Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Compounds of Formula I may be prepared as single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diastereomers by common methods (e.g. crystallization, chromatographic separation, or distillation) and chemical reversion to scalemic compound, Simulated Moving Bed technology, or high/medium-pressure liquid chromatography or supercritical fluid chromatography employing a chiral stationary phase. These techniques may be performed on the final compounds of the invention or on any intermediates to compounds of the invention which bear a stereogenic center. Also, to facilitate separation by any of the methods described above, the compounds of the invention or any intermediates to the compounds of the invention which bear a stereogenic center may be transiently reacted with an achiral reagent, separated, and then reverted to scalemic compound by standard synthetic techniques.

Compounds of formula (I) are prepared as described in Scheme A. Cross-coupling of aryl halides A-1 (prepared as described in Schemes B-C) with vinyl boronates (prepared as described in Scheme D) or vinyl boronic acids affords compounds of the formula A-2. Subsequent reduction of the nitro group and the olefin concomitantly furnished compounds of formula A-3. The resulting amine A-3 may be transformed to amides by the reaction with acid chlorides in the presence of base or carboxylic acids with appropriate coupling agents to afford compounds of formula A-4.

SCHEME A

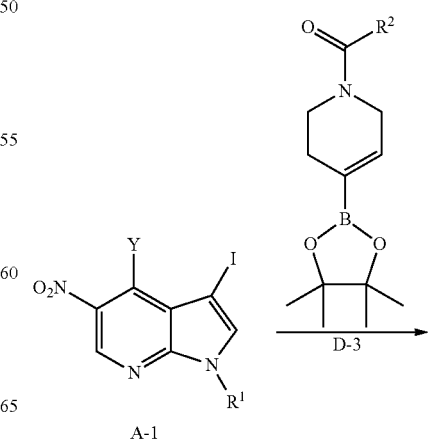

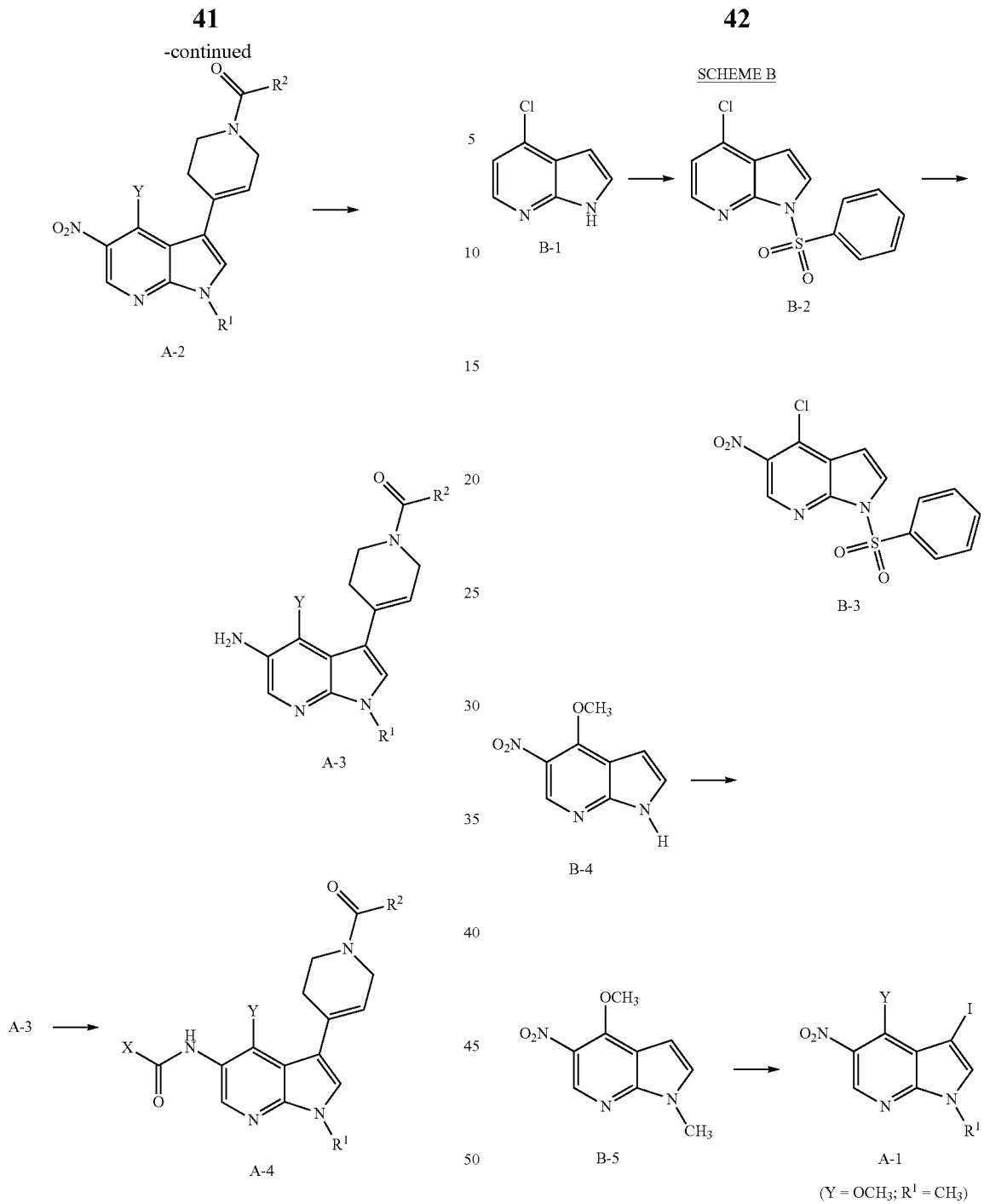

The intermediate of formula A-1 employed in Scheme A where Y is methoxy is prepared as described in Scheme B. Sulfonylation of 4-chloro-1H-pyrrolo[2,3-b]pyridine (B-1) with phenylsulfonyl chloride and base gave the resulting chloride B-2. Nitration of B-2 with a tetraalkylammonium salt affords compound B-3, which is then subjected to conventional alkoxylation conditions which installed the methyl ether at C-4 with concomitant removal of the phenyl sulfonyl group to provide compound B-4. Alkylation of the indole nitrogen by iodomethane in the presence of an inorganic base provides compounds of the formula B-5. Subjection of B-5 to conventional iodination conditions using N-iodosuccinimide ultimately provided compounds of formula A-1 (Y=OMe; $R^1$=Me).

Compounds of formula C-5 can be prepared as exemplified by the synthetic route described in Scheme C. Iodide A-1 was coupled with the Boc-protected piperidine C-1 through the use of conventional Suzuki conditions employing palladium tetrakistriphenylphoshine. Next, hydrogenation conditions could be used to convert nitroolefin C-2 to the corresponding aniline C-3. This resulting aniline could be substituted with a number of 3-cyanobenzoyl acids to provide structures resembling C-4. The Boc group within C-4 could be removed through the use of acid, and subsequently the piperidine nitrogen could be coupled with the appropriate acid chloride to furnish compounds of formula C-5.

SCHEME C

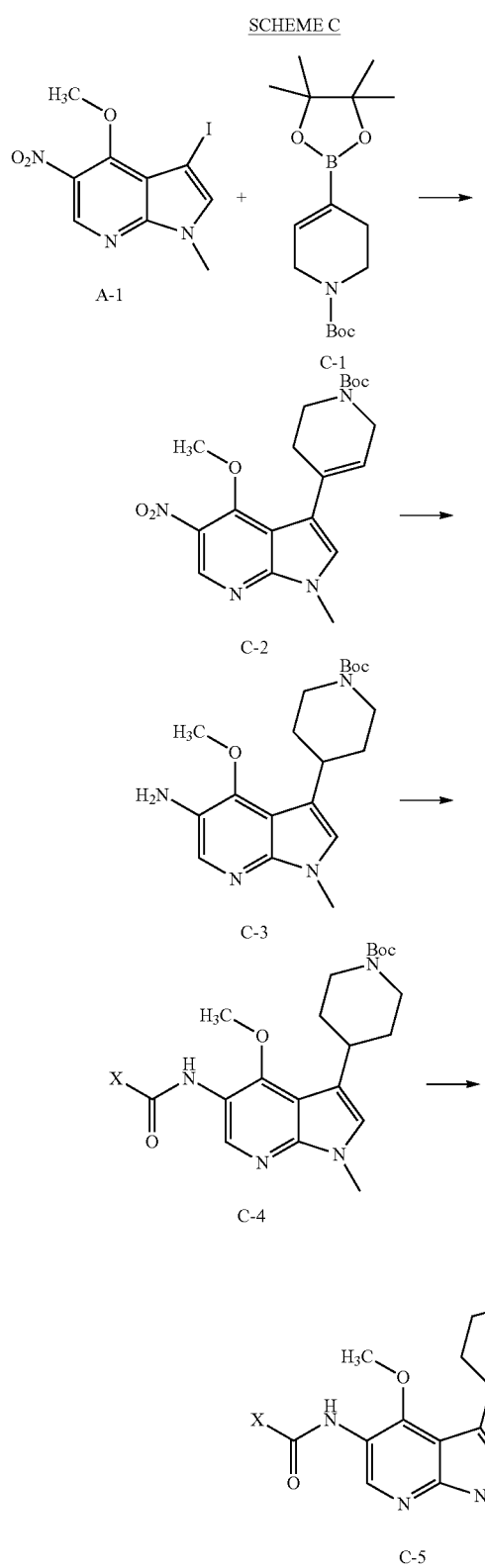

resulted in removal of the protecting group to furnish the ammonium salt resembling D-3. Amide bond formation with the appropriate acid chloride resulted in conversion to D-4, and this was followed by a zinc-mediated reductive cyclization reaction to secure azaindolines resembling D-5. Methylation of D-5 using iodomethane and sodium hydride preceded a nitration-oxidation step using tetramethylammonium nitrate to furnish nitroazaindoles resembling D-7, and this was followed by alkoxide substitution to generate the methyl ether D-8. Reduction of the nitro group, followed by acylation with the appropriate benzoyl chloride furnished compounds of formula D-9.

SCHEME D

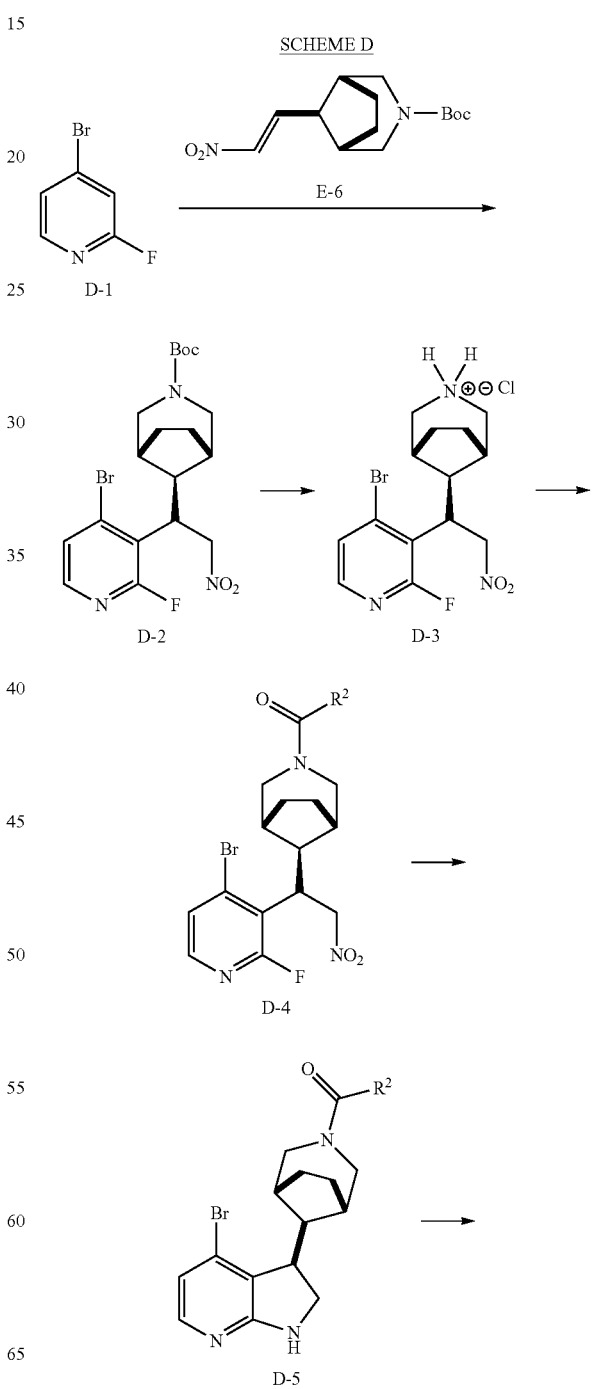

Compounds of formula D-9 can be prepared as exemplified by the synthetic route described in Scheme D. Lithiation of dihalopyridine D-1 followed by subjection to nitroolefin E-6 resulted in a 1,4-addition reaction to ultimately prepare D-2. Treatment of this Boc-protected compound with acid

SCHEME E

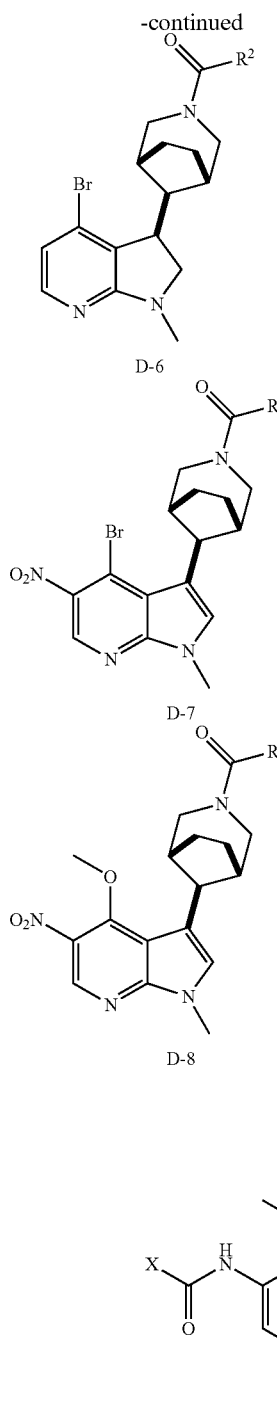

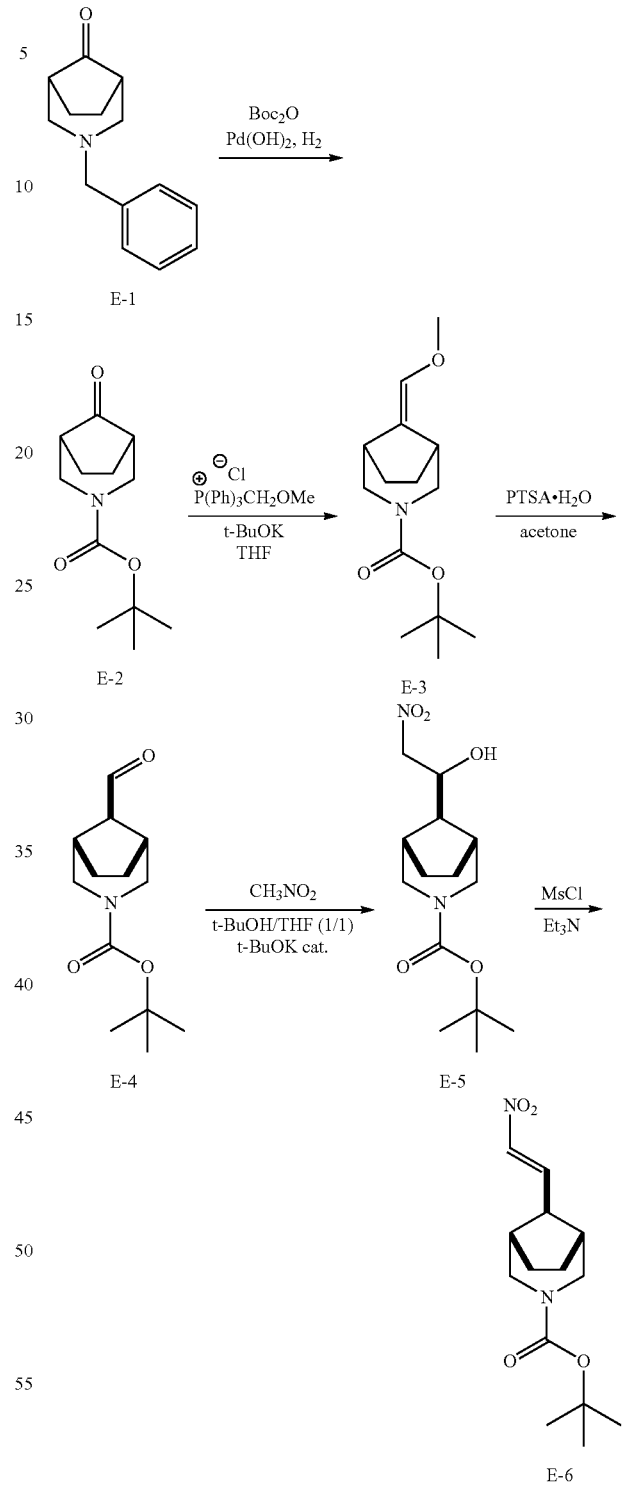

The intermediate of formula E-6 employed in Scheme D is prepared as described in Scheme E. Subjection of the commercially available N-benzyl-4-piperidone to hydrogenative debenzylation conditions in the presence of Boc anhydride resulted in the Boc-protected piperidone E-2. Homologation of this ketone through the use of (methoxymethyl)-triphenylphosphonium chloride and base generated the methyl vinyl ether E-3, which under acidic conditions resulted in aldehyde E-4. Next, exposure of E-4 to nitromethane in the presence of base resulted in nitroacohol E-5, and this could be converted to the corresponding nitrovinyl compound E-6 through the use of mesyl chloride and triethylamine.

Compounds of formula F-8 can be prepared as exemplified by the synthetic route described in Scheme F. Boron-halogen exchange of iodide F-1 through the use of catalytic palladium was followed by another palladium-catalyzed cross-coupling to install the piperidine ring as depicted in F-3. Next, alkoxylation by means of a nucleophilic aromatic substitution reaction converted the chloride in F-3 to the corresponding alkyl aryl ether F-4. This was then followed by hydrogenation reaction which reduced the alkene and the nitro group simultaneously to furnish the aniline F-5 which was immediately benzoylated under conventional amide bond-forming conditions using the corresponding chloride or activated acid to prepare compounds resembling F-6. Next, the tert-butyl carbamate was removed through the use of acid and the resulting piperidine was coupled with the corresponding acid chloride to furnish compounds of formula F-8.

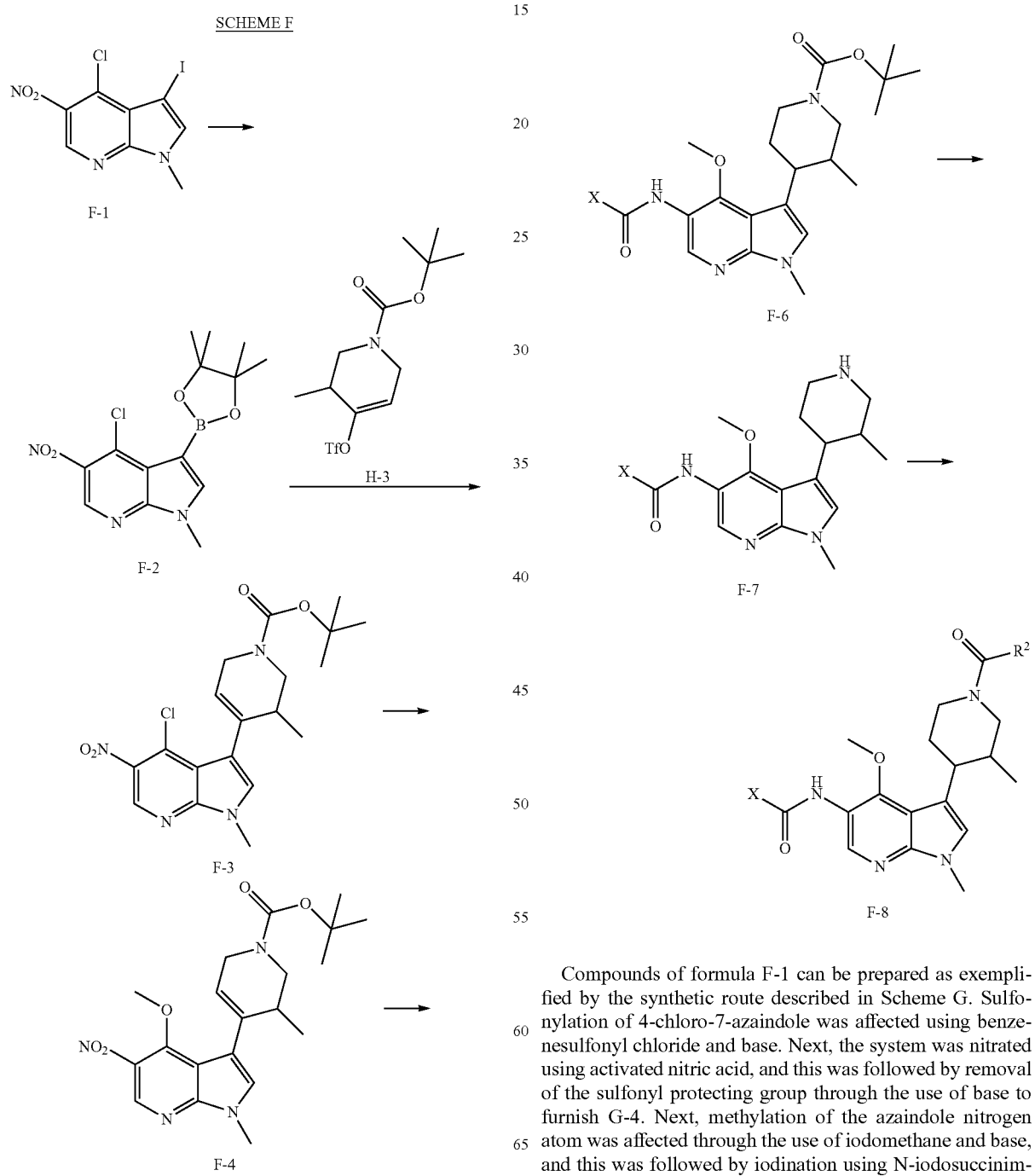

Compounds of formula F-1 can be prepared as exemplified by the synthetic route described in Scheme G. Sulfonylation of 4-chloro-7-azaindole was affected using benzenesulfonyl chloride and base. Next, the system was nitrated using activated nitric acid, and this was followed by removal of the sulfonyl protecting group through the use of base to furnish G-4. Next, methylation of the azaindole nitrogen atom was affected through the use of iodomethane and base, and this was followed by iodination using N-iodosuccinimide to ultimately furnish F-1.

SCHEME G

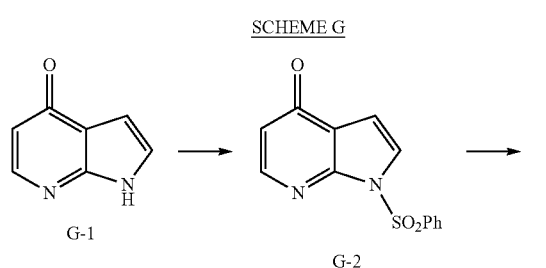

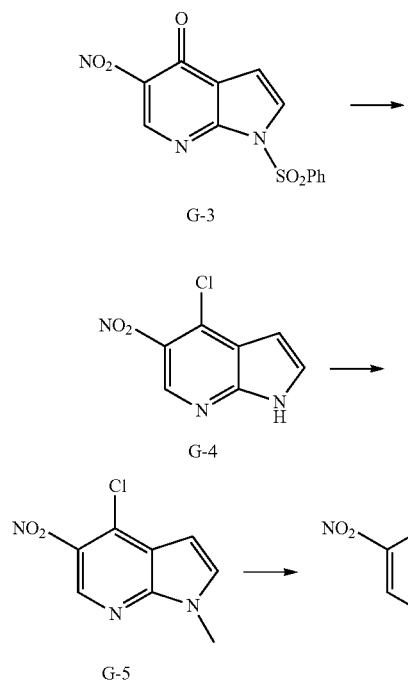

Compounds of formula H-3 can be prepared as exemplified by the synthetic route described in Scheme H. Hydrogenolysis of H-1 in the presence of Boc anhydride removed the benzyl group from the piperidine nitrogen and this was followed by immediate carbamate formation in situ to form carbamate H-2. Next, treatment with a strong base such as lithium hexamethyldisilylazide at cryogenic temperatures generated the kinetically controlled enolate, and this was trapped by treatment with N-phenyl triflamide to form vinyl triflate H-3.

SCHEME H

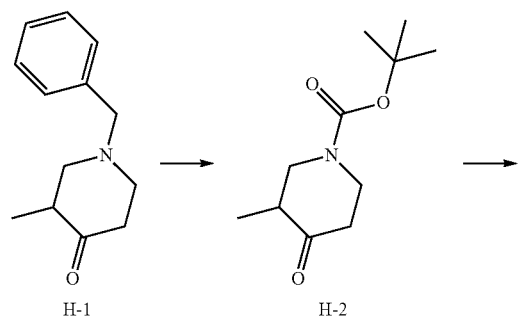

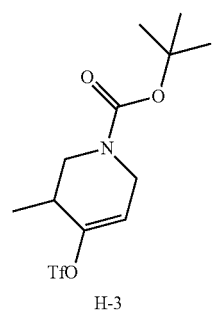

Compounds of formula I-4 can be prepared as exemplified by the synthetic route described in Scheme I. Amide bond formation using the appropriate benzoyl chloride and base was used to convert I-1 to I-2. Next, removal of the Boc protecting group was affected through the use of acid and this was followed by amide bond formation with the appropriate acid or acid chloride and base to furnish compounds of formula I-4.

SCHEME I

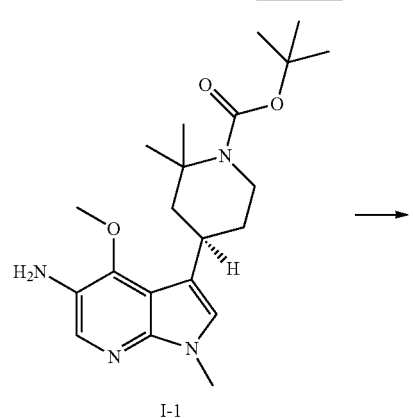

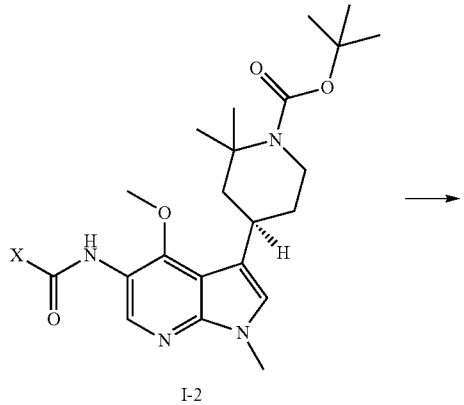

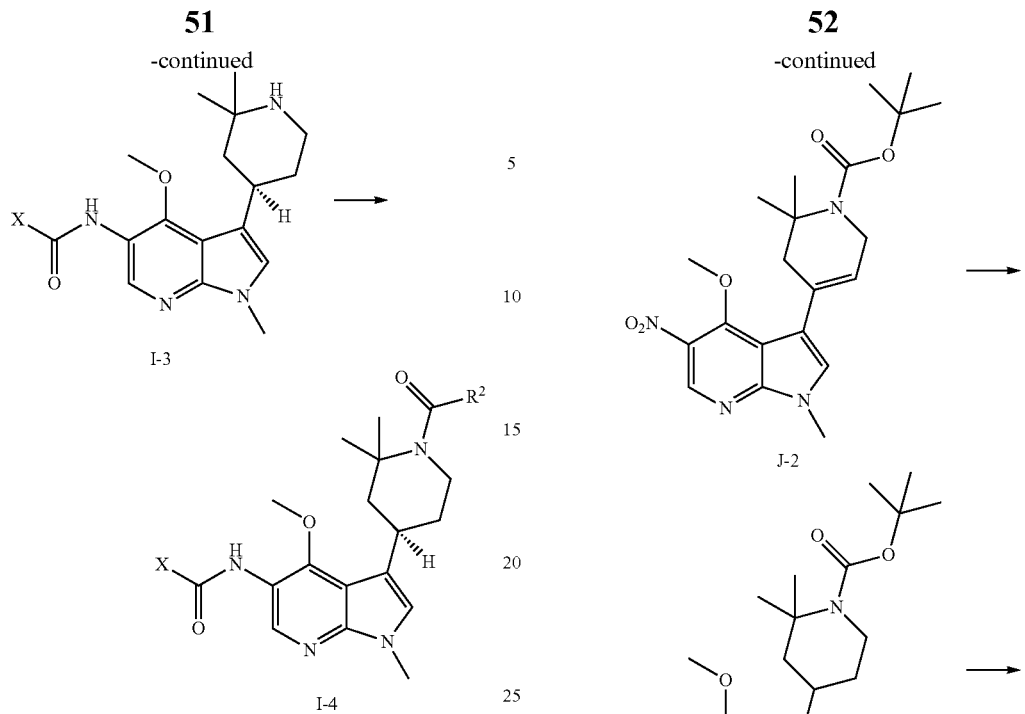

Compounds of formula I-1 can be prepared as exemplified by the synthetic route described in Scheme J. Boron-halogen exchange of iodide A-1 through the use of catalytic palladium was followed by another palladium-catalyzed cross-coupling to install the piperidine ring as depicted in J-2. Next, a hydrogenation reaction which reduced the alkene and the nitro group simultaneously furnished aniline J-3 which was then separated using SFC chiral resolution conditions to provide the separated enantiomers I-1 and J-4. The active enantiomer was determined through complete synthesis of both enantiomers and comparative assay activity.

SCHEME J

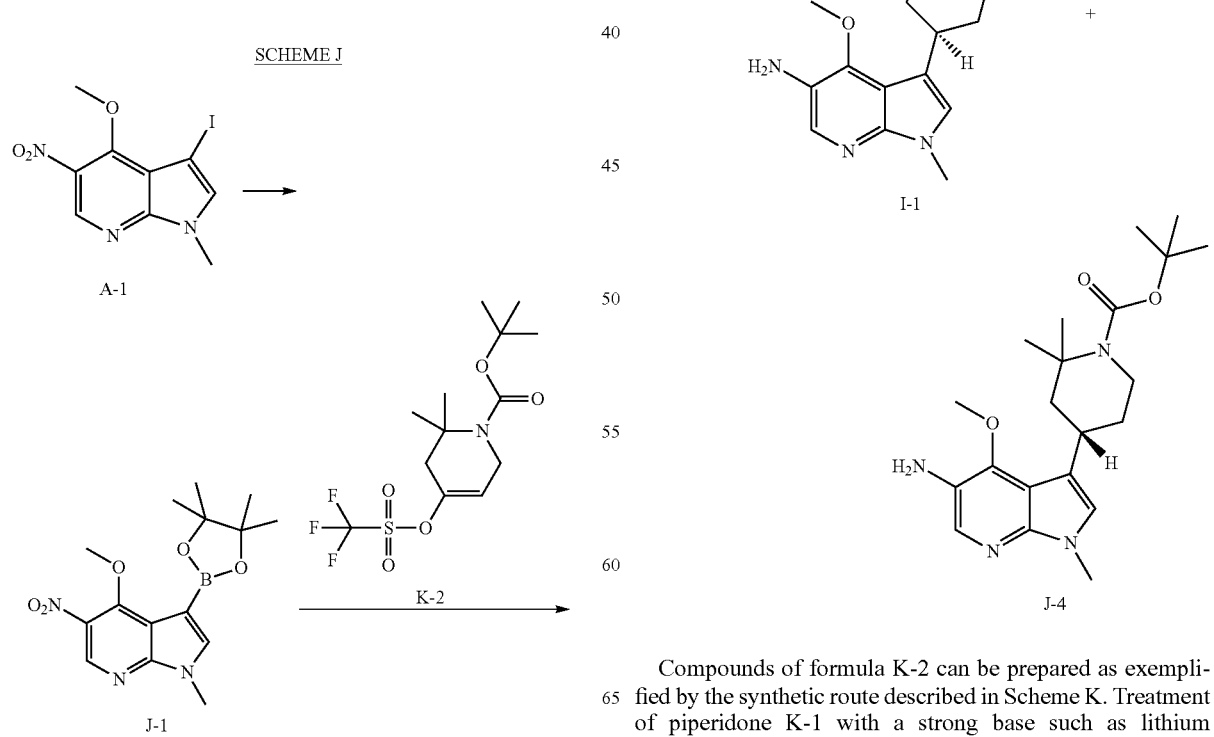

Compounds of formula K-2 can be prepared as exemplified by the synthetic route described in Scheme K. Treatment of piperidone K-1 with a strong base such as lithium hexamethyldisilylazide at cryogenic temperatures generated the kinetically controlled enolate, and this was trapped by treatment with N-phenyl triflamide to form vinyl triflate K-2.

SCHEME K

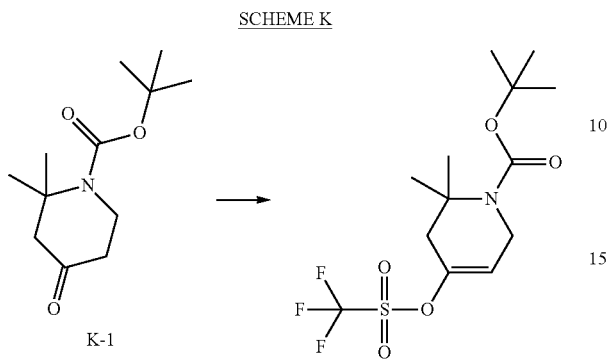

Carboxylic acids of the formula $R^2CO_2H$ employed in Schemes A, C, D, F, I, and subsequent Schemes may be commercially available, prepared by procedures described in the literature, or prepared as described in Scheme L. Examples of $R^2CO_2H$ prepared by literature procedures include the following: (S)-2,3,3-trimethylbutanoic acid (Kido, M. et al *Tetrahedron: Asym.* 2007, 18, 1934-47, commercially available from Ryan Sci); (R)-2,3,3-trimethylbutanoic acid (Kido, M. et al *Tetrahedron: Asym.* 2007, 18, 1934-47, commercially available from Bepharm); (R)-2,3-dimethylbutanoic acid (Tanasova, M. et al. *Eur. J. Org. Chem.* 2012, 3261-69, commercially available from Ryan Sci); 2,3-dihydro-1H-indene-4-carboxylic acid (Granger, R. et al. *Bull. Soc. Chim. Fr.* 1968, 1445-50); and thietane acid (see WO2013/7582, which is hereby incorporated by reference for the preparation of thietane acid). The following acids were prepared using procedures which are described in this application: (R)-2-cyclopentylpropanoic acid, and (S)-2-cyclopentylpropanoic acid. Specific examples of $R^2CO_2H$ according to the formula L-4 can be prepared from acids L-1 where R may be alkyl, cycloalkyl or aryl which are reacted with an optically active chiral oxazolidinone (e.g. (R)-benzyl oxazolidinone, (R)-4-Isopropyl-2-oxazolidinone) to provide compounds of the formula L-2. Base mediated alkylation and subsequent removal of the oxazolidinone auxiliary furnishes acids of the formula L-4 in high optical purity. By employing a chiral oxazolidinone of a different absolute configuration (e.g. (S)-benzyl oxazolidinone, (S)-4-Isopropyl-2-oxazolidinone), chiral acids L-4 of both configurations can be obtained.

SCHEME L

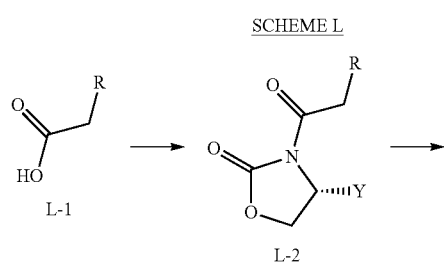

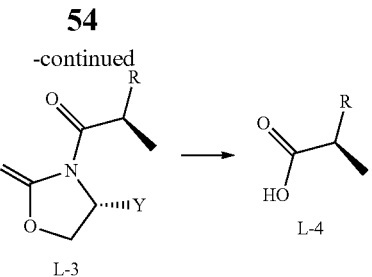

EXEMPLIFICATION

The invention now being generally described, will be more readily understood by reference to the following examples, which are included merely for purposes of illustration of certain aspects and embodiments of the present invention, and are not intended to limit the invention. The following illustrates the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Coupling constants (J values) are reported in Hertz.

Chiral purity of scalemic compounds was determined by chiral SFC (super-critical fluid chromatography) employing one of the following conditions: Method A: Chiralpak AD-3 150×4.6 mm ID, 3 μm, IPA/CO₂ (0.05% DEA), 5-40%, 2.5 mL/min, 10 min; Method B: Chiralpak AS-H 150×4.6 mm ID, 5 μm, MeOH/CO₂ (0.05% DEA), 5-40%, 3 mL/min, 10 min; Method C: ChiralCel OJ-H 250×4.6 mm ID, 5 μm, IPA/CO₂ (0.05% DEA), 5-40%, 2.35 mL/min, 10 min; Method D: Lux Cellulose-1 250 mm×4.6 mm ID, 5 μm, MeOH/CO₂ (0.2% NH₄⁺), 5-60%, 3 mL/min, 10 min; Method E: ChiralPak AD-3 50×4.6 mm ID, 3 μm, IPA/CO₂ (0.05% DEA), 5-40%, 2.5 mL/min, 10 min; Method F: ChiralCel OD-3 150×4.6 mm ID, 3 μm, IPA/CO₂ (0.05% DEA) 40%, 2.5 mL/min; Method G: ChiralCel OJ-H 100× 4.6 mm ID, 5 μm, Ethanol/CO₂ (0.05% DEA), 5-20%, 2.35 mL/min, 20 min; Method H: Chiralcel OJ-3 50×4.6 mm, 3 μm, MeOH/CO₂ (0.05% DEA), 5-40%, 4 mL/min, 3 min; Method I: Chiralpak AD-3 50×4.6 mm, 3 μm, EtOH/CO₂ (0.05% DEA), 5-40%, 4 mL/min, 3 min; Method J: Chiralcel OD-H 4.6×100 mm, 5 μm, EtOH/CO₂ (0.2% NH₄⁺), 40-60%, 1.5 mL/min, 5 min; Method K: Chiralcel OJ-3 50×4.6 mm, 3 μm, MeOH/CO₂ (0.05% DEA), 5-40%, 4 mL/min, 10 min; Method L: DIKMA Diamonsil (2) C18 200×20 mm 5 um MeCN/H₂O, 35 ml/min, 10 min; Method M: Ultimate XB-C18 3.0×50 mm, 3 μm, MeCN/H₂O, 35 ml/min, 10 min; Method N: Chiralpak AS-H 250×4.6 mm, 5 μm, MeOH/CO₂ (0.05% DEA), 5-40%, 2.5 mL/min, 10 min; Method O: Chiralcel OJ-R 150×4.6 mm, 5 μm, MeCN/H₂O (0.069% TFA), 0.8 mL/min, 20 min; Method P: Chiralpak AS-H 250×4.6 mm ID, 5 μm, EtOH/CO$_2$ (0.05% DEA), 20%, 2.35 mL/min, 5 min; Method Q: Chiralpak AS-RH 150×4.6 mm ID, 5 μm, H$_2$O/CH$_3$CN (0.069% TFA), 10-80%, 0.8 mL/min, 25 min; Method R: Chiralpak AS-H 250×4.6 mm ID, 5 μm, MeOH/CO$_2$ (0.05% DEA), 5-40%, 2.5 mL/min, 15 min; Method S: Chiralcel OJ-H 100×4.6 mm ID, 5 μm, CH$_3$OH/CO$_2$, 20%, 1.5 mL/min, 8 min; Method T: Chiralpak AS-H 150×4.6 mm ID, 5 μm, MeOH/CO$_2$ (0.05% DEA), 30%, 1.5 mL/min, 6 min; Method U: Chiralcel OJ 300×50 mm ID, 10 μm, MeOH/NH$_3$H$_2$O, 20%, 200 mL/min, 15 min.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate Rf's or retention times (RetT).

The chemical names for the compounds of the invention described below were generated using CambridgeSoft's ChemBioDraw Ultra version 13.0.2 (CambridgeSoft Corp., Cambridge Mass.).

The following abbreviations are used herein: DCM: dichloromethane; DEA: diethylamine; DIPEA: diisopropylethylamine; DMAP: Dimethylamino pyridine; DME: 1,2-dimethoxyethane; DMF: dimethylformamide; EtOAc: ethyl acetate; EtOH: ethanol; HATU: 1-[bis(dimethylamino)-methylene]-1H-1,2,3-triazolo[4,5-b]pyridinium 3-oxid hexafluorophosphate; MeOH: methanol; MTBE: methyl t-butyl ether; PE: petroleum ether; TEA: triethylamine; TFAA: Trifluoroacetic anhydride; and THF: tetrahydrofuran.

Example 1

Preparation of 3-cyano-N-(3-(1-(cyclopentanecarbonyl)piperidin-4-yl)-4-methoxy-1-methyl-1H-pyrrolo[2,3-b]pyridin-5-yl)benzamide

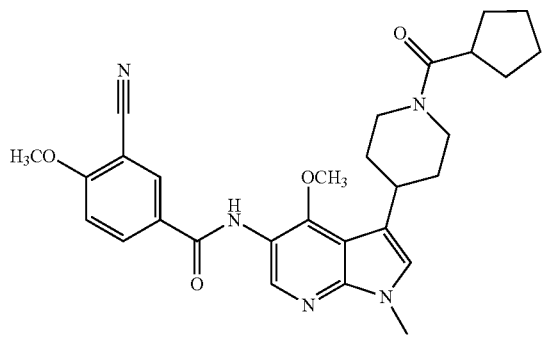 [SMILES: COc1ccc(C(=O)Nc2cnc3c(c(C4CCN(C(=O)C5CCCC5)CC4)cn3C)c2OC)cc1C#N]

Step 1: 4-chloro-1-(phenylsulfonyl)-1H-pyrrolo[2,3-b]pyridine. To a RB flask charged with 4-chloro-1H-pyrrolo[2,3-b]pyridine (250 g, 1.64 mol) was added 10 L of DCM at rt. To this mixture was added phenylsulfonyl chloride (318.5 g, 1.8 mol), then dimethylaminopyridine (DMAP, 20 g, 0.16 mol), then TEA (248.5 g, 2.46 mol) sequentially at 0° C. The resulting mixture was warmed to rt, and stirred for 18 hours at this temperature. The reaction was then brought to acidic pH (~2) by adding 1N HCl. The organic layer was then extracted and washed with saturated sodium bicarbonate (3 L), then brine (3 L). The organic layer was dried over sodium sulfate, filtered, and concentrated to give the title compound (461 g, 96%) as a brown solid which required no further purification; LC/MS [M]: 292.7.

Step 2: 4-chloro-5-nitro-1-(phenylsulfonyl)-1H-pyrrolo[2,3-b]pyridine. To a solution of 4-chloro-1-(phenylsulfonyl)-1H-pyrrolo[2,3-b]pyridine (451 g, 1.54 mol) in 6 L of dry DCM was added solid tetramethylammonium nitrate (420 g, 3.08 mol). TFAA (647 g, 3.08 mol) was added drop-wise over the course of 30 minutes while keeping the inner temperature between 0 and 5° C. After addition was complete, the resulting mixture was stirred at 0° C. for an additional 30 mins, then the reaction was allowed to warm to 18° C. and stirred at this temperature for 20 h. The reaction was then combined with water (1 L) and the organic layer was extracted. The organic layer was then washed with water (2 L×2) and brine (4 L). The organic layer was then dried over sodium sulfate, filtered, and concentrated to give the title compound (348 g, 66%) as a yellow solid which required no further purification: LC/MS [M+H+]: 337.8; $^1$H NMR (400 MHz, DMSO-d$_6$) δ ppm 9.09 (s, 1H), 8.29-8.27 (m, 1H), 8.18-8.16 (m, 2H), 7.81-7.77 (m, 1H), 7.69-7.66 (m, 2H), 7.11-7.10 (m, 1H).

Step 3: 4-methoxy-5-nitro-1H-pyrrolo[2,3-b]pyridine. To the suspension of 4-chloro-5-nitro-1-(phenylsulfonyl)-1H-pyrrolo[2,3-b]pyridine (397 g, 1.18 mol) in 8 L of methanol at room temperature, was added sodium methoxide (320 g, 5.9 mol) carefully. The resulting mixture was heated to reflux for 18 h, and then the mixture was cooled to room temperature, filtered, and concentrated. The resulting solid was dried, and then the cake was rinsed with cold water and chilled MeOH several times to rid the cake of impurities. The cake was then dried to give crude the title compound (180 g, 74%) as a yellow solid which was carried forward in the synthetic sequence without any further purification or characterization.

Step 4: 4-methoxy-1-methyl-5-nitro-1H-pyrrolo[2,3-b]pyridine. To a flask charged with the crude 4-methoxy-5-nitro-1H-pyrrolo[2,3-b]pyridine (180 g, 0.93 mol) and dry DMF (2 L). The resulting solution was then cooled to 0° C. and to this mixture was added 60% sodium hydride in dispersion oil (51 g, 1.26 mol) portionwise carefully over the course of 30 minutes while keeping the temperature at 0° C. To this mixture was then added iodomethane (400 g, 2.9 mol) dropwise over the course of 15 minutes. The reaction mixture was then warmed gradually to 25° C. and then stirred for 18 hours. The reaction mixture was then carefully poured into 8 L of water and stirred for 10 minutes. The reaction was then filtered and the resulting filter cake was washed with water (500 mL×6), and dried in a vacuum oven to give the title compound (149 g, 76%) as a yellow solid which required no further purification: LC/MS [M+H]: 207.8; $^1$H NMR (400 MHz, CDCl$_3$) δ ppm 8.85 (s, 1H), 7.19-7.18 (m, 1H), 6.84-6.83 (m, 1H), 4.44 (s, 3H), 3.90 (s, 3H).

Step 5: 3-iodo-4-methoxy-1-methyl-5-nitro-1H-pyrrolo[2,3-b]pyridine. To a flask charged with a solution of 4-methoxy-1-methyl-5-nitro-1H-pyrrolo[2,3-b]pyridine (149 g, 720 mmol) in dry DMF (150 mL) at 25° C. was added solid N-iodosuccinimide (195 g, 864 mmol). The resulting mixture was stirred at 25° C. for 24 hours. To this mixture was then added water (800 mL) and the resulting mixture was stirred for 5 minutes and then the resulting precipitate was filtered. The filter cake was collected, washed with water (500 mL×3), and dried under reduced pressure to give the crude product which was then triturated with EtOAc (600 mL) overnight. The mixture was then filtered and the filtered cake was dried under reduced pressure to provide the title compound (151 g, 63%) as a yellow solid which required no further purification. LC/MS [M+H]: 333.8; ¹H NMR (400 MHz, CDCl₃) δ ppm 8.94 (s, 1H), 7.35 (s, 1H), 4.17 (s, 3H), 3.91 (s, 3H).

Step 6: tert-butyl 4-(4-methoxy-1-methyl-5-nitro-1H-pyrrolo[2,3-b]pyridin-3-yl)-3,6-dihydropyridine-1(2H)-carboxylate. A mixture of 3-iodo-4-methoxy-1-methyl-5-nitro-1H-pyrrolo[2,3-b]pyridine (A-1) (3000 mg, 9.0 mmol), tert-butyl 4-(4,4,5,5-tetramethyl-1,3,2-dioxaborolan-2-yl)-3,6-dihydropyridine-(2H)-carboxylate (commercial; also can be prepared as described by Eastwood, P. R. *Tetrahedron Lett.* 2000, 41, 3705-3708; 3.62 g, 11.7 mmol), and potassium phosphate (3.80 g, 18.0 mmol) in dioxane/H₂O (150 mL, 9/1) was degassed using nitrogen bubbling for 30 minutes. To this mixture was then added Pd(PPh₃)₄ (515 mg, 0.45 mmol) as a solid all at once, and the resulting reaction mixture was heated to 75° C. for 24 hours under a flow of nitrogen. The reaction was then cooled and filtered through a pad of Celite®. The Celite® pad was rinsed with dioxane and the combined filtrates were evaporated to obtain a crude material which was then purified using silica gel chromatography (20-30% EtOAc in PE) to afford the title compound (2.76 g, 79%) as a yellow gum. ¹H NMR (400 MHz, CDCl₃) δ ppm 8.85 (s, 1H), 7.13 (s, 1H), 5.95 (s, 1H), 4.08 (br s, 2H), 3.96 (s, 3H), 3.87 (s, 3H), 3.65 (br s, 2H), 2.51 (br s, 2H), 1.49 (s, 9H).

Step 7: tert-butyl 4-(5-amino-4-methoxy-1-methyl-1H-pyrrolo[2,3-b]pyridin-3-yl)piperidine-1-carboxylate. To a flask charged with tert-butyl 4-(4-methoxy-1-methyl-5-nitro-1H-pyrrolo[2,3-b]pyridin-3-yl)-3,6-dihydropyridine-1(2H)-carboxylate (2.8 g, 7.2 mmol) was added methanol (100 mL) and the resulting solution was gently warmed to 75° C. This mixture was then treated with decolorizing carbon (720 mg) and allowed to stir at for 30 minutes while allowing it to cool to 25° C. The mixture was then filtered through a pad of Celite®, and the filtrates were then transferred to a Parr reactor. To this vessel was added Pd(OH)₂ (20% on Carbon, 300 mg). The vessel's atmosphere was replaced with hydrogen four times and final hydrogen pressure was set to 50 psi and the temperature of the vessel was set to 50° C. The reaction vessel was shaken for 24 hours under these conditions, then cooled to 25° C., and filtered through a pad of Celite®. The filtrates were then concentrated under reduced pressure to give the desired product the title compound as a brown gum (2.3 g, 93% crude), which was used directly for the next step without further purification: LC/MS [M+H+]: 361.0; ¹H NMR (400 MHz, CDCl₃) δ ppm 8.12 (s, 1H) 6.81 (s, 1H), 4.23 (br s, 2H), 3.98 (s, 3H), 3.78 (s, 3H), 3.00-2.85 (m, 2H), 2.07-1.43 (m, 12H).

Step 8: tert-butyl 4-(5-(3-cyanobenzamido)-4-methoxy-1-methyl-1H-pyrrolo[2,3-b]pyridin-3-yl)piperidine-1-carboxylate. To a mixture of tert-butyl 4-(5-amino-4-methoxy-1-methyl-1H-pyrrolo[2,3-b]pyridin-3-yl)piperidine-1-carboxylate (1.85 g, 5.37 mmol) was added 3-cyano-4-methoxybenzoic acid (1.05 g, 5.91 mmol), Mukaiyama reagent (2-chloro-1-methylpyridinium iodide, 2.74 g, 10.7 mmol), and diisopropylethylamine (DIEA, 2.78 g, 21.5 mmol) in THF (50 mL). The mixture was then heated to 75° C. for 10 hours. The reaction mixture was then cooled to 25° C., the solvent was removed under vacuum, and the resulting residue was partitioned between DCM (25 mL) and H₂O (25 mL). The organic layer was collected, dried, concentrated, and purified by silica gel chromatography (50%-80% EtOAc in PE) to afford the title compound (2.1 g, 75%) as a grey solid which was carried further in the sequence without any further purification or characterization: LC/MS [M+H+]: 520.1.

Step 9: 3-cyano-N-(4-methoxy-1-methyl-3-(piperidin-4-yl)-1H-pyrrolo[2,3-b]pyridin-5-yl)benzamide hydrochloride salt. To a solution of 4-(5-(3-cyanobenzamido)-4-methoxy-1-methyl-1H-pyrrolo[2,3-b]pyridin-3-yl)piperidine-1-carboxylate (2000 mg, 3.84 mmol), in DCM (30 mL) was added 10 mL of 4 M HCl in dioxane (30 mL). The resulting reaction mixture was then stirred at 25° C. for 4 hours followed by concentrated under reduced pressure to afford the intermediate HCl salt as a white solid (1.32 g, 81.8%) which was carried further in the synthetic sequence without any further purification or characterization.

Step 10. 3-cyano-N-(3-(1-(cyclopentanecarbonyl)piperidin-4-yl)-4-methoxy-1-methyl-1H-pyrrolo[2,3-b]pyridin-5-yl)benzamide. 3-cyano-N-(4-methoxy-1-methyl-3-(piperidin-4-yl)-1H-pyrrolo[2,3-b]pyridin-5-yl)benzamide hydrochloride salt (1.32 g, 3.10 mmol) was taken up in DCM (50 mL) and combined with DIEA (2.46 g, 19.1 mmol) at 0° C. and stirred until the a solution evolved. To this solution was added a prepared solution of cyclopentanoyl chloride (692 mg, 5.24 mmol) in DCM (2 mL) dropwise at 0° C. over the course of 30 minutes. The reaction was monitored by LCMS until the reaction was complete (about 1 hour). To the reaction mixture was added water (20 mL). The layers were separated, and the organic layer was dried over sodium sulphate, filtered, and concentrated to afford a crude residue which was then purified by silica gel chromatography (1-3% MeOH in EtOAc) to afford the title compound (1.3 g, 53%) as a light red solid: LC/MS [M+H]: 516.1; ¹H NMR (400 MHz, CD₃OD) δ 8.33-8.31 (m, 2H), 8.14 (s, 1H), 7.37-7.24 (m, 1H), 7.12 (s, 1H), 4.70-4.67 (m, 2H), 4.23-4.20 (m, 1H), 4.07 (s, 3H), 4.03 (s, 3H), 3.80 (s, 3H), 3.25-3.14 (m, 2H), 3.12-3.10 (m, 1H), 2.81-52.78 (m, 1H), 2.20-2.06 (m, 2H), 1.89-1.31 (m, 10H).

Examples 2-17

The following Examples 2-17 were prepared analogous to Example 1 employing the appropriate carboxylic acid coupling reagent in Steps 8 and 9,

| Ex. | Structure | Name/Characterization |
|---|---|---|
| 2 | 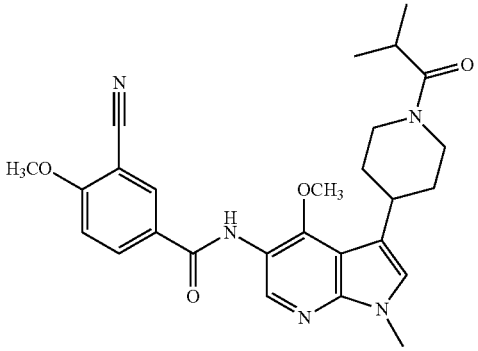 [SMILES: COc1ccc(C(=O)Nc2cnc3c(c(C4CCN(C(=O)C(C)C)CC4)cn3C)c2OC)cc1C#N] | 3-cyano-N-(3-(1-isobutyrylpiperidin-4-yl)-4-methoxy-1-methyl-1H-pyrrolo[2,3-b]pyridin-5-yl)-4-methoxybenzamide. LC/MS [M + H]: 490.0; ¹H NMR (400 MHz, CD₃OD): δ 8.34-8.32 (m, 2H), 8.14 (s, 1H), 7.38-7.36 (m, 1H), 7.13 (s, 1H), 4.72-4.69 (m, 1H), 4.21-4.18 (m, 1H), 4.08 (s, 3H), 4.04 (s, 3H), 3.80 (s, 3H), 3.45-3.20 (m, 2H), 3.06-3.01 (m, 1H), 2.81-2.78 (m, 1H), 2.22-2.11 (m, 2H), 1.66-1.55 (m, 2H), 1.16-1.12 (m, 6H). |

| Ex. | Structure | Name/Characterization |
|---|---|---|
| 3 | 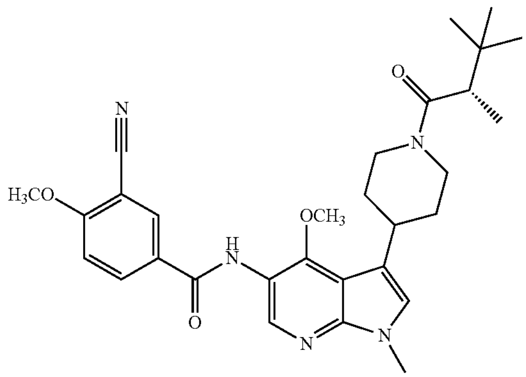 [SMILES: COc1ccc(C(=O)Nc2cnc3c(c(C4CCN(C(=O)[C@@H](C)C(C)(C)C)CC4)cn3C)c2OC)cc1C#N] | (S)-3-cyano-4-methoxy-N-(4-methoxy-1-methyl-3-(1-(2,3,3-trimethylbutanoyl)piperidin-4-yl)-1H-pyrrolo[2,3-b]pyridin-5-yl)benzamide LC/MS [M + H]: 532.1; Chiral LC: Rt = 7.17 min (Method K); $^1$H NMR (400 MHz, CDCl$_3$) δ 8.83-8.80 (m, 1H), 8.25-8.17 (m, 2H), 8.10-8.06 (m, 1H), 7.12-7.10 (m, 1H), 6.88-6.86 (m, 1H), 4.90-4.84 (m, 1H), 4.23-4.20 (m, 1H), 4.04 (s, 3H), 3.98 (s, 3H), 3.83 (s, 3H), 3.23-3.09 (m, 2H), 2.73-2.66 (m, 2H), 2.18-2.08 (m, 2H), 1.54-1.47 (m, 2H), 1.13-1.10 (m, 3H), 1.01-0.99 (m, 9H). |
| 4 | 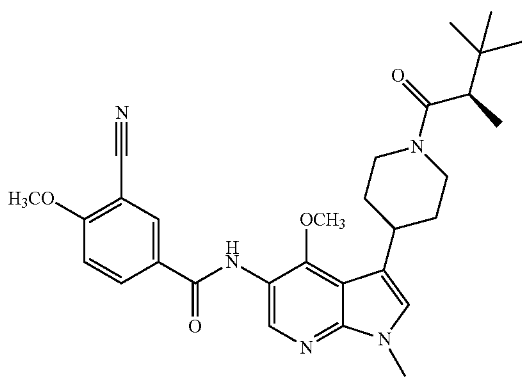 [SMILES: COc1ccc(C(=O)Nc2cnc3c(c(C4CCN(C(=O)[C@H](C)C(C)(C)C)CC4)cn3C)c2OC)cc1C#N] | (R)-3-cyano-4-methoxy-N-(4-methoxy-1-methyl-3-(1-(2,3,3-trimethylbutanoyl)piperidin-4-yl)-1H-pyrrolo[2,3-b]pyridin-5-yl)benzamide LC/MS [M + H]: 532.1; Chiral LC: Rt = 6.01 min (Method K); $^1$H NMR (400 MHz, CDCl$_3$) δ 8.84-8.81 (m, 1H), 8.25-8.15 (m, 2H), 8.06-8.02 (m, 1H), 7.12-7.10 (m, 1H), 6.88-6.87 (m, 1H), 4.90-4.85 (m, 1H), 4.23-4.20 (m, 1H), 4.04 (s, 3H), 3.98 (s, 3H), 3.83 (s, 3H), 3.23-3.09 (m, 2H), 2.73-2.63 (m, 2H), 2.20-2.12 (m, 2H), 1.54-1.48 (m, 2H), 1.13-1.10 (m, 3H), 1.02-0.99 (m, 9H). |
| 5 | 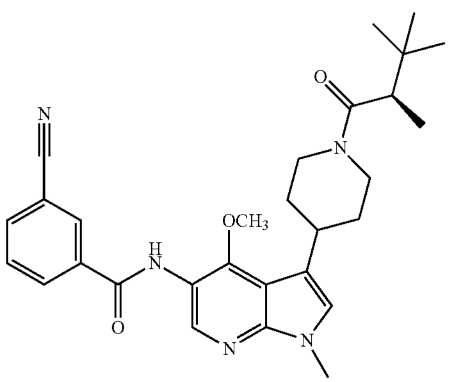 [SMILES: COc1c(NC(=O)c2cccc(C#N)c2)cnc2c1c(C1CCN(C(=O)[C@H](C)C(C)(C)C)CC1)cn2C] | (R)-3-cyano-N-(4-methoxy-1-methyl-3-(1-(2,3,3-trimethylbutanoyl)piperidin-4-yl)-1H-pyrrolo[2,3-b]pyridin-5-yl)benzamide. LC/MS [M + H]: 502.1; Chiral LC: Rt = 3.09 min (Method B); $^1$H NMR (400 MHz, CDCl$_3$) δ 8.88-8.84 (m, 1H), 8.27-8.15 (m, 3H), 7.88-7.87 (m, 1H), 7.69-7.66 (m, 1H), 6.89-6.87 (m, 1H), 4.87-4.84 (m, 1H), 4.23-4.20 (m, 1H), 3.99 (s, 3H), 3.84 (s, 3H), 3.24-3.05 (m, 2H), 2.73-2.58 (m, 2H), 2.25-2.06 (m, 2H), 1.68-1.48 (m, 2H), 1.13-1.10 (m, 3H), 1.02-0.99 (m, 9H). |
| 6 | 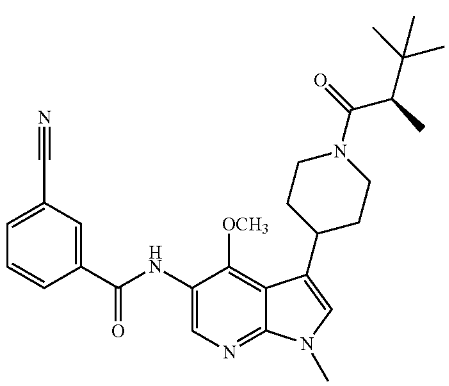 | (R)-3-cyano-N-(3-(1-(2,3-dimethylbutanoyl)piperidin-4-yl)-4-methoxy-1-methyl-1H-pyrrolo[2,3-b]pyridin-5-yl)benzamide. LC/MS [M + H]: 488.2; Chiral LC: Rt = 4.07 min (Method P); $^1$H NMR (400 MHz, CDCl$_3$) δ 8.81 (s, 1H), 8.23-8.11 (m, 3H), 7.84-7.82 (m, 1H), 7.66-7.62 (m, 1H), 6.87 (s, 1H), 4.81 (br s, 1H), 4.10-3.81 (m, 7H), 3.17-3.07 (m, 2H), 2.68-2.45 (m, 1H), 2.13-1.90 (m, 3H), 1.50-1.46 (m, 2H), 1.08-1.05 (m, 3H), 0.89-0.86 (m, 6H). |

-continued

| Ex. | Structure | Name/Characterization |
|---|---|---|
| 7 | 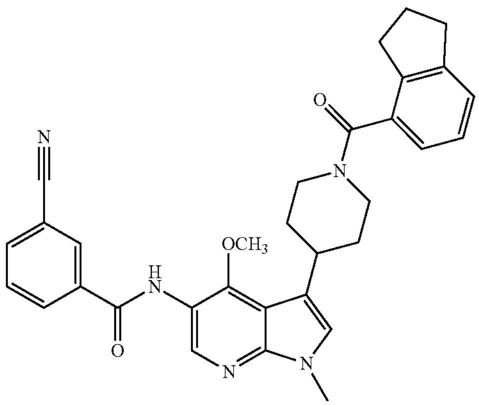 [SMILES: COc1c(NC(=O)c2cccc(C#N)c2)cnc2c1c(C1CCN(C(=O)c3cccc4c3CCC4)CC1)cn2C] | 3-cyano-N-(3-(1-(2,3-dihydro-1H-indene-4-carbonyl)piperidin-4-yl)-4-methoxy-1-methyl-1H-pyrrolo[2,3-b]pyridin-5-yl)benzamide. LC/MS [M + H]; 533.9; $^1$H NMR (400 MHz, DMSO-d$_6$) δ 10.29 (s, 1H), 8.47 (s, 1H), 8.34-8.32 (m, 1H), 8.10-8.09 (m, 2H), 7.80-7.76 (m, 1H), 7.28 (m, 2H), 7.21-7.05 (m, 2H), 4.68-4.65 (m, 1H), 3.93 (s, 3H), 3.76 (s, 3H), 3.53-3.50 (m, 1H), 3.17 (br s, 3H), 2.92-2.81 (m, 5H), 2.06-1.90 (m, 4H), 1.58-1.49 (m, 2H |
| 8 | 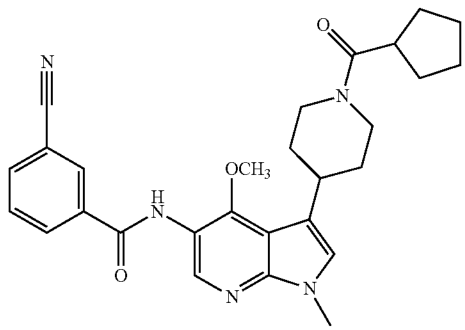 [SMILES: COc1c(NC(=O)c2cccc(C#N)c2)cnc2c1c(C1CCN(C(=O)C3CCCC3)CC1)cn2C] | 3-cyano-N-(3-(1-(cyclopentanecarbonyl)piperidin-4-yl)-4-methoxy-1-methyl-1H-pyrrolo[2,3-b]pyridin-5-yl)benzamide. LC/MS [M + H]: 486.1; $^1$H NMR (400 MHz, CDCl$_3$) δ 8.87 (s, 1H), 8.26 (s, 1H), 8.22-8.20 (m, 1H), 8.13 (s, 1H), 7.88-7.86 (m, 1H), 7.69-7.65 (m, 1H), 6.88 (s, 1H), 4.81-4.76 (m, 1H), 4.12-4.09 (m, 1H), 3.98 (s, 3H), 3.84 (s, 3H), 3.21-3.08 (m, 3H), 2.96-2.92 (m, 1H), 2.70-2.68 (m, 1H), 2.19-2.09 (m, 2H), 1.83-1.52 (m, 10 H). |
| 9 | 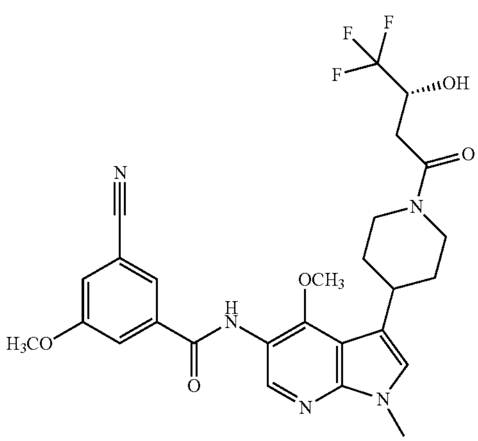 [SMILES: COc1cc(C#N)cc(C(=O)Nc2cnc3c(c(C4CCN(C(=O)C[C@@H](O)C(F)(F)F)CC4)cn3C)c2OC)c1] | (R)-3-cyano-5-methoxy-N-(4-methoxy-1-methyl-3-(1-(4,4,4-trifluoro-3-hydroxybutanoyl)piperidin-4-yl)-1H-pyrrolo[2,3-b]pyridin-5-yl)benzamide. LC/MS [M + H]: 560.1 |
| 10 | 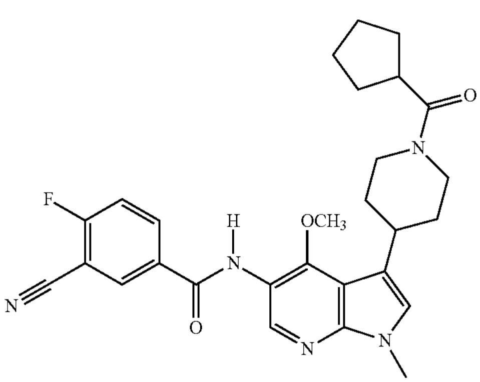 [SMILES: COc1c(NC(=O)c2ccc(F)c(C#N)c2)cnc2c1c(C1CCN(C(=O)C3CCCC3)CC1)cn2C] | 3-cyano-N-(3-(1-(cyclopentanecarbonyl)piperidin-4-yl)-4-methoxy-1-methyl-1H-pyrrolo[2,3-b]pyridin-5-yl)-4-fluorobenzamide. LC/MS [M + H]: 504.3; $^1$H NMR (400 MHz, CDCl$_3$) δ 8.86 (s, 1H), 8.26 (br s, 1H), 8.05 (s, 1H), 7.42-7.40 (m, 1H), 6.90 (s, 1H), 4.82-4.79 (m, 1H), 4.13-4.10 (m, 1H), 3.98 (s, 3H), 3.84 (s, 3H), 3.22-3.11 (m, 2H), 2.97-2.93 (m, 1H), 2.73-2.68 (m, 1H), 2.18-2.10 (m, 2H), 1.84-1.51 (m, 10H). |

| Ex. | Structure | Name/Characterization |
|---|---|---|
| 11 | 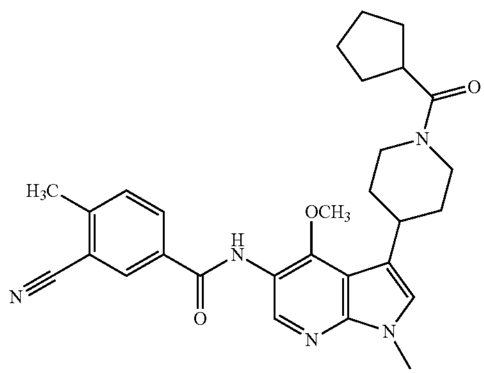 [SMILES: COc1c(NC(=O)c2ccc(C)c(C#N)c2)cnc2c1c(C1CCN(C(=O)C3CCCC3)CC1)cn2C] | 3-cyano-N-(3-(1-(cyclopentanecarbonyl)piperidin-4-yl)-4-methoxy-1-methyl-1H-pyrrolo[2,3-b]pyridin-5-yl)-4-methylbenzamide. LC/MS [M + Na]: 522.2; $^1$H NMR (400 MHz, CDCl) δ 8.85 (s, 1H), 8.20 (s, 1H), 8.08 (s, 1H), 7.50-7.48 (m, 1H), 6.88 (s, 1H), 4.81-4.78 (m, 1H), 4.12-4.09 (m, 1H), 3.97 (s, 3H), 3.83 (s, 3H), 3.21-3.11 (m, 2H), 2.96-2.94 (m, 1H), 2.69-2.65 (m, 4H), 2.19-2.09 (m, 2H), 1.84-1.50 (m, 11H). |
| 12 | 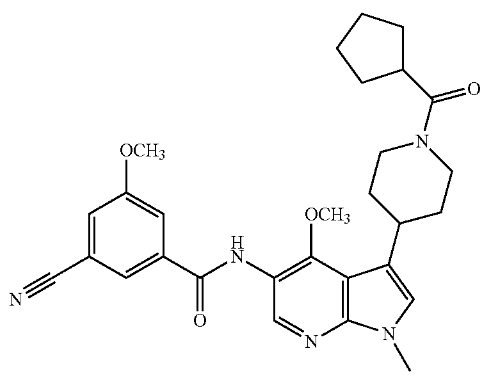 [SMILES: COc1cc(C#N)cc(C(=O)Nc2cnc3c(c(C4CCN(C(=O)C5CCCC5)CC4)cn3C)c2OC)c1] | 3-cyano-N-(3-(1-(cyclopentanecarbonyl)piperidin-4-yl)-4-methoxy-1-methyl-1H-pyrrolo[2,3-b]pyridin-5-yl)-5-methoxybenzamide. LC/MS [M + Na]: 538.3; $^1$H NMR (400 MHz, CDCl$_3$) δ 8.93 (s, 1H), 7.95 (s, 1H), 7.75 (s, 1H), 7.36 (s, 1H), 6.90 (s, 1H), 4.84-4.81 (m, 1H), 4.10-4.00 (m, 1H), 3.99 (s, 3H), 3.94 (s, 3H), 3.85 (s, 3H), 3.16-3.13 (m, 2H), 2.97-2.95 (m, 1H), 2.72-2.70 (m, 1H), 2.20-2.15 (m, 2H), 1.87-1.54 (m, 10H). |
| 13 | 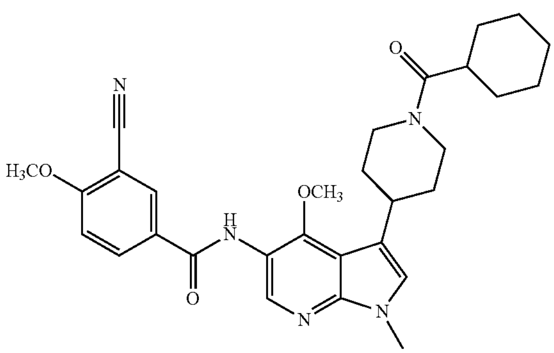 [SMILES: COc1ccc(C(=O)Nc2cnc3c(c(C4CCN(C(=O)C5CCCCC5)CC4)cn3C)c2OC)cc1C#N] | 3-cyano-N-(3-(1-(cyclohexanecarbonyl)piperidin-4-yl)-4-methoxy-1-methyl-1H-pyrrolo[2,3-b]pyridin-5-yl)-4-methoxybenzamide. LC/MS [M + H]: 530.0; $^1$H NMR (400 MHz, DMSO-d$_6$) δ 10.12 (s, 1H), 8.42 (s, 1H), 8.35-8.32 (m, 1H), 8.06 (s, 1H), 7.44-7.42 (s, 1H), 7.24 (s, 1H), 4.56-4.53 (m, 1H), 4.07-4.02 (m, 4H), 3.90 (s, 3H), 3.74 (s, 3H), 3.14-3.12 (m, 3H), 2.61-2.50 (m, 2H), 2.05-1.95 (m, 2H), 1.71-1.15 (m, 12H). |
| 14 | 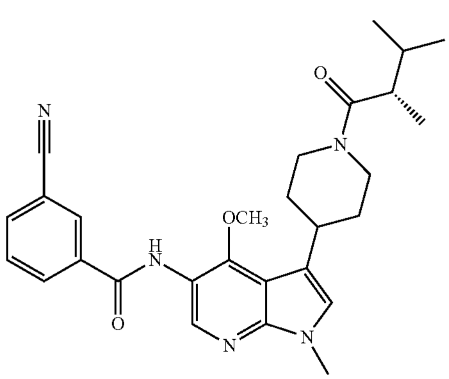 [SMILES: COc1c(NC(=O)c2cccc(C#N)c2)cnc2c1c(C1CCN(C(=O)[C@@H](C)C(C)C)CC1)cn2C] | (S)-3-cyano-N-(3-(1-(2,3-dimethylbutanoyl)piperidin-4-yl)-4-methoxy-1-methyl-1H-pyrrolo[2,3-b]pyridin-5-yl)benzamide. LC/MS [M + H]: 488.2; Chiral LC: Rt = 5.51 min (Method A); $^1$H NMR (400 MHz, CDCl$_3$): δ 8.90 (s, 1H), 8.26 (s, 1H), 8.21-8.19 (m, 1H), 8.06 (s, 1H), 7.88-7.86 (m, 1H), 7.69-7.66 (m, 1H), 6.90 (s, 1H), 4.88-4.84 (m, 1H), 4.14-4.11 (m, 1H), 3.99 (s, 3H), 3.84 (s, 3H), 3.21-3.12 (m, 2H), 2.75-2.71 (m, 1H), 2.69-2.47 (m, 1H), 2.18-1.94 (m, 3H), 1.63-0.90 (m, 10H). |

| Ex. | Structure | Name/Characterization |
|---|---|---|
| 15 | 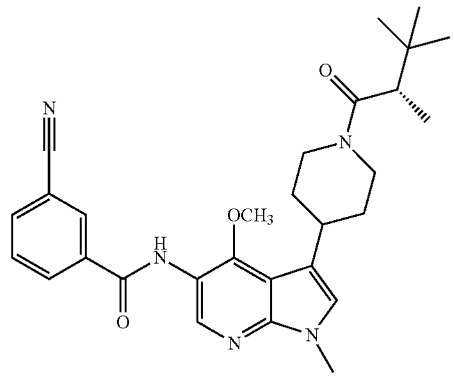 [SMILES: COc1c(NC(=O)c2cccc(C#N)c2)cnc2c1c(C1CCN(C(=O)[C@@H](C)C(C)(C)C)CC1)cn2C] | (S)-3-cyano-N-(4-methoxy-1-methyl-3-(1-(2,3,3-trimethylbutanoyl)piperidin-4-yl)-1H-pyrrolo[2,3-b]pyridin-5-yl)benzamide. LC/MS [M + H]: 502.1; Chiral LC: Rt = 5.85 min (Method B); $^1$H NMR (400 MHz, CDCl$_3$): δ 8.87-8.83 (m, 1H), 8.28-8.16 (m, 3H), 7.88-7.86 (m, 1H), 7.69-7.65 (m, 1H), 6.89-6.86 (m, 1H), 4.90-4.84 (m, 1H), 4.23-4.20 (m, 1H), 3.99 (s, 3H), 3.84 (s, 3H), 3.23-3.08 (m, 2H), 2.73-7.67 (m, 2H), 2.18-2.08 (m, 2H), 1.54-1.44 (m, 2H), 1.13-1.10 (m, 3H), 1.01-0.99 (m, 9H). |
| 16 | 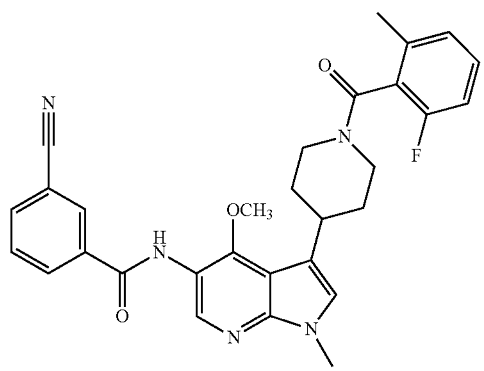 [SMILES: COc1c(NC(=O)c2cccc(C#N)c2)cnc2c1c(C1CCN(C(=O)c3c(C)cccc3F)CC1)cn2C] | 3-cyano-N-(3-(1-(2-fluoro-6-methylbenzoyl)piperidin-4-yl)-4-methoxy-1-methyl-1H-pyrrolo[2,3-b]pyridin-5-yl)benzamide. LC/MS [M]: 526.1; $^1$H NMR (400 MHz, DMSO-d$_6$): δ 10.27 (s, 1H), 8.46 (s, 1H), 8.33-8.31 (m, 1H), 8.10-8.08 (m, 2H), 7.79-7.75 (m, 1H), 7.34-7.31 (m, 1H), 7.26 (s, 1H), 7.16-7.10 (m, 2H), 4.73-4.69 (m, 1H), 3.92 (s, 3H), 3.75 (s, 3H), 3.32-3.18 (m, 3H), 2.97-2.91 (m, 1H), 2.33-2.21 (m, 3H), 2.15-2.08 (m, 1H), 2.00-1.92 (m, 1H), 1.56-1.45 (m, 2H). |
| 17 | 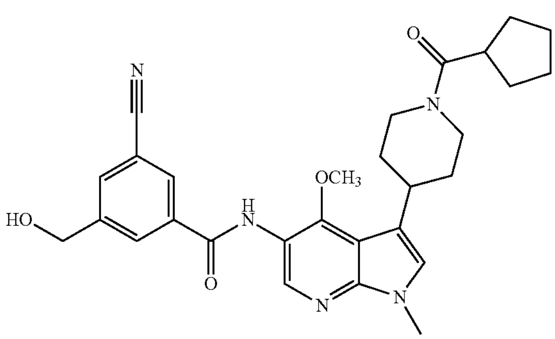 [SMILES: COc1c(NC(=O)c2cc(C#N)cc(CO)c2)cnc2c1c(C1CCN(C(=O)C3CCCC3)CC1)cn2C] | 3-cyano-N-(3-(1-(cyclopentanecarbonyl)piperidin-4-yl)-4-methoxy-1-methyl-1H-pyrrolo[2,3-b]pyridin-5-yl)-5-(hydroxymethyl)benzamide. LC/MS [M + H]: 516.2; $^1$H NMR (400 MHz, CDCl$_3$): δ 8.68 (s, 1H), 8.40 (s, 1H), 8.20 (s, 1H), 8.12 (s, 1H), 7.83 (s, 1H), 6.86 (s, 1H), 4.82 (s, 2H), 4.75-4.72 (m, 1H), 4.11-1.08 (m, 1H), 3.96 (s, 3H), 3.81 (s, 3H), 3.20-3.09 (m, 2H), 2.96-2.91 (m, 1H), 2.70-2.60 (m, 1H), 2.14-2.04 (m, 1H), 1.84-1.80 (m, 1H), 1.72-1.46 (m, 11H). |

Example 18

Preparation of (R)-3-cyano-N-(4-methoxy-1-methyl-3-(1-(2,3,3-trimethylbutanoyl)piperidin-4-yl)-1H-pyrrolo[2,3-b]pyridin-5-yl)-4-(methylthio)benzamide

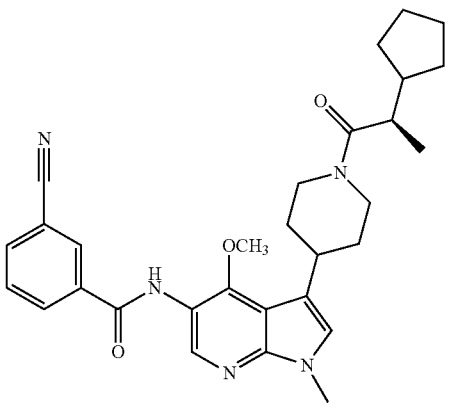 [SMILES: COc1c(NC(=O)c2cccc(C#N)c2)cnc2c1c(C1CCN(C(=O)[C@H](C)C3CCCC3)CC1)cn2C]

Step 1: (R)-3-(2-cyclopentylacetyl)-4-isopropyloxazolidin-2-one. To a solution of (R)-benzyl oxazolidinone (2.0 g, 10 mmol) in THF (55 mL) at −78° C. was added dropwise n-BuLi (2.5 M in hexanes, 4.92 mL, 12.3 mmol). The resulting solution was allowed to stir at the same temperature for 1 h, then cyclopentyl acetyl chloride (1.86 g, 12.3 mmol) was added. The reaction turned pale yellow rapidly and was allowed to stir at −78° C. for 1 h. The reaction was quenched with sat. NaHCO$_3$ solution, extracted with EtOAc, dried over Na$_2$SO$_4$, filtered and concentrated to afford the title compound (3.20 g, 99%) as a pale yellow oil that solidified on standing. $^1$H NMR (400 MHz, CDCl$_3$) δ 7.40-7.28 (m, 3H), 7.26-7.16 (m, 2H), 4.74-4.64 (m, 1H), 4.24-4.12 (m, 2H), 3.32 (dd, J=13, 3 Hz, 1H), 3.04 (dd, J=17, 7 Hz, 1H), 2.92 (dd, J=17, 7 Hz, 1H), 2.77 (dd, J=14, 10 Hz, 1H), 2.41-2.28 (m, 1H), 1.95-1.84 (m, 2H), 1.72-1.56 (m, 4H), 1.30-1.15 (m, 2H).

Step 2: (R)-3-((R)-2-cyclopentylpropanoyl)-4-isopropyloxazolidin-2-one. To a colorless solution of (R)-3-(2-cyclopentylacetyl)-4-isopropyloxazolidin-2-one (3250 mg, 11.34 mmol) in THF (50 mL) at −78° C. was added dropwise LDA (2.0 M, 6.50 mL, 13.0 mmol). The resulting yellow solution was allowed to stir at the same temperature for 1 h. MeI (3.55 mL, 56.6 mmol) was added and the reaction was allowed to warm to 0° C. over 1 h and allowed to stir at 0° C. for 3 h. The reaction was quenched with sat NH$_4$Cl and extracted with EtOAc. The combined organic extracts were washed with sat. NaHCO$_3$ and brine, dried over magnesium sulfate, filtered and concentrated in vacuo to afford a white solid. The crude product was purified by silica gel column chromatography twice (EtOAc:Heptane, 5:95-60:40 then 5:95-50:50). The product was recrystallized from n-heptane to provide the title compound (680 mg, 20%) as colorless crystalline needles. $^1$H NMR (400 MHz, CDCl$_3$) δ 7.40-7.17 (m, 5H), 4.69 (ddt, J=10, 7, 3 Hz, 1H), 4.25-4.11 (m, 2H), 3.63 (dg, J=9, 7 Hz, 1H), 3.28 (dd, J=14, 3 Hz, 1H), 2.78 (dd, J=13, 9 Hz, 1H), 2.21-2.08 (m, 1H), 1.90-1.73 (m, 2H), 1.71-1.48 (m, 4H), 1.30-1.17 (m, 4H), 1.11 (ddd, J=12.0, 5.0, 4.0 Hz, 1H).

Step 3: (R)-2-cyclopentylpropanoic acid. To a solution of (R)-3-((R)-2-cyclopentylpropanoyl)-4-isopropyloxazolidin-2-one (680 mg, 2.26 mmol) in THF/H$_2$O (v/v=1/1, 12 mL) at room temperature was added LiOH-H$_2$O (142 mg, 3.38 mmol) followed by H$_2$O$_2$ (237 mL, 4.17 mmol, 50 wt %). The resulting solution was allowed to stir at room temperature overnight. The reaction was quenched with 1.0 M KHSO$_4$ (8 mL) and extracted with EtOAc (3×). The combined organic extracts were washed with brine and dried over Na$_2$SO$_4$, filtered and concentrated. The crude product was purified by silica gel column chromatography (EtOAc:Heptane, 7:93-50:50) to afford the title compound (285 mg, 89%) as a colorless oil. $^1$H NMR (400 MHz, CDCl$_3$) δ 2.29 (dq, J=9, 7 Hz, 1H), 2.07-1.95 (m, 1H), 1.87-1.76 (m, 2H), 1.69-1.51 (m, 4H), 1.31-1.24 (m, 1H), 1.24-1.15 (m, 4H).

Step 4. (R)-3-cyano-N-(3-(1-(2-cyclopentylpropanoyl)piperidin-4-yl)-4-methoxy-1-methyl-1H-pyrrolo[2,3-b]pyridin-5-yl)benzamide. To the stirred solution of 3-cyano-N-(4-methoxy-1-methyl-3-(piperidin-4-yl)-1H-pyrrolo[2,3-b]pyridin-5-yl)benzamide (for preparation, see Example 1, Step 9: 100 mg, 0.257 mmol) in DCM (3 mL) was added (R)-2-cyclopentylpropanoic acid (54.8 mg, 0.368 mmol), HATU (117 mg, 0.308 mmol), DIPEA (66.4 mg, 0.514 mmol) at 25° C. After 1 hr, LCMS showed the reaction was complete, water (5 mL) was added and the mixture was extracted with DCM (10 mL×3), the organic layer was separated, dried (Na$_2$SO$_4$) and solvent removed to give crude product which was purified by prep. HPLC. (Column: Agela durashell C18 25*21.2, 10 μm; Mobile phase: 41%-61% MeCN/H$_2$O over 10 min, FA 0.225%; Flow rate: 30 mL/min) to give the title compound (18, 53 mg, 40%) as a white solid. LC/MS: (M+H)=514.2; Chiral LC: Rt=15.36 min (Method Q); $^1$H NMR (400 MHz, CDCl$_3$) δ, ppm 8.90 (br. s., 1 H), 8.14-8.33 (m, 2 H), 8.05 (br. s., 1 H), 7.88 (d, J=7.53 Hz, 1 H), 7.68 (t, J=7.53 Hz, 1 H), 6.90 (br. s., 1 H), 4.85 (d, J=11.54 Hz, 1 H), 4.15 (d, J=12.05 Hz, 1 H), 3.99 (s, 3 H), 3.85 (s, 3 H), 3.01-3.27 (m, 1 H), 2.45-2.76 (m, 1 H) 2.02-2.31 (m, 3 H), 1.89-1.79 (m, 1 H), 1.72-1.45 (m, 9 H), 0.92-1.31 (m, 5 H).

Example 19

The following Example 19 was prepared analogous to Example 18 employing the appropriate enantiomer carboxylic acid preparation in steps 1-3.

| Ex. | Structure | Name/Characterization |
|---|---|---|
| 19 | 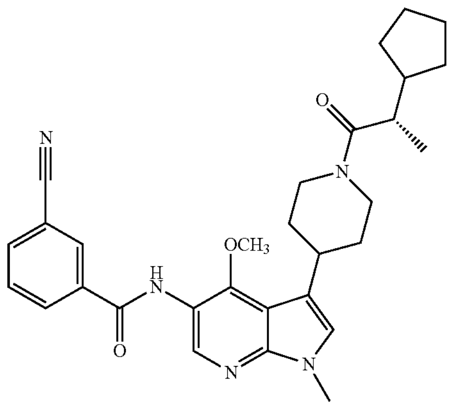 [SMILES: COc1c(NC(=O)c2cccc(C#N)c2)cnc2c1c(C1CCN(C(=O)[C@@H](C)C3CCCC3)CC1)cn2C] | (S)-3-cyano-N-(3-(1-(2-cyclopentylpropanoyl)piperidin-4-yl)-4-methoxy-1-methyl-1H-pyrrolo[2,3-b]pyridin-5-yl)benzamide. LC/MS [M + H]: 514.2; Chiral LC: Rt = 4.29 min (Method Q); ¹H NMR (400 MHz, CDCl₃) δ 8.84 (s, 1H), 8.26-8.20 (m, 3H), 7.88-7.86 (m, 1H), 7.69-7.66 (m, 1H), 6.90-6.89 (m, 1H), 4.86-4.82 (m, 1H), 4.16-4.03 (m, 1H), 3.99 (s, 3H), 3.84 (s, 3H), 3.21-3.10 (m, 2H), 2.70-2.53 (m, 2H), 2.21-2.11 (m, 3H), 1.82-1.50 (m, 18H), 1.16-1.03 (m, 5H). |

Example 20

Preparation 3-cyano-N-(3-(3-isobutyryl-3-azabicyclo[3.2.1]octan-8-yl)-4-methoxy-1-methyl-1H-pyrrolo[2,3-b]pyridin-5-yl)benzamide

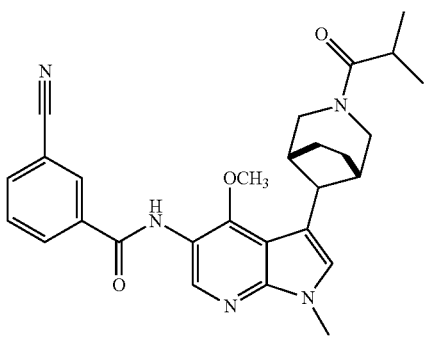

Step 1: tert-butyl 8-oxo-3-azabicyclo[3.2.1]octane-3-carboxylate. Di-tert-butyl dicarbonate (5.81 g, 26.6 mmol) and Pearlman's catalyst (1.55 g, 23.2 mmol) were successively added to a solution of 3-benzyl-3-azabicyclo[3.2.1]octan-8-one obtained from commercial sources (Reference Mityuk, et al, Synthesis, 2010, 493-97, CAS 83507-33-9) (5.0 g, 22.0 mmol) in EtOAc (74 mL) at 25° C. The reaction vessel was alternately filled with nitrogen and evacuated (3×) and then filled and evacuated with hydrogen (2×). The mixture was stirred overnight under 100 psi of H₂. The mixture was filtered through a pad of Celite® which was washed with ethyl acetate. The filtrate was concentrated and the crude product was purified by silica gel chromatography (heptane:EtOAc, 0:100-100:0) to provide the title compound (4.49 g, 90%) as a solid. LC/MS [M-Me]=211.1; ¹H NMR (400 MHz, CDCl₃) δ 4.38 (d, J=14.0 Hz, 1H), 4.20 (d, J=14.0 Hz, 1H), 3.27 (d, J=13.3 Hz, 1H), 3.17 (d, J=13.3 Hz, 1H), 2.24 (d, J=15.6 Hz, 2H), 1.76-1.99 (m, 4H), 1.49 (s, 9H).

Step 2: tert-butyl 8-(methoxymethylidene)-3-azabicyclo[3.2.1]octane-3-carboxylate. Potassium tert-butoxide (4.47 g, 39.8 mmol) was added portionwise to a suspension of (methoxymethyl)triphenylphosphonium chloride (12.4 g, 36.1 mmol) and tert-butyl 8-oxo-3-azabicyclo[3.2.1]octane-3-carboxylate (4.49 g, 19.9 mmol) in THF (100 mL) at 0° C. After 45 min, the cold bath was removed and the reaction was stirred overnight at 25° C. The reaction was recooled at 0° C. and a saturated solution of NH₄Cl was added until pH=6. After warming to 25° C., the mixture was diluted with water (50 mL) and extracted with DCM (30 mL×3). The combined organic layers were washed with brine, dried with Na₂SO₄, filtered and concentrated. The resulting oil was diluted with a small amount of ether and a large volume of heptane. After vigorous stirring for 1 h, the resulting solid was filtered off and washed with additional heptane. The filtrate was concentrated and the resulting oil was purified by silica gel chromatography (heptane:EtOAc, 100/0-70/30) to provide the title compound (4.73 g, 94%). LC/MS [M-Me]= 239.1; ¹H NMR (400 MHz, CDCl₃) δ 5.86 (s, 1H), 4.02 (t, J=12.1 Hz, 1H), 3.79-3.94 (m, 1H), 3.57 (s, 3H), 2.76-3.05 (m, 3H), 2.41 (m, 1H), 1.58-1.65 (m, 4H), 1.47 (br s, 9H).

Step 3: tert-butyl (8-anti)-formyl-3-azabicyclo[3.2.1]octane-3-carboxylate. Water (0.473 mL) followed by paratoluenesulfonic acid monohydrate (2.71 g, 13.8 mmol) was added to a solution of tert-butyl 8-(methoxymethylidene)-3-azabicyclo[3.2.1]octane-3-carboxylate (3.33 g, 13.14 mmol) in acetone (87.6 mL) at 0° C. The mixture was stirred at 0° C. for 2 h and was quenched at the same temperature with a saturated solution of NaHCO₃ until pH=8. Acetone was carefully removed under vacuum (bath at 10° C.) and the aqueous layer was extracted with DCM (30 mL×3). The combined organic layers were washed with brine, dried with sodium sulfate, filtered and concentrated to afford a mixture of predominantly undesired diatereomer (10.09 ppm) versus desired aldehyde (9.62 ppm) in a 3:1 ratio. Complete epimerization was obtained after stirring the crude mixture at 25° C. in a mixture of DCM (13.1 mL) and DBU (26.3 mmol, 3.93 mL) for 30 min. EtOAc (100 mL) was added and DCM was carefully evaporated (150 mbar, bath 35° C.) leaving most of the EtOAc in the flask. The reaction was then quenched with a saturated solution of NH₄Cl. The phases were separated and the organic phase was washed with a saturated solution of NH₄Cl followed by brine, dried with Na₂SO₄, filtered and concentrated. The resulting oil was purified by silica gel chromatography (heptane/EtOAc, 100:0-0:100) to afford the title compound (2.41 g, 77%) as a solid. LC/MS [M-Me]=225.0; ¹H NMR (400 MHz, CDCl₃) δ ppm 9.63 (s, 1H), 4.03 (d, J=13.3 Hz, 1H), 3.88 (d, J=13.3 Hz, 1H), 2.87 (m, 2H), 2.50-2.66 (m, 3H), 1.52-1.67 (m, 4H), 1.47 (s, 9H).

Step 4: tert-butyl 8-(1-hydroxy-2-nitroethyl)-3-azabicyclo[3.2.1]octane-3-carboxylate. Nitromethane (815 μL, 15.0 mmol) and potassium tert-butoxide (1 M in THF, 2.0 mL, 2.0 mmol) were successively added to a solution of tert-butyl (8-anti)-formyl-3-azabicyclo-[3.2.1]octane-3-carboxylate (2.40 g, 10.0 mmol) in a mixture of THF:t-BuOH (1:1, 10 mL). The mixture was stirred at 0° C. for 1 h, warmed to 25° C. and stirred overnight. The reaction was quenched with a saturated solution of NH$_4$Cl (10 mL). The phases were separated and the aqueous phase was extracted with DCM (10 mL×3). The combined organic phases were dried over sodium sulfate, filtered and concentrated under vacuum. After drying the crude residue for 1 h under high vacuum, the title compound (3.10 g, 100%) was obtained as a white solid and was used for the next step without purification. LC/MS [M-Me]=286.1: $^1$H NMR (500 MHz, CDCl$_3$) δ ppm 4.55-4.50 (m, 1H), 4.36-4.45 (m, 1H), 3.77-4.04 (m, 3H), 3.33-3.41 (m, 1H), 2.72-2.91 (m, 2H), 2.58-2.68 (m, 1H), 2.46-2.58 (m, 1H), 1.88-2.01 (m, 1H), 1.53-1.82 (m, 4H), 1.47 (br. s, 9H).

Step 5. tert-butyl (E)-8-(2-nitrovinyl)-3-azabicyclo[3.2.1]octane-3-carboxylate. TEA (8.56 mmol, 1.19 mL) was added to a solution of tert-butyl (8-anti)-(1-hydroxy-2-nitroethyl)-3-azabicyclo[3.2.1]octane-3-carboxylate (1.28 g, 4.28 mmol) in DCM (5.48 mL) at 0° C. Methanesulfonyl chloride (4.71 mmol, 0.367 mL) was then slowly added. After stirring for 10 min at 0° C., the mixture was quenched with water (5 mL). The layers were separated and the organic phase was washed with a saturated aqueous of NH$_4$Cl (5 mL) and then filtered through a plug of florisil eluting with additional DCM. The filtrate was dried with sodium sulfate, filtered and concentrated to afford the title compound (1.11 g, 92%) as a colorless oil. LC/MS [M-Me]=268.1; $^1$H NMR (500 MHz, CDCl$_3$) δ 7.14 (dd, J=13.4, 7.8 Hz, 1H), 7.02 (dd, J=13.4, 1.2 Hz, 1H), 4.01 (d, J=13.0 Hz, 1H), 3.87 (d, J=12.5 Hz, 1H), 2.95 (d, J=13.2 Hz, 1H), 2.86 (d, J=12.5 Hz, 1H), 2.53 (d, J=7.8 Hz, 1H), 2.23-2.28 (m, 1H), 2.17-2.22 (m, 1H), 1.75-1.82 (m, 2H), 1.55-1.72 (m, 2H), 1.47 (s, 9H).

Step 6. tert-butyl (8-anti)-[1-(4-bromo-2-fluoropyridin-3-yl)-2-nitroethyl]-3-azabicyclo[3.2.1]octane-3-carboxylate. At −78° C., to a solution of lithium diisopropylamide (2 M in THF/heptane/ethylbenzyne, 4.29 mmol, 2.14 mL) in THF (4.29 mL) was slowly added 4-bromo-2-fluoropyridine (4.29 mmol, 0.455 mL). The mixture was stirred 1 h at −78° C. and tert-butyl (E)-8-(2-nitrovinyl)-3-azabicyclo[3.2.1]octane-3-carboxylate (1.09 g, 3.86 mmol) in THF (4.29 mL) was slowly added. The mixture was stirred 30 min at −78° C. then the cold bath was removed and the reaction was stirred until it reached room temperature. The reaction mixture was quenched with a saturated solution of NH$_4$Cl (5 mL). The aqueous phase was extracted several times with DCM (5 mL) and the combined organic phases were washed with brine, dried over sodium sulfate, filtered, and evaporated. Purification by flash chromatography (heptane/AcOEt, 100/0 to 40/60) provided the title compound (912 mg, 52% yield) as a yellow solid: LC/MS [M-Me+H]= 445.0; $^1$H NMR (400 MHz, CDCl$_3$) δ ppm 7.98 (d, J=5.3 Hz, 1H), 7.45 (d, J=5.1 Hz, 1H), 4.67-4.85 (m, 2H), 4.04 (d, J=14.0 Hz, 0.5 H), 3.81-3.95 (m, 3H), 3.72 (d, J=12.9 Hz, 0.5 H), 2.66-2.96 (m, 2H), 2.11-2.28 (m, 2H), 1.80-2.02 (m, 2H), 1.71 (m, 2H), 1.45 (br. s., 9H).

Step 7. (8-anti)-[1-(4-bromo-2-fluoropyridin-3-yl)-2-nitroethyl]-3-azabicyclo[3.2.1]octane-3-carboxylate. At 25° C., to a solution of tert-butyl (8-anti)-[1-(4-bromo-2-fluoropyridin-3-yl)-2-nitroethyl]-3-azabicyclo[3.2.1]octane-3-carboxylate (912.0 mg, 1.99 mmol) in DCM (6.63 mL) was slowly added HCl (4M in dioxane, 4.97 mL, 19.9 mmol). The reaction was stirred for 1 h at 50° C. The solvent was directly removed under reduced pressure, providing hydrochloride salt of the title compound (785 mg, 100%) which was dried over 1 h under high and was directly use for the next step without purification: LC/MS [M+H]=358.0; $^1$H NMR (400 MHz, CD$_3$OD) δ ppm 8.03 (d, J=5.5 Hz, 1 H), 7.62 (d, J=5.5 Hz, 1 H), 5.01 (dd, J=12.9, 4.7 Hz, 1 H), 4.85-4.95 (m, 2 H), 3.98 (td, J=10.1, 4.7 Hz, 1 H), 3.20-3.29 (m, 2 H), 3.03-3.16 (m, 2 H), 2.54-2.59 (m, 1 H), 2.45-2.51 (m, 1 H), 2.12-2.33 (m, 2 H), 1.82-1.92 (m, 1 H), 1.70-1.82 (m, 2 H).

Step 8. 1-{(8-anti)-[1-(4-bromo-2-fluoropyridin-3-yl)-2-nitroethyl]-3-azabicyclo[3.2.1]oct-3-yl}-2-methylpropan-1-one. At room temperature, to a solution of hydrochloride salt of tert-butyl (8-anti)-[1-(4-bromo-2-fluoropyridin-3-yl)-2-nitroethyl]-3-azabicyclo[3.2.1]octane-3-carboxylate (785 mg, 1.99 mmol) in DCM (6.63 mL) and was added a saturated solution of NaHCO$_3$ (18.0 mL). The mixture was stirred vigorously and isobutyryl chloride (230 uL, 2.19 mmol) was slowly added. After 10 min, the reaction was transferred in a separating funnel and the phases were separated. The aqueous layer was extracted twice with DCM (5 mL) and the combined organic phases were dried with sodium sulfate, filtered, and evaporated providing the title compound (819 mg, 97% yield) which was used for the next step without purification. LC/MS [M+H]=428.0; (Note: $^1$H NMR complex due to the presence of rotamers and diastereomers): $^1$H NMR (400 MHz, CDCl$_3$) δ ppm 7.99 (d, J=5.1 Hz, 1 H), 7.46 (d, J=5.1 Hz, 1 H), 4.69-4.86 (m, 2 H), 4.49 (d, J=13.7 Hz, 0.5 H), 4.32 (d, J=13.7 Hz, 0.5 H), 3.93 (t, J=11.1 Hz, 1 H), 3.81 (d, J=12.9 Hz, 0.5 H), 3.64 (d, J=11.7 Hz, 0.5 H), 3.21 (d, J=11.9 Hz, 0.5 H), 3.08 (d, J=12.9 Hz, 0.5 H), 2.66-2.84 (m, 1.5 H), 2.57 (d, J=13.3 Hz, 0.5 H), 2.32-2.21 (m, 2 H), 2.03-1.78 (m, 2 H), 1.75-1.43 (m, 4 H), 1.20-1.02 (m, 6 H).

Step 9. 1-[(8-anti)-(4-bromo-2,3-dihydro-1H-pyrrolo[2,3-b]pyridin-3-yl)-3-azabicyclo[3.2.1]oct-3-yl]-2-methylpropan-1-one. At room temperature, to a solution of 1-{(8-anti)-[1-(4-bromo-2-fluoropyridin-3-yl)-2-nitroethyl]-3-azabicyclo[3.2.1]oct-3-yl}-2-methylpropan-1-one (819 mg, 1.94 mmol) in THF (3.87 mL) were successively added AcOH (1.11 mL, 19.4 mmol) and zinc powder (1.27 g, 19.4 mmol). The solution was stirred overnight at room temperature. The reaction was filtered through a plug of Celite® and rinsed with DCM. The organic layer was evaporated under vacuum providing a yellow gum. Purification by flash chromatography (DCM/MeOH, 100/0 to 85/15) gave the title compound (268 mg, 37% yield) as a white powder which was immediately carried forward in the sequence without further purification or characterization.

Step 10. 1-[(8-anti)-(4-bromo-1-methyl-2,3-dihydro-1H-pyrrolo[2,3-b]pyridin-3-yl)-3-azabicyclo[3.2.1]oct-3-yl]-2-methylpropan-1-one. At room temperature, to a solution of 1-[(8-anti)-(4-bromo-2,3-dihydro-1H-pyrrolo[2,3-b]pyridin-3-yl)-3-azabicyclo[3.2.1]oct-3-yl]-2-methylpropan-1-one (268 mg, 0.708 mmol) in THF (2.36 mL) was added in one portion NaH (60% in oil, 57 mg, 1.42 mmol) followed by methyl iodide (49 uL, 0.78 mmol). The reaction was stirred for 2 h and was quenched with a saturated solution of NH$_4$Cl (5 mL) and diluted with DCM (5 mL). The phases were separated and the aqueous layer was extracted twice with DCM (5 mL). The combined organic phases were dried over Na$_2$SO$_4$, filtered and evaporated. Purification by flash chromatography (heptane/EtOAc, 10010 to 0/100) gave the title compound (123 mg, 44% yield) as a colorless oil: LC/MS [M+H]=392.1; $^1$H NMR (400 MHz, CDCl$_3$) δ ppm 7.73 (d, J=5.9 Hz, 1 H), 6.68-6.60 (m, 1 H), 4.49-4.41 (m, 0.6 H), 4.39-4.31 (m, 0.4 H), 3.82-3.74 (m, 0.4 H), 3.73-3.65

(m, 0.6 H), 3.47-3.30 (m, 2 H), 3.18 (d, J=12.1 Hz, 0.6 H), 3.03-2.74 (m, 5.4 H), 2.69 (d, J=12.5 Hz, 0.6 H), 2.52 (d, J=13.3 Hz, 0.4 H), 2.38-2.11 (m, 3 H), 1.97-1.74 (m, 2 H), 1.71-1.41 (m, 2 H), 1.21-1.02 (m, 6 H).

Step 11. 1-[(8-anti)-8-(4-bromo-1-methyl-5-nitro-1H-pyrrolo[2,3-b]pyridin-3-yl)-3-azabicyclo[3.2.1]oct-3-yl]-2-methylpropan-1-one At 0° C., to a solution of 1-[(8-anti)-(4-bromo-1-methyl-2,3-dihydro-1H-pyrrolo[2,3-b]pyridin-3-yl)-3-azabicyclo[3.2.1]oct-3-yl]-2-methylpropan-1-one (123 mg, 0.313 mmol) in DCM (2.08 mL) were successively added trifluoroacetic acid (72 uL, 0.94 mmol), followed by tetramethylammonium nitrate (128 mg, 0.94 mmol) and trifluoroacetic anhydride (131 uL, 0.94 mmol). The reaction was stirred 1 h at 0° C. and 3 h at room temperature. The mixture was neutralized with a saturated solution of NaHCO₃ until pH=8. The phases were separated and the aqueous layer was extracted three times with DCM (5 mL). The combined organic layers were dried with Na₂SO₄, filtered, and evaporated under reduced pressure affording the title compound (135 mg, 99% yield) as a yellow powder which was used immediately for the next step without any further purification or characterization.

Step 12. 1-[(8-anti)-8-(4-methoxy-1-methyl-5-nitro-1H-pyrrolo[2,3-b]pyridin-3-yl)-3-azabicyclo[3.2.1]oct-3-yl]-2-methylpropan-1-one. At room temperature, to a solution of 1-[(8-anti)-8-(4-bromo-1-methyl-5-nitro-1H-pyrrolo[2,3-b]pyridin-3-yl)-3-azabicyclo[3.2.1]oct-3-yl]-2-methylpropan-1-one (38.0 mg, 0.087 mmol) in THF (0.582 mL) was added sodium methoxide (1 M in MeOH, 0.105 mmol, 0.105 mL). The reaction was stirred 1 h at rt. The mixture was then treated with a saturated solution of NH₄Cl until pH=6. The phases were separated and the aqueous layer was extracted 3 times with DCM (5 mL). The combined organic phases were dried over Na₂SO₄, filtered, and evaporated. Purification by flash chromatography (DCM/EtOAc, 100/0 to 0/100) provided the title compound (15 mg, 44% yield) as a white powder: LC/MS [M+H]=387.0; $^1$H NMR (400 MHz, CDCl₃) δ ppm 1.14 (d, J=7.0 Hz, 3 H), 1.21 (d, J=7.0 Hz, 3 H), 1.21-1.30 (m, 2 H), 1.79 (m, 2 H), 2.57 (br. s., 2 H), 2.87 (spt, J=7.0 Hz, 1 H), 2.92 (d, J=14.0 Hz, 1 H), 3.32 (s, 1 H), 3.41 (d, J=11.7 Hz, 1 H), 3.86 (m, 1 H), 3.88 (s, 3 H), 4.11 (s, 3 H), 4.53 (d, J=12.9 Hz, 1 H), 6.92 (s, 1 H), 8.91 (s, 1 H).

Step 13. 1-[(8-anti)-8-(5-amino-4-methoxy-1-methyl-1H-pyrrolo[2,3-b]pyridin-3-yl)-3-azabicyclo[3.2.1]oct-3-yl]-2-methylpropan-1-one. At room temperature, to a solution of 1-[(8-anti)-8-(4-methoxy-1-methyl-5-nitro-1H-pyrrolo[2,3-b]pyridin-3-yl)-3-azabicyclo[3.2.1]oct-3-yl]-2-methylpropan-1-one (20 mg, 0.052 mmol) in mixture of methanol/THF (1:1, 1.73 mL) was added a saturated solution of NH₄Cl (0.450 mL) followed by zinc dust (17 mg, 0.259 mmol). The resulting gray mixture was stirred at room temperature for 10 min and was filtered through a fritted plastic funnel and the filter cake was rinsed with DCM and water. The phases were separated and the aqueous layer was extracted three times with DCM (5 mL). The combined organic phases were dried over sodium sulfate, filtered, and concentrated under reduced pressure providing the title compound (18 mg, 90%) which was directly used for the next step without purification: LC/MS [M+H]=357.2.

Step 14. 3-cyano-N-(3-(3-isobutyryl-3-azabicyclo[3.2.1]octan-8-yl)-4-methoxy-1-methyl-1H-pyrrolo[2,3-b]pyridin-5-yl)benzamide. At room temperature, to a solution of crude 1-[(8-anti)-8-(5-amino-4-methoxy-1-methyl-1H-pyrrolo[2,3-b]pyridin-3-yl)-3-azabicyclo[3.2.1]oct-3-yl]-2-methylpropan-1-one (18 mg, 0.050 mmol) in DCM (0.505 mL) were successively added diisopropylethylamine (DIEA, 0.076 mmol, 13.3 uL) and m-cyanobenzoyl chloride (10.9 mg, 0.066 mmol). The reaction was stirred for 30 min and was quenched with a saturated solution of NaHCO₃ (5 mL). The phases were separated and the aqueous layer was extracted three times with DCM (5 mL). The combined organic phases were dried with sodium sulfate, filtered, and concentrated under reduced pressure. Purification by flash chromatography (DCM/EtOAc, 0/100 to 0/100) gave the title compound (16.5 mg, 67% yield over two steps) as a white powder: LC/MS [M+H]=486.2; 1H NMR (400 MHz, CD₃OD-d₄) δ ppm 8.38 (s, 1 H), 8.32 (d, J=8.2 Hz, 1 H), 8.18 (s, 1 H), 7.99 (d, J=9.4 Hz, 1 H), 7.76 (t, J=8.2 Hz, 1 H), 7.12 (s, 1 H), 4.42 (d, J=12.9 Hz, 2 H), 4.05 (s, 3 H), 3.99 (d, J=12.9 Hz, 2 H), 3.81 (s, 3 H), 3.48 (m, 2H), 2.92-3.07 (m, 3 H), 2.59-2.67 (m, 2 H), 1.43-1.60 (m, 4 H), 1.17 (d, J=6.6 Hz, 3 H), 1.09 (d, J=6.6 Hz, 3 H).

Examples 21-23

The following Examples 21-23 were prepared in an analogous manner to Example 20 employing the appropriate carboxylic acid coupling reagent in Step 8.

| Ex. | Structure | Name/Characterization |
|---|---|---|
| 21 | 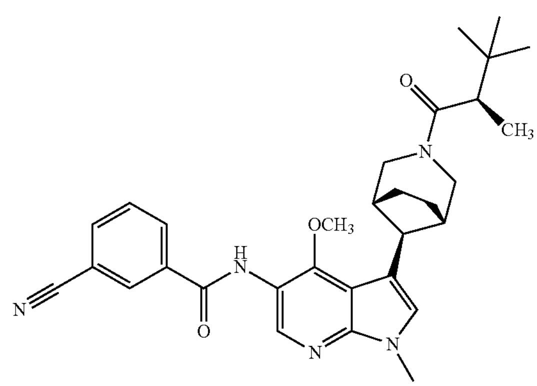 [SMILES: COc1c(NC(=O)c2cccc(C#N)c2)cnc2c1c([C@@H]1[C@@H]3CC[C@H]1CN(C(=O)[C@H](C)C(C)(C)C)C3)cn2C] | 3-cyano-N-(4-methoxy-1-methyl-3-((1R,5S,8R)-3-((R)-2,3,3-trimethylbutanoyl)-3-azabicyclo[3.2.1]octan-8-yl)-1H-pyrrolo[2,3-b]pyridin-5-yl)benzamide; LC/MS [M + H] = 528.3; $^1$H NMR (400 MHz, CD₃OD-d₄) δ ppm 8.37 (s, 1 H), 8.31 (d, J = 8.2 Hz, 1 H), 8.18 (s, 1 H), 7.98 (d, J = 7.8 Hz, 1 H), 7.75 (t, J = 7.6 Hz, 1 H), 7.10 (br. s., 1 H), 4.27-4.59 (m, 1 H), 4.12 (d, J = 12.1 Hz, 1 H), 4.04 (s, 3 H), 3.80 (s, 3 H), 3.34-3.47 (m, 2 H), 2.77-3.00 (m, 3 H), 2.63 (br. s., 2 H), 1.85 (d, J = 5.9 Hz, 2 H), 1.22-1.68 (m, 3 H), 1.13 (d, J = 7.0 Hz, 2 H), 0.91-1.11 (m, 12 H). |

| Ex. | Structure | Name/Characterization |
|---|---|---|
| 22 | 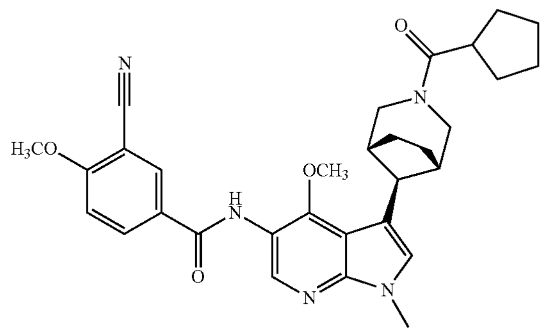 [SMILES: COc1ccc(C(=O)Nc2cnc3c(c([C@@H]4[C@@H]5CC[C@H]4CN(C(=O)C4CCCC4)C5)cn3C)c2OC)cc1C#N] | 3-cyano-N-(3-((1R,5S,8r)-3-(cyclopentanecarbonyl)-3-azabicyclo[3.2.1]octan-8-yl)-4-methoxy-1-methyl-1H-pyrrolo[2,3-b]pyridin-5-yl)-4-methoxybenzamide. LC/MS [M + H]: 542.7; $^1$H NMR (400 MHz, CDCl$_3$): δ 8.88 (br. s., 1 H), 8.14-8.24 (m, 2 H), 8.01 (br. s., 1 H), 7.12 (d, J = 8.59 Hz, 1 H), 6.86 (s, 1 H) 4.50 (d, J = 12.49 Hz, 1 H), 4.02-4.08 (m, 3 H), 3.95-4.02 (m, 3 H), 3.88-3.94 (m, 1 H), 3.80-3.86 (m, 3 H), 3.72-3.78 (m, 1 H), 3.38 (d, J = 12.10 Hz, 1 H), 3.25 (s, 1 H), 2.89-2.99 (m, 2 H), 2.60 (br. s., 2 H), 1.69-1.94 (m, 5 H), 1.51-1.62 (m, 4 H), 1.41-1.51 (m, 2 H). |
| 23 | 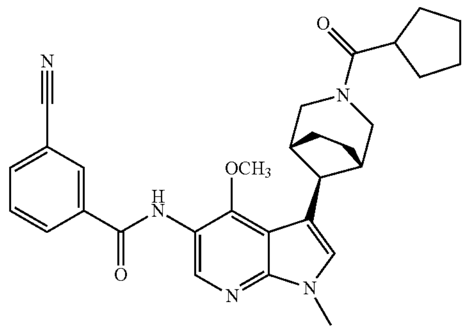 [SMILES: COc1c(NC(=O)c2cccc(C#N)c2)cnc2c1c([C@@H]1[C@@H]3CC[C@H]1CN(C(=O)C1CCCC1)C3)cn2C] | 3-cyano-N-(3-((1R,5S,8r)-3-(cyclopentanecarbonyl)-3-azabicyclo[3.2.1]octan-8-yl)-4-methoxy-1-methyl-1H-pyrrolo[2,3-b]pyridin-5-yl)benzamide. LC/MS [M + H]: 512.4; $^1$H NMR (400 MHz, CDCl$_3$): δ 8.87 (s, 1 H), 8.18-8.31 (m, 3 H), 7.86 (d, J = 7.80 Hz, 1 H), 7.67 (t, J = 7.81 Hz, 1 H), 6.86 (s, 1 H), 4.49 (d, J = 10.93 Hz, 1 H), 3.98-4.04 (m ,3 H), 3.86-3.93 (m, 1 H), 3.84 (s, 3 H), 3.37 (d, J = 12.10 Hz, 1 H), 3.25 (s, 1 H), 2.88-2.97 (m, 2 H), 2.59 (br. s., 2 H), 1.85-1.93 (m, 2 H), 1.48-1.95 (m, 10 H). |

Example 24

Preparation of 3-cyano-N-(3-((3R,4R)-1-(cyclopentanecarbonyl)-3-methylpiperdin-4-yl)-4-methoxy-1-methyl-1H-pyrrolo[2,3-b]pyridin-5-yl)benzamide

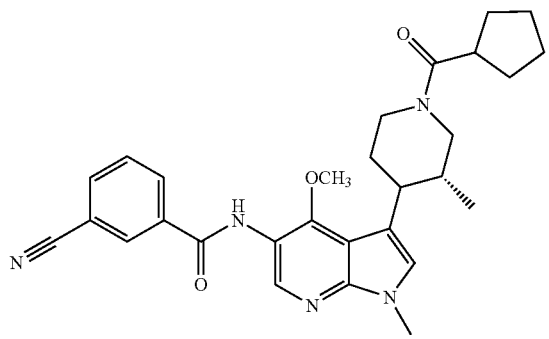 [SMILES: COc1c(NC(=O)c2cccc(C#N)c2)cnc2c1c(C1CCN(C(=O)C3CCCC3)C[C@@H]1C)cn2C]

Step 1. tert-butyl 3-methyl-4-oxopiperidine-1-carboxylate. A mixture of 1-benzyl-3-methylpiperidin-4-one (4.33 g, 21.3 mmol), Pd(OH)$_2$/C (20% on active C, 1.0 g), and di-tert-butyl dicarbonate (5.11 g, 23.4 mmol) in EtOAc (30 mL) was stirred under 50 PSI of H$_2$ over 12 h. Upon completion, the mixture was filtered through Celite®, rinsing with EtOAc (10 mL), and the solvent was evaporated to give the crude product as a colorless oil. The crude was left on under high vac for 12 h to remove any trace di-tert-butyl dicarbonate, and the material was carried forward without any further purification or characterization.

Step 2. tert-butyl 3-methyl-4-(((trifluoromethyl)sulfonyl)oxy)-3,6-dihydropyridine-1(2H)-carboxylate: A solution of diisopropylamine (0.182 mL, 1.3 mmol) in THF (4 mL) was cooled to −78° C. and nBuLi (2.5 M in hexanes, 0.52 mL, 1.3 mmol) was added dropwise. The mixture was stirred at −78° C. for 30 min. Next, a solution of tert-butyl 3-methyl-4-oxopiperidine-1-carboxylate (185 mg, 0.87 mmol) in THF (3 mL) was added slowly to the prepared solution of LDA at −78° C. After 40 min, a solution of N-phenyl bis(trifluoromethanesulfonimide) (PhNHTf) (402.9 mg, 1.13 mmol) in THF (3 mL) was slowly added. After 1.5 h, the cooling bath was removed and reaction mixture was allowed to warm to 25° C. over the course of 1.5 h. Upon completion, the solution was quenched with sat. aq. NaHCO$_3$ (10 mL) and extracted with EtOAc (3×5 mL). The combined organic layers were washed sequentially with 5% citric acid solution (5 mL), brine (5 mL), and then dried with sodium sulfate. Concentration of the organic layer resulted in a brown oily residue which was purified by flash column chromatography (heptane:EtOAc 1:0 to 9:1) to obtain the desired product (198 mg, 66%) as a colorless oil: $^1$H NMR (400 MHz, CDCl$_3$) δ 5.75 (s, 1H), 4.29-3.91 (m, 2H), 3.78-3.26 (m, 2H), 2.65 (s, 1H), 1.49 (s, 9H), 1.21-1.15 (m, 3H).

Step 3. 4-chloro-1-(phenylsulfonyl)-1H-pyrrolo[2,3-b]pyridine: To a solution of 4-chloro-1H-pyrrolo[2,3-b]pyridine (5.78 g, 37.9 mmol) in DCM (291 mL) was added DMAP (463 mg, 3.79 mmol), TEA (7.92 mL, 56.8 mmol), and benzenesulfonyl chloride (5.39 mL, 41.7 mmol) at 25° C. The reaction was allowed to stir for 48 h at 25° C. Upon completion, DCM (300 mL) was added, and the reaction was washed with water (200 mL), 1 N HCl (100 mL), sat. aq. NaHCO3 (200 mL), and brine (300 mL). The organic layer was dried over MgSO$_4$, filtered, concentrated, and triturated with Et$_2$O to afford 4-chloro-1-(phenylsulfonyl)-1H-pyrrolo[2,3-b]pyridine (10.46 g, 94%) as a brown solid. LC/MS [M+H]=293.0; $^1$H NMR (400 MHz, DMSO-d$_6$) δ 8.35-8.34 (m, 1H), 8.13-8.11 (m, 2H), 8.05-8.04 (m, 1H), 7.76-7.72 (m, 1H), 7.65-7.61 (m, 2H), 7.47-7.46 (m, 1H), 6.89-6.88 (m, 1H).

Step 4. 4-chloro-5-nitro-1H-pyrrolo[2,3-b]pyridine: To a solution of 4-chloro-5-nitro-1-(phenylsulfonyl)-1H-pyrrolo[2,3-b]pyridine (prepared as described in example 1) (1.70 g, 5.03 mmol) in THF (25.2 mL) was added TBAF (1.0 M in THF, 15.1 mL, 15.1 mmol) at 25° C. The reaction mixture was stirred for 15 min at this temperature, then concentrated to afford the titled compound as a brown oil. The crude mixture was carried forward without any additional purification. LC/MS [M+H]=198.2.

Step 5. 4-chloro-1-methyl-5-nitro-1H-pyrrolo[2,3-b]pyridine: To a solution of 4-chloro-5-nitro-1H-pyrrolo[2,3-b]pyridine (994 mg, 5.03 mmol) in THF (25.2 mL) was added DIPEA (1.31 mL, 7.55 mmol) followed by iodomethane (0.47 mL, 7.55 mmol) at 25° C. The reaction mixture was allowed to stir at 25° C. for 15 min. Upon completion, water (10 mL) and EtOAc (5 mL) were added and the aqueous layer was extracted with EtOAc (2×5 mL). The combined organic layers were dried over $MgSO_4$, filtered, and concentrated to afford the crude material as a light brown solid. Purification by flash column chromatography (Hept:EtOAc 1:0 to 3:2) yielded the pure desired product (264 mg, 25%) as a yellow solid. LC/MS [M+H]=212.2; $^1$H NMR (400 MHz, DMSO-$d_6$) δ 9.00 (s, 1 H), 7.90-7.89 (m, 1 H), 6.81-6.80 (m, 1 H), 3.90 (s, 3 H).

Step 6. 3-iodo-4-chloro-1-methyl-5-nitro-1H-pyrrolo[2,3-b]pyridine: To a solution of 4-chloro-1-methyl-5-nitro-1H-pyrrolo[2,3-b]pyridine (218 mg, 1.03 mmol) in DMF (1.14 mL) at 25° C. was added NIS (278 mg, 1.24 mmol). The reaction was allowed to stir at 25° C. for 1.5 h wherein the mixture turned from a yellow suspension to an orange solution. The reaction continued to stir for an additional 12 h at 25° C. Upon completion, water (5 mL) was added, and the precipitate was filtered off as the titled compound (414 mg, 119%) as a light brown solid. The crude solid was carried forward without any additional purification. LC/MS [M+H]=338.1; $^1$H NMR (400 MHz, DMSO-$d_6$) δ 8.95 (s, 1 H), 8.12 (s, 1 H), 3.86 (s, 3 H).

Step 7. 4-chloro-1-methyl-5-nitro-3-(4,4,5,5-tetramethyl-1,3,2-dioxaborolan-2-yl)-1H-pyrrolo[2,3-b]pyridine: A mixture of 4-chloro-3-iodo-1-methyl-5-nitro-1H-pyrrolo[2,3-b]pyridine (250 mg, 0.74 mmol) and tetrakis(triphenylphosphine)palladium (0) (42.8 mg, 0.04 mmol) in dioxane (12 mL) was flushed with $N_2$ for 10 min. To this solution was added, 4,4,5,5-tetramethyl-1,3,2-dioxaborolane (0.431 mL, 2.96 mmol) followed by TEA (0.513 mL, 3.70 mmol). The vial was purged with $N_2$ for 5 min, then sealed and heated to 60° C. for 16 h. Upon completion, the reaction was cooled to 25° C., diluted with DCM (10 mL), and quenched with 1 M HCl (10 mL). The aqueous layer was extracted with DCM (2×5 mL) and the combined organics were dried with $Na_2SO_4$ and concentrated in vacuo. The crude reaction mixture was purified by flash column chromatography (Hept:EtOAc, 1:0 to 2:1) to provide the title compound (185 mg, 74%) as an off white solid. LC/MS [M+H]=338.0; $^1$H NMR (400 MHz, CDCl$_3$) δ 8.89 (s, 1 H), 7.82 (s, 1 H), 3.94 (s, 3 H), 1.40 (s, 12 H).

Step 8. Tert-butyl 4-(4-chloro-1-methyl-5-nitro-1H-pyrrolo[2,3-b]pyridin-3-yl)-3-methyl-3,6-dihydropyridine-1(2H)-carboxylate: A mixture of 4-chloro-1-methyl-5-nitro-3-(4,4,5,5-tetramethyl-1,3,2-dioxaborolan-2-yl)-1H-pyrrolo[2,3-b]pyridine (300 mg, 0.89 mmol), tert-butyl 3-methyl-4-(((trifluoromethyl)sulfonyl)oxy)-3,6-dihydropyridine-1(2H)-carboxylate (291.6 mg, 0.84 mmol), and $K_3PO_4$ (415 mg, 1.96 mmol) in dioxane/water (5/1, 12 mL) was flushed with $N_2$. Tetrakis(triphenylphosphine)palladium (0) (102.7 mg, 0.09 mmol) was quickly added and the vial was flushed with $N_2$ again. The mixture was heated to 70° C. and maintained at this temperature for 22 h. Upon completion, the mixture was diluted with DCM (5 mL) and quenched with 5% aq. citric acid (10 mL). The aqueous layer was washed with DCM (2×5 mL) and the combined organics were dried $Na_2SO_4$ and concentrated in vacuo. The residue was purified by flash column chromatography (Hept:EtOAc 1:0 to 2:1) to provide the desired product (198 mg, 55%) as a yellow glass. LC/MS [M-tBu]=351.1.

Step 9. tert-butyl 4-(4-methoxy-1-methyl-5-nitro-1H-pyrrolo[2,3-b]pyridin-3-yl)-3-methyl-3,6-dihydropyridine-1(2H)-carboxylate: Tert-butyl 4-(4-chloro-1-methyl-5-nitro-1H-pyrrolo[2,3-b]pyridin-3-yl)-3-methyl-3,6-dihydropyridine-1(2H)-carboxylate (198 mg, 0.49 mmol) and cesium carbonate (634 mg, 1.95 mmol) were dissolved in MeOH (8.0 mL) at 25° C. The reaction mixture was allowed to stir at 25° C. for 24 h. Upon completion, AcOH was added until pH 6 was reached. The reaction was concentrated to remove most of the MeOH. The resulting residue was diluted with water (5 mL) and extracted with DCM (3×5 mL). The combined organic layers were concentrated in vacuo to provide the crude title compound (205 mg, 105%) as a yellow gum. No further purification was done, the product was carried forward in the sequence without any further purification or characterization. LC/MS [M+H]=403.3.

Step 10. tert-butyl 4-(5-amino-4-methoxy-1-methyl-1H-pyrrolo[2,3-b]pyridin-3-yl)-3-methylpiperidine-1-carboxylate: A suspension of tert-butyl 4-(4-methoxy-1-methyl-5-nitro-1H-pyrrolo[2,3-b]pyridin-3-yl)-3-methyl-3,6-dihydropyridine-1(2H)-carboxylate (197 mg, 0.49 mmol), ammonium formate (493 mg, 7.83 mmol), and 5% Pd/C (135 mg) of EtOH (25 mL) was bubbled with $N_2$ for 15 min. The suspension was then heated to 85° C. for 4 h under a $N_2$ atmosphere. Upon completion, the reaction was allowed to cool to 25° C. and filtered through a pad of Celite®, rinsing with EtOH (5 mL). The filtrate was concentrated in vacuo to remove the EtOH, then water (10 mL) and CHCl$_3$ (10 mL) were added. The aqueous layer was extracted with CHCl$_3$ (2×5 mL) and DCM (2×5 mL). The combined organic layers were dried with $Na_2SO_4$ and concentrated in vacuo to provide crude title compound (190 mg, 104%) as a colorless glass. The crude material was used directly in the next step without any further purification. LC/MS [M+H]=375.3.

Step 11. tert-butyl 4-(5-(3-cyanobenzamido)-4-methoxy-1-methyl-1H-pyrrolo[2,3-b]pyridin-3-yl)-3-methylpiperidine-1-carboxylate: A mixture of tert-butyl 4-(5-amino-4-methoxy-1-methyl-1H-pyrrolo[2,3-b]pyridin-3-yl)-3-methylpiperidine-1-carboxylate (183 mg, 0.49 mmol), 3-cyanobenzoic acid (115 mg, 0.78 mmol), HATU (278.7 mg, 0.73 mmol) in DMF (5 mL) was treated with DIPEA (0.255 mL, 1.47 mmol) at 25° C. The resulting solution was stirred at 25° C. for 18 h. The crude reaction mixture was then loaded directly onto prep-HPLC (XL-column, acidic, 10-100% MeCN, 80 min gradient) to obtain the title compound (136 mg, 55%) as a white solid. LC/MS [M+H]=504.4; $^1$H NMR (400 MHz, DMSO-$d_6$) δ 9.48-9.42 (m, 1 H), 8.50 (s, 1 H), 8.45-8.40 (m, 1 H), 8.35 (s, 1 H), 8.08-8.04 (m, 1 H), 7.81-7.78 (m, 1 H), 7.12 (s, 1 H), 4.37-4.17 (m, 1 H), 4.04 (s, 3 H), 4.03-3.98 (m, 1 H), 3.83 (s, 3 H), 3.41-3.46 (m, 1 H), 3.20-2.77 (m, 2 H), 2.40-2.27 (m, 1 H), 2.05-1.93 (m, 1 H), 1.70-1.64 (m, 1 H), 1.45 (s, 9 H), 0.69-0.62 (m, 3 H).

Step 12. 3-cyano-N-(4-methoxy-1-methyl-3-(3-methylpiperidin-4-yl)-1H-pyrrolo[2,3-b]pyridin-5-yl)benzamide trifluoroacetate salt: A solution tert-butyl 4-(5-(3-cyanobenzamido)-4-methoxy-1-methyl-1H-pyrrolo[2,3-b]pyridin-3-yl)-3-methylpiperidine-1-carboxylate (136 mg, 0.27 mmol)

in DCM (7.0 mL) at 25° C. was added TFA (0.70 mL). The resulting mixture was stirred at 25° C. for 2 h. Upon completion, the mixture was concentrated in vacuo and the residue was dried thoroughly to provide the crude title compound (140 mg, 100%) as the TFA salt. The crude solid was used directly without any further purification. LC/MS [M+H]=404.3.

Step 13. 3-cyano-N-(3-((3R,4R)-1-(cyclopentanecarbonyl)-3-methylpiperidin-4-yl)-4-methoxy-1-methyl-1H-pyrrolo[2,3-b]pyridin-5-yl)benzamide: A solution of TFA salt of 3-cyano-N-(4-methoxy-1-methyl-3-(3-methylpiperidin-4-yl)-1H-pyrrolo[2,3-b]pyridin-5-yl)benzamide (140 mg, 0.27 mmol) in dry pyridine (5.0 mL) was cooled to 0° C. To this, cyclopentanecarbonyl chloride (0.148 mL, 1.22 mmol) was added, and the reaction mixture was allowed to warm to 25° C. over 3 h. The reaction was stirred at 25° C. for 18 h. Upon completion, the solution was concentrated in vacuo and the crude residue was subjected to prep-HPLC (XL-column, acidic, 30-100% MeCN, 70 min gradient time) to obtain racemic product (87 mg, 64%) as a white solid. The product was separated using a chiral HPLC (Method S) and give the 3-cyano-N-(3-((3S,4S)-1-(cyclopentanecarbonyl)-3-methylpiperidin-4-yl)-4-methoxy-1-methyl-1H-pyrrolo[2,3-b]pyridin-5-yl)benzamide (3.98 min, 30.1 mg, 23%) and 3-cyano-N-(3-((3R,4R)-1-(cyclopentanecarbonyl)-3-methylpiperidin-4-yl)-4-methoxy-1-methyl-1H-pyrrolo[2,3-b]pyridin-5-yl)benzamide (6.35 min, 27.5 mg, 20%, desired isomer). LC/MS [M+H]=500.0; $^1$H NMR (400 MHz, CDCl$_3$) δ 8.92-8.88 (m, 1 H), 8.28-8.20 (m, 2 H), 8.03 (s, 1 H), 7.88-7.87 (m, 1 H), 7.72-7.64 (m, 1 H), 6.84 (s, 1 H), 4.87-4.84 (m, 1 H), 4.63-4.60 (m, 1 H), 4.16-4.13 (m, 1 H), 3.99 (s, 3 H), 3.94-3.91 (m, 1 H), 3.86 (s, 3 H), 3.50 (s, 1 H), 3.41-3.18 (m, 2 H), 3.02-2.91 (m, 2 H), 2.77-2.71 (m, 1 H), 2.40 (s, 1 H), 2.05-1.70 (m, 6 H), 0.67-0.57 (m, 3 H).

Example 25

The following Example 25 was prepared analogous to Example 24 employing the appropriate carboxylic acids in Steps 12 and 14.

Example 26

Preparation of 3-cyano-N-(3-((R)-2,2-dimethyl-1-((R)-2,3,3-trimethylbutanoyl)piperidin-4-yl)-4-methoxy-1-methyl-1H-pyrrolo[2,3-b]pyridin-5-yl)benzamide)

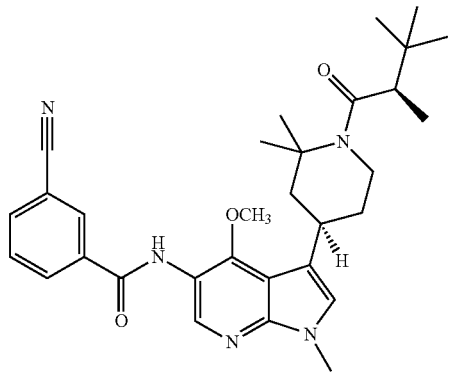 [SMILES: COc1c(NC(=O)c2cccc(C#N)c2)cnc2c1c([C@@H]1CCN(C(=O)[C@H](C)C(C)(C)C)C(C)(C)C1)cn2C]

Step 1. Tert-butyl 2,2-dimethyl-4-((((trifluoromethyl)sulfonyl)oxy)-3,6-dihydropyridine-1(2H)-carboxylate. A solution of NaHMDS (1.0 M in THF, 41.0 mL, 41.0 mmol) in THF (130 mL) was cooled to −78° C. A separate solution of tert-butyl 2,2-dimethyl-4-oxopiperidine-1-carboxylate (7.76 g, 34.1 mmol) in THF (21 mL) was added slowly dropwise via syringe. The resulting solution turned into a slurry over the course of 1 h while maintaining the bath temperature at −78° C. A separately prepared solution of Comins reagent (16.1 g, 41.0 mmol) in THF (20 mL) was then added dropwise via syringe. The resulting slurry turned orange as it warmed slowly to 25° C. over 12 h. Next, the reaction was concentrated, taken up in 15% EtOAc/heptane (100 mL), washed with ice cold water (30 mL), the water layer extracted with 15% EtOAc/heptane (2×100 mL). The combined organics were dried over MgSO$_4$, filtered, and concentrated to give the titled compound which required no further purification: $^1$H NMR (400 MHz, CDCl$_3$) 5.79-5.77 (m, 1 H), 4.09-4.07 (m, 2 H), 2.04 (s, 2 H), 1.50 (s, 6 H), 1.47 (s, 9 H).

Step 2. 4-methoxy-1-methyl-5-nitro-3-(4,4,5,5-tetramethyl-1,3,2-dioxaborolan-2-yl)-1H-pyrrolo[2,3-b]pyridine: To a round bottom flask was charged with 3-iodo-4-methoxy-1-methyl-5-nitro-1H-pyrrolo[2,3-b]pyridine (prepared as described in example 1 (9.60 g, 28.8 mmol), 4,4,5,5-tetramethyl-1,3,2-dioxaborolane (14.8 g, 115.0

| Ex. | Structure | Name/Characterization |
|---|---|---|
| 25 | | 3-cyano-N-(3-((3R,4R)-1-(cyclopentanecarbonyl)-3-methylpiperidin-4-yl)-4-methoxy-1-methyl-1H-pyrrolo[2,3-b]pyridin-5-yl)-4-methoxybenzamide. LC/MS [M + H] = 530.3; Chiral LC: Rt = 2.81 min (Method T); $^1$H NMR (400 MHz, CDCl$_3$) δ 8.89 (s, 1 H), 8.24-8.10 (m, 2 H), 7.95-7.83 (m, 1 H), 7.13-7.11 (m, 1 H), 6.83 (s, 1 H), 4.87-4.84 (m, 1 H), 4.64 (m, 1 H), 4.16-4.13 (m, 1 H), 4.05 (s, 3 H), 3.98 (s, 3 H), 3.95-3.91 (m, 1 H), 3.86 (s, 3 H), 3.41-3.34 (m, 2 H), 3.24-3.18 (m, 1 H), 3.03-2.92 (m, 2 H), 2.77-2.71 (m, 1 H), 2.41 (s, 1 H), 2.05-1.67 (m, 6 H), 0.67-0.61 (m, 3 H). | mmol), TEA (11.7 g, 115 mmol), XPhos (4400 mg, 9.22 mmol) and toluene (300 mL). The mixture was degassed with N₂ three times, then Pd(OAc)₂ (1.04 g, 4.61 mmol) was added. The mixture was degassed with N₂ three times again and stirred at 120° C. for 30 min under N₂ atmosphere. The reaction mixture was filtered through a pad of Celite®, and the resulting filtrate was concentrated in vacuo to give crude product, which was purified by silica gel column chromatography (PE:EtOAc, 100:17 to 100:19) to give the title compound (2.90 g, 30% yield). ¹H NMR (400 MHz, CDCl₃) δ 8.86 (s, 1 H), 7.71 (s, 1 H), 4.11 (s, 3 H), 3.87 (s, 3 H), 1.35 (s, 9 H).

Step 3. tert-butyl 4-(4-methoxy-1-methyl-5-nitro-1H-pyrrolo[2,3-b]pyridin-3-yl)-2,2-dimethyl-3,6-dihydropyridine-1(2H)-carboxylate: To a flask was added tert-butyl 2,2-dimethyl-4-(((trifluoromethyl)sulfonyl)oxy)-3,6-dihydropyridine-1(2H)-carboxylate (2.90 g, 8.71 mmol), 4-methoxy-1-methyl-5-nitro-3-(4,4,5,5-tetramethyl-1,3,2-dioxaborolan-2-yl)-1H-pyrrolo[2,3-b]pyridine (2.90 g, 8.07 mmol), K₃PO₄ (3.70 g, 17.4 mmol) and dixoane/H₂O (100 mL/25 mL), and the mixture was degassed with N₂ for 5 mins, then Pd(dppf)Cl₂ (1.01 g, 0.870 mmol) was added to the mixture and the mixture was heated to 60° C. for 12 h. Upon completion, the mixture was filtered through a pad of Celite® and the filtrate was concentrated in vacuo. The crude reaction mixture was purified by silica gel column chromatography (PE:EtOAc, 50:1 to 9:1) to give the titled compound (2.05 g, 61% yield): ¹H NMR (400 MHz, CDCl₃) δ 8.89 (s, 1 H), 7.16 (s, 1 H), 6.21-6.18 (m, 1 H), 4.14-4.10 (m, 2 H), 3.98 (s, 3 H), 3.90 (s, 3 H), 2.54 (s, 2 H), 1.51 (s, 9 H), 1.49 (s, 6 H).

Step 4. tert-butyl (R)-4-(5-amino-4-methoxy-1-methyl-1H-pyrrolo[2,3-b]pyridin-3-yl)-2,2-dimethylpiperidine-1-carboxylate: To a solution of tert-butyl 4-(4-methoxy-1-methyl-5-nitro-1H-pyrrolo[2,3-b]pyridin-3-yl)-2,2-dimethyl-3,6-dihydropyridine-(2H)-carboxylate (4.10 g, 9.85 mmol) in MeOH (240 mL) and DCM (80 mL) was added Pd(OH)₂/C (553 mg). The mixture was purged with H₂ three times then stirred under hydrogen atmosphere (50 Psi) at 50° C. for 4 h. Upon completion, the suspension was filtered through pad of Celite®. The filtrate was concentrated and purified by silica gel flash column (DCM/MeOH, 1:0-10:1) to give the racemic product (2.10 g, 55%) as a red-yellow solid. LCMS [M+H]=395.1. The racemate (2.10 g) was separated using a chiral HPLC (Method U) and give two peaks which were each collected and concentrated to give peak 1 (4.38 min, 930 mg, 44%) and peak 2 (5.03 min, 930 mg, 44%). Based on Th17 data of the final furnished compounds using each peak, it was determined that the active (R)-enantiomer corresponded to peak 2. Therefore, material corresponding to peak 2 was taken forward in the synthetic sequence; ¹H NMR (400 MHz, CDCl₃) δ 7.89 (s, 1H), 6.92-6.86 (m, 1H), 4.03-3.99 (m, 1H), 3.76-3.69 (m, 4H), 3.30-3.16 (m, 2H), 2.50 (s, 3H), 2.08-2.00 (m, 1H), 1.86-1.82 (m, 1H), 1.69-1.22 (m, 20H).

Step 5. tert-butyl (R)-4-(5-(3-cyanobenzamido)-4-methoxy-1-methyl-1H-pyrrolo[2,3-b]pyridin-3-yl)-2,2-dimethylpiperidine-1-carboxylate: To the stirred solution of tert-butyl (R)-4-(5-amino-4-methoxy-1-methyl-1H-pyrrolo[2,3-b]pyridin-3-yl)-2,2-dimethylpiperidine-1-carboxylate (240 mg, 0.618 mmol) in DCM (20 mL) was added 3-cyanobenzoyl chloride (150 mg, 0.906 mmol) and DIPEA (0.5 mL) at 25° C. The solution was allowed to stir for 1 h, then quenched with water (5 mL) and extracted with DCM (15 mL×2). The combined organic layers were separated, dried, concentrated and purified by column chromatography (EtOAc:PE 30:70 70%) to give product (260 mg, 81%) as a light yellow oil. LCMS [M+H]=518.1; ¹H NMR (400 MHz, CDCl₃) δ 8.93 (s, 1 H), 8.26-8.19 (m, 2 H), 8.07 (s, 1 H), 7.88-7.86 (m, 1 H), 7.69-7.66 (m, 1 H), 6.91 (s, 1 H), 4.05-4.01 (m, 1 H), 3.98 (s, 3 H), 3.85 (s, 3 H), 3.23-3.17 (m, 2 H), 2.21-2.13 (m, 1 H), 1.96-1.88 (m, 1 H), 1.63-1.50 (m, 8 H), 1.49 (s, 9 H).

Step 6. (R)-3-cyano-N-(3-(2,2-dimethylpiperidin-4-yl)-4-methoxy-1-methyl-1H-pyrrolo[2,3-b]pyridin-5-yl)benzamide: To the stirred solution of tert-butyl (R)-4-(5-(3-cyanobenzamido)-4-methoxy-1-methyl-1H-pyrrolo[2,3-b]pyridin-3-yl)-2,2-dimethylpiperidine-1-carboxylate (200 mg, 0.399 mmol) in DCM (20 mL) was added a solution of HCl (5 mL) in dioxane (5 mL) at 15° C. The solution was allowed to stir for 2 hours. Next, the solvent was removed to give the crude HCl salt of the title compound (250 mg) as a yellow solid which was used in the next step without any further purification.

Step 7. 3-cyano-N-(3-((R)-2,2-dimethyl-1-((R)-2,3,3-trimethylbutanoyl)piperidin-4-yl)-4-methoxy-1-methyl-1H-pyrrolo[2,3-b]pyridin-5-yl)benzamide: To the stirred solution of HCl salt of (R)-3-cyano-N-(3-(2,2-dimethylpiperidin-4-yl)-4-methoxy-1-methyl-1H-pyrrolo[2,3-b]pyridin-5-yl)benzamide (50 mg, 0.12 mmol) in DCM (5 mL) was added TEA (0.6 mL) and (R)-2,3,3-trimethylbutanoic acid (200 mg, 1.35 mmol) at 25° C. The reaction was stirred for 12 h, then the solvent was removed. The crude residue was purified by HPLC to give the titled compound (14 mg, 22%) as a white solid: LC/MS [M+H]: 530.2; ¹H NMR (400 MHz, CDCl₃) δ 8.94 (br s, 1H), 8.27-8.22 (m, 2H), 7.88-7.87 (m, 1H), 7.68 (s, 1H), 6.93 (s, 1H), 3.99 (s, 3H), 3.86 (s, 4H), 3.30-3.17 (m, 2H), 2.61-2.60 (m, 1H), 2.18-1.93 (m, 1H), 1.68-1.52 (m, 14H), 1.07-1.05 (m, 3H), 0.99 (s, 9H); Chiral LC:Rt=13.77 min (Method O).

Examples 27-34

The following Examples 27-34 were prepared in a manner analogous to Example 26 employing the appropriate acids in Steps 5 & 7.

| Ex. | Structure | Name/Characterization |
|---|---|---|
| 27 | 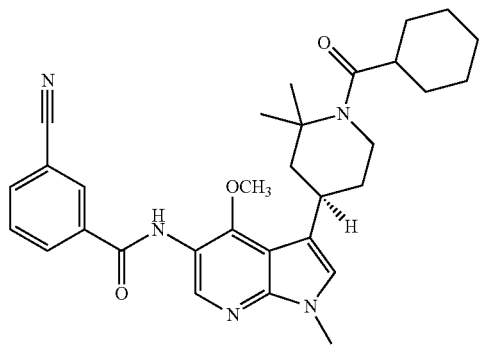 [SMILES: COc1c(NC(=O)c2cccc(C#N)c2)cnc2c1c([C@@H]1CCN(C(=O)C3CCCCC3)C(C)(C)C1)cn2C] | (R)-3-cyano-N-(3-(1-(cyclohexanecarbonyl)-2,2-dimethylpiperidin-4-yl)-4-methoxy-1-methyl-1H-pyrrolo[2,3-b]pyridin-5-yl)benzamide LC/MS [M + H]: 528.3; Chiral LC: Rt = 5.08 min (Method 1); ¹H NMR (400 MHz, CDCl₃) δ 8.94 (s, 1H), 8.26 (s, 1H), 8.21-8.29 (m, 1H), 8.04 (s, 1H), 7.89-7.87 (m, 1H), 7.70-7.66 (m, 1H), 6.93 (m, 1H), 3.98 (s, 3H), 3.85 (s, 3H), 3.79-3.76 (m, 1H), 3.34-3.29 (m, 2H), 2.51-2.45 (m, 1H), 2.26-2.21 (m, 1 H), 1.92-1.44 (m, 16H), 1.27-1.19 (m, 3H). |

| Ex. | Structure | Name/Characterization |
|---|---|---|
| 28 | 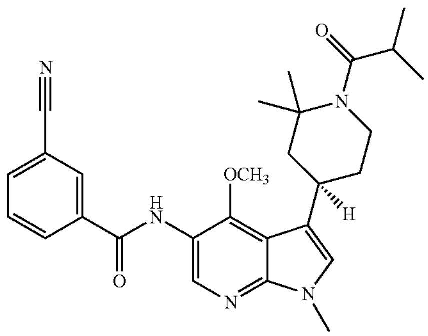 [SMILES: COc1c(NC(=O)c2cccc(C#N)c2)cnc2c1c([C@@H]1CCN(C(=O)C(C)C)C(C)(C)C1)cn2C] | (R)-3-cyano-N-(3-(1-isobutyryl-2,2-dimethylpiperidin-4-yl)-4-methoxy-1-methyl-1H-pyrrolo[2,3-b]pyridin-5-yl)benzamide. LC/MS [M + H]: 488.1; Chiral LC: Rt = 7.85 min (Method K); ¹H NMR (400 MHz, CDCl₃) δ 8.95 (s, 1H), 8.26 (s, 1H), 8.21-8.19 (m, 1H), 8.01 (s, 1H), 7.89-7.87 (m, 1H), 7.70-7.68 (m, 1H), 6.94 (s, 1H), 3.99 (s, 3H), 3.86 (s, 3H), 3.84-3.78 (m, 1H), 3.37-3.31 (m, 2H), 2.84-2.80 (m, 1H), 2.30-2.18 (m, 1H), 1.94-1.90 (m, 1H), 1.75-1.69 (m, 2H), 1.61 (s, 3H), 1.54 (s, 3H), 1.15-1.10 (m, 6H). |
| 29 | 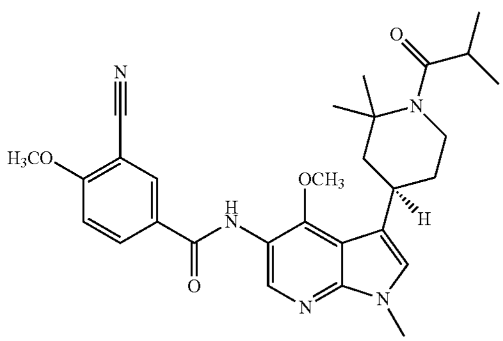 [SMILES: COc1ccc(C(=O)Nc2cnc3c(c([C@@H]4CCN(C(=O)C(C)C)C(C)(C)C4)cn3C)c2OC)cc1C#N] | (R)-3-cyano-N-(3-(1-isobutyryl-2,2-dimethylpiperidin-4-yl)-4-methoxy-1-methyl-1H-pyrrolo[2,3-b]pyridin-5-yl)-4-methoxybenzamide. LC/MS [M + H]: 518.1; Chiral LC: RT = 3.72 min (Method G); ¹H NMR (400 MHz, CDCl₃) δ 8.91 (s, 1H), 8.21-8.17 (m, 2H), 7.91 (s, 1H), 7.14-7.11 (m, 1H), 6.93 (s, 1H), 4.05 (s, 3H), 3.98 (s, 3H), 3.85-3.78 (m, 4H), 3.38-3.28 (m, 2H), 2.84-2.81 (m, 1H), 2.28-2.18 (m, 1H), 1.94-1.91 (m, 1H), 1.76-1.70 (m, 2H), 1.61 (s, 3H), 1.54 (s, 3H), 1.16-1.11 (m, 6H). |
| 30 | 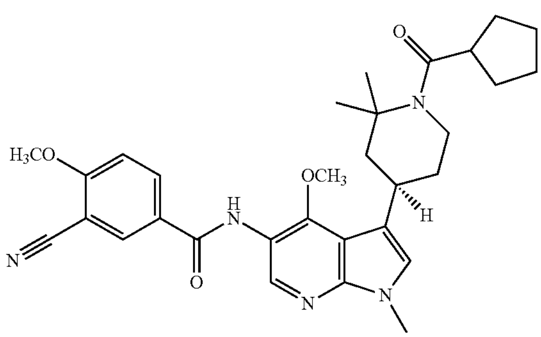 [SMILES: COc1ccc(C(=O)Nc2cnc3c(c([C@@H]4CCN(C(=O)C5CCCC5)C(C)(C)C4)cn3C)c2OC)cc1C#N] | (R)-3-cyano-N-(3-(1-(cyclopentanecarbonyl)-2,2-dimethylpiperidin-4-yl)-4-methoxy-1-methyl-1H-pyrrolo[2,3-b]pyridin-5-yl)-4-methoxybenzamide LC/MS [M + H]: 544.3; Chiral LC: Rt = 3.95 min (Method G); ¹H NMR (400 MHz, CDCl₃) δ 8.90 (s, 1H), 8.21-8.18 (m, 2H), 7.93 (s, 1H), 7.13-7.11 (m, 1H), 6.92 (s, 1H), 4.05 (s, 3H), 3.98 (s, 3H), 3.87-3.77 (m, 4H), 3.42-3.26 (m, 2H), 2.95-2.90 (m, 1H), 2.25-2.19 (m, 1H), 1.93-1.54 (m, 17H). |
| 31 | 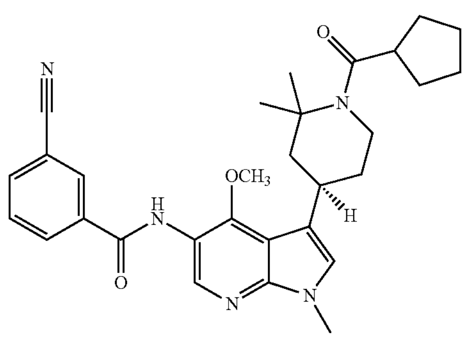 [SMILES: COc1c(NC(=O)c2cccc(C#N)c2)cnc2c1c([C@@H]1CCN(C(=O)C3CCCC3)C(C)(C)C1)cn2C] | (R)-3-cyano-N-(3-(1-(cyclopentanecarbonyl)-2,2-dimethylpiperidin-4-yl)-4-methoxy-1-methyl-1H-pyrrolo[2,3-b]pyridin-5-yl)benzamide LC/MS [M + H]: 514.1; Chiral LC: Rt = 9.66 min (Method K); ¹H NMR (400 MHz, CDCl₃) δ 8.95 (s, 1H), 8.26 (s, 1H), 8.21-8.19 (m, 1H), 8.01 (s, 1H), 7.89-7.87 (m, 1H), 7.70-7.68 (m, 1H), 6.93 (s, 1H), 3.99 (s, 3H), 3.86 (s, 3H), 3.85-3.80 (m, 1H), 3.37-3.20 (m, 2H), 2.92-2.85 (m, 1H), 2.27-2.22 (m, 1H), 1.90-1.69 (m, 11H), 1.62 (s, 3H), 1.54 (s, 3H). |

-continued

| Ex. | Structure | Name/Characterization |
|---|---|---|
| 32 | 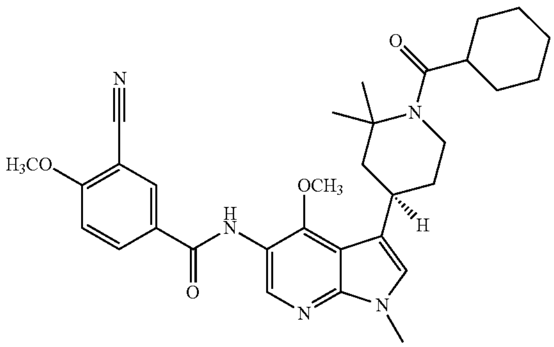 [SMILES: COc1ccc(C(=O)Nc2cnc3c(c([C@@H]4CCN(C(=O)C5CCCCC5)C(C)(C)C4)cn3C)c2OC)cc1C#N] | (R)-3-cyano-N-(3-(1-(cyclohexanecarbonyl)-2,2-dimethylpiperidin-4-yl)-4-methoxy-1-methyl-1H-pyrrolo[2,3-b]pyridin-5-yl)-4-methoxybenzamide LC/MS [M + H]: 558.1; Chiral LC: Rt = 7.57 min (Method H); $^1$H NMR (400 MHz, DMSO-d$_6$) δ 10.10 (s, 1H), 8.42 (s, 1H), 8.41-8.32 (m, 1H), 8.06 (s, 1H), 7.43-7.41 (m, 1H), 7.24 (s, 1H), 4.01 (s, 3H), 3.90 (s, 3H), 3.74 (s, 3H), 3.34-3.24 (m, 2H), 2.55-2.51 (m, 1H), 2.10-2.05 (m, 1H), 1.79-1.76 (m, 1H), 1.72-1.58 (m, 7H), 1.46 (s, 3H), 1.34 (s, 3H), 1.30-1.16 (m, 6H). |
| 33 | 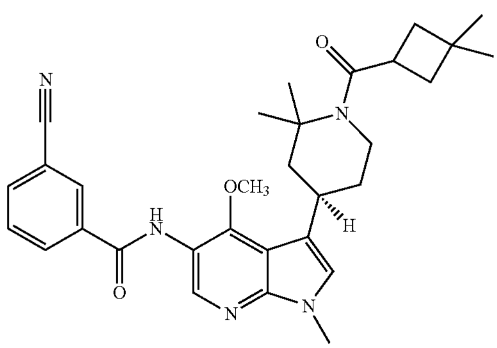 [SMILES: COc1c(NC(=O)c2cccc(C#N)c2)cnc2c1c([C@@H]1CCN(C(=O)C3CC(C)(C)C3)C(C)(C)C1)cn2C] | (R)-3-cyano-N-(3-(1-(3,3-dimethylcyclobutane-1-carbonyl)-2,2-dimethylpiperidin-4-yl)-4-methoxy-1-methyl-1H-pyrrolo[2,3-b]pyridin-5-yl)benzamide. LC/MS [M + H]: 528.1; Chiral LC: Rt = 13.97 (Method O); $^1$H NMR (400 MHz, DMSO-d$_6$) δ 10.26 (s, 1H), 8.46 (s, 1H), 8.33-8.31 (m, 1H), 8.10 (s, 2H), 7.79-7.77 (m, 2H), 7.25 (s, 1H), 3.91 (s, 3H), 3.74 (s, 3H), 3.56-3.32 (m, 1H), 3.18-3.11 (m, 3H), 1.96 (br s, 1H), 1.94-1.83 (M, 4H), 1.77-1.60 (m, 2H), 1.66 (s, 3H), 1.63 (s, 3H), 1.50 (s, 3H), 1.40 (s, 3H), 1.14 (s, 3H), 1.01 (s, 3H) |
| 34 | 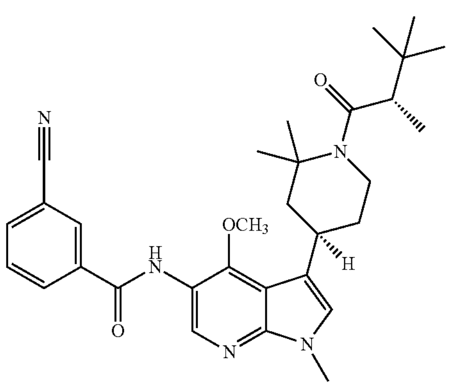 [SMILES: COc1c(NC(=O)c2cccc(C#N)c2)cnc2c1c([C@@H]1CCN(C(=O)[C@@H](C)C(C)(C)C)C(C)(C)C1)cn2C] | 3-cyano-N-(3-((R)-2,2-dimethyl-1-((S)-2,3,3-trimethylbutanoyl)piperidin-4-yl)-4-methoxy-1-methyl-1H-pyrrolo[2,3-b]pyridin-5-yl)benzamide. LC/MS [M + H]: 530.3; Chiral LC: Rt = 13.88 min (Method B); $^1$H NMR (400 MHz, CDCl$_3$): δ 8.94 (s, 1H), 8.26-8.19 (m, 2H), 8.05 (s, 1H), 7.89-7.87 (m, 1H), 7.70-7.66 (m, 1H), 6.93 (s, 1H), 3.98 (s, 3H), 3.86 (s, 3H), 3.78-3.74 (m, 1H), 3.48-3.20 (m, 2H), 2.65-2.60 (m, 1H), 2.31-2.30 (m, 1H), 1.89-1.76 (m, 2H), 1.74-1.56 (m, 7H), 1.11-1.09 (m, 3H), 1.02 (s, 9H). |

Example 35

Preparation of (R)-3-cyano-N-(4-methoxy-1-methyl-3-(1-(2,3,3-trimethylbutanoyl)piperidin-4-yl)-1H-pyrrolo[2,3-b]pyridin-5-yl)-4-(methylthio)benzamide

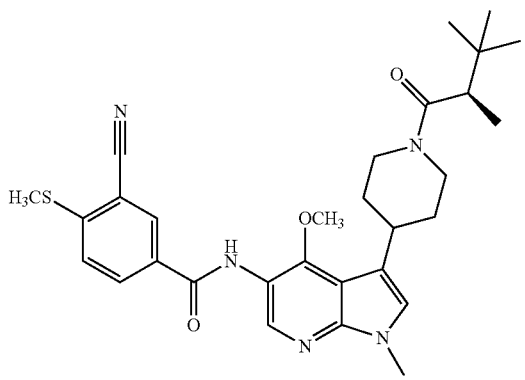

Step 1. Methyl 3-cyano-4-fluorobenzoate. To a solution of 3-cyano-4-fluorobenzoic acid (1800 mg, 10.9 mmol) in MeOH (30 mL) was added SOCl$_2$ (1.2 mL) dropwise at 0° C. After complete addition, the reaction mixture was heated to 80° C. for 9 hours. The solvent was removed under reduced pressure to afford a white solid, which was dissolved in EtOAc. The organic layer was washed with H$_2$O, brine, dried over Na$_2$SO$_4$, and concentrated to afford the title compound as white solid (1700 mg, 87%). $^1$H NMR (400 MHz, CDCl$_3$) δ 8.36-8.30 (m, 2H), 7.33-7.29 (m, 1H), 3.96 (s, 3H) ppm.

Step 2. Methyl 3-cyano-4-(methylthio)benzoate. To the stirred solution of methyl 3-cyano-4-fluorobenzoate (1500 mg, 8.373 mmol) in DMF (30 mL) was added MeSNa (1170 mg, 16.7 mmol) at 25° C. The contents of the flask were then allowed to stir at 60° C. for 2 hours. Water (15 mL) was added, the mixture was filtered, and the filter cake was washed with EtOAc (50 mL). The filtrate was extracted with H$_2$O (30 mL), the organic layer was separated and dried over Na$_2$SO$_4$ and concentrated. The crude material was purified by column chromatography (EtOAc:PE=10:90) to give the title compound (1.1 g, 63.4%) as a white solid. $^1$H NMR (400 MHz, CDCl$_3$) δ 8.24-8.14 (m, 2H), 7.32-7.30 (m, 1H), 3.94 (s, 3H), 2.61 (s, 3H) ppm.

Step 3. 3-cyano-4-(methylthio)benzoic acid. To a stirred solution of methyl 3-cyano-4-(methylthio)benzoate (1100 mg, 5.3 mmol) in THF (20 mL) was added NaOH (1 N, 20 mL) at 25° C. The resulting mixture was allowed to stir for 2 hours, 1 N HCl (25 mL) was added to adjust the pH to 5, the mixture was extracted with DCM, the organic layer was separated, dried over Na$_2$SO$_4$, and concentrated to give the title compound (700 mg, 68%) as a white solid. $^1$H NMR (400 MHz, CD$_3$OD) δ 8.20-8.16 (m, 2H), 7.52-7.49 (m, 1H), 2.63 (s, 3H) ppm. MS [M−H]=192.0

Step 4. tert-butyl 4-(5-(3-cyano-4-(methylthio)benzamido)-4-methoxy-1-methyl-1H-pyrrolo[2,3-b]pyridin-3-yl)piperidine-1-carboxylate. To the stirred solution of tert-butyl 4-(5-amino-4-methoxy-1-methyl-1H-pyrrolo[2,3-b]pyridin-3-yl)piperidine-1-carboxylate (prepared as described is step 7, example 1) (100 mg, 0.277 mmol) in THF (20 mL) was added 3-cyano-4-(methylthio)benzoic acid (107 mg, 0.555 mmol), 2-chloro-1-methylpyridinium iodide (142 mg, 0.555 mmol) and DIPEA (1 mL) at 25° C. The resulting solution was allowed to stir for 2 hours, at which time LC/MS showed the reaction to be complete. Water (10 mL) was added and the mixture was extracted with DCM (10 mL*3). The combined organic layers were dried over Na$_2$SO$_4$, filtered and concentrated. Purification was performed by column chromatography (EtOAc:PE=10:90) and the resulting crude product was dissolved with DCM (15 mL) and washed with 1N NaOH (15 mL×2). NMR showed the title compound to be contaminated with 2-chloro-5 1-methylpyridinium iodide so material was used without further purification (130 mg, 87.5%). MS [M+H]=536.1.

Step 5. 3-cyano-N-(4-methoxy-1-methyl-3-(piperidin-4-yl)-1H-pyrrolo[2,3-b]pyridin-5-yl)-4-(methylthio)benzamide. To the stirred solution of tert-butyl 4-(5-(3-cyano-4-(methylthio)benzamido)-4-methoxy-1-methyl-1H-pyrrolo[2,3-b]pyridin-3-yl)piperidine-1-carboxylate (100 mg, 0.205 mmol) in DCM (25 mL) was added HCl in dioxane (10 mL) at 15° C., which was then allowed to stir for 2 hours. The solvent was removed and the residue was used directly in next step without further purification (130 mg, 145%) as a brown solid.

Step 6. (R)-3-cyano-N-(4-methoxy-1-methyl-3-(1-(2,3,3-trimethylbutanoyl)piperidin-4-yl)-1H-pyrrolo[2,3-b]pyridin-5-yl)-4-(methylthio)benzamide. To a stirred solution of 3-cyano-N-(4-methoxy-1-methyl-3-(piperidin-4-yl)-1H-pyrrolo[2,3-b]pyridin-5-yl)-4-(methylthio)benzamide (130 mg, 0.298 mmol) in DCM (30 mL) was added (R)-2,3,3-trimethylbutanoic acid (100 mg, 0.768 mmol), HATU (150 mg, 0.394 mmol) and DIPEA (2 mL) at 25° C. The resulting mixture was allowed to stir for 2 hours. The mixture was diluted with water (15 mL), extracted with DCM (25 mL×2), and the combined organic layers were dried over Na$_2$SO$_4$ and concentrated. The crude material was purified by prep HPLC to give the title compound (35, 13 mg, 8%) as a white solid: $^1$H NMR (400 MHz, CD$_3$OD) δ 8.86-8.84 (m, 1H), 8.16-8.03 (m, 3H), 7.42-7.39 (m, 1H), 6.89 (s, 1H), 4.23-4.20 (m, 1H), 3.99 (s, 3H), 3.85 (s, 3H), 3.24-3.12 (m, 2H), 2.72-2.64 (m, 6H), 2.20-2.09 (m, 2H), 1.57-1.52 (m, 1H), 1.13-1.10 (m, 3H), 1.02-0.99 (m, 10H) ppm. MS [M+H+]=548.2.

Example 36

Assay of Co-Activator Recruitment by TR-FRET

The activity of compound of the invention can be determined by a co-activator recruitment by TR-FRET (time-resolved fluorescence resonance energy transfer) assay. In general, the assay is based on the interaction between N-terminally Six-Histidine-tagged-RORC2 ligand binding domain (6-His-RORC2 LBD), expressed in *E. coli* and purified by affinity chromatography, and biotin-coactivator peptide SRC1-2 (biotin-aminohexanoic acid-CPSSHSS-LTERHKILHRLLQEGSPS-NH$_2$; SEQ ID NO: 1) containing the LXXLL consensus domain which is responsible for receptor binding. This interaction is detected by addition of Europium labeled-anti-His antibody (Ex. 337 nm, Em. 620 nm, which binds to 6His) and Streptavidin-APC (Ex. 620 nm, Em. 665 nm, which binds to biotin). When receptor and coactivator are bound to each other, upon shining light at 337 nm on the sample, the Europium emits fluorescence that excites APC due to close proximity (FRET) and this signal is measured at 665 nm. Due to the long lasting fluorescence emission of Europium, the non-specific, short-lived fluorescence is time-resolved (TR) from the fluorescence of interest. Inhibitors of the interaction of receptor and coactivator peptide are detected by a decrease in TR-FRET signal.

Specifically, in one embodiment the aforementioned assay was performed as outlined below. The assay was carried out in black polystyrene. 384-well plates in a total assay volume of 50.5 μL. The assay buffer contained 50 mM TRIS-HCL pH 7.5, 1 mM NaCl, 2 mM $MgCl_2$, 0.5 mg/mL bovine serum albumin, and 5 mM dithiothreitol. The final concentration of reagents was 6.3 nM RORC2 LBD, 200 nM SRC1-2, 50 nM streptavidin APC, 1 nM Europium-labeled anti-His antibody, and varying concentrations of compounds such that final concentration of DMSO is 1% (v/v). The assay steps were: (1) dispensing 500 μL compound at 100× final concentration in DMSO (test wells) or DMSO only (control wells for no inhibition); and (2) dispensing 50 μL mixture of the other assay components including receptor (test wells) or excluding receptor (control wells for maximal inhibition).

Assay mixtures were incubated are room temperature for 3 hr and read in EnVision 2100 Multilabel Reader (PerkinElmer Life Sciences) at Excitation Filter 320, Emission Europium Filter 615, Emission APC Filter 665, Dichroic Mirror D400/D630.

TR-FRET signal was determined by calculating the ratio of 665 nm by 615 nm and ICW values of compounds of the invention (Table 1) were determined by the non-linear regression analysis of dose response curves.

References which relate to the above-referenced assay include: Kallen et al. Structure, 2002, 10, 1697-1707; Stehlin et al. EMBO J 2001, 20, 5822-5831; and Zhou et al. Mol Endocrinol 1998, 12, 1594-1604.

TABLE 1

| Example | $IC_{50}$ (nM) |
|---|---|
| 1 | 16.9 |
| 2 | 38.7 |
| 3 | 4.6 |
| 4 | 6.9 |
| 5 | 6.1 |
| 6 | 15.2 |
| 7 | 4.7 |
| 8 | 11.8 |
| 9 | 56.2 |
| 10 | 29.2 |
| 11 | 17.8 |
| 12 | 20.2 |
| 13 | 15.4 |
| 14 | 14.2 |
| 15 | 8.6 |
| 16 | 7.2 |
| 17 | 14.2 |
| 18 | 7.1 |
| 19 | 13.3 |
| 20 | 23.2 |
| 21 | ND |
| 22 | ND |
| 23 | 31.2 |
| 24 | 10.2 |
| 25 | 10.1 |
| 26 | 10.4 |
| 27 | 4.8 |
| 28 | 6.2 |
| 29 | 8.1 |
| 30 | 13.5 |
| 31 | 5.7 |
| 32 | 5.8 |
| 33 | 8.5 |
| 34 | 9.4 |
| 35 | 3.2 |

ND = not determined

Example 37

Assay of Gal4-RORC2 Activity by Luciferase Reporter

The activity of compound of the invention can be also be determined by a luciferase reporter Gal4-RORC2 activity assay. In general, Neuro2A cells (murine neuroblastoma cell line obtained from HPACC, cat #89121404) are transiently transfected with a mammalian expression vector (pM) containing Gal4-RORC2 LBD and a Gal4-responsive reporter gene containing firefly luciferase (5×GAL4UAS-Luc3). Gal4-RORC2 LBD is constitutively active in the transfected Neuro2a cells, resulting in a robust luciferase response in the absence of stimulation. Upon treatment with an RORC2 inhibitor the transcriptional response is decreased and the magnitude of the decrease in response is dose-dependently related to the intrinsic efficacy of the inhibitor.

Specifically, the growth medium was composed by MEM EBS w/o L-glutamine, 10% (v/v) FBS, 2 mM L-glutamine and 1× non-essential aminoacid (NEAA); the seeding medium was composed by MEM EBS w/o L-glutamine, w/o phenol red, 4% (v/v) FBS, 2 mM L-glutamine, 1×NEAA, 1% Penicillin (10,000 U/mL)/Streptomycin (10,000 μg/mL); and the assay medium was composed by MEM EBS w/o L-glutamine, w/o phenol red, 4% (v/v) FBS, 2 mM L-glutamine, 1×NEAA, 1% Penicillin (10,000 U/mL)/Streptomycin (10,000 μg/mL). In addition, Neuro2A cells were cultured in growth medium in humidified chambers at 37° C. and 5% $CO_2$ using standard tissue culture procedures.

On day one of the assay, cells were seeded and transfected. Specifically, Neuro2A cells were suspended in seeding medium and mixed with plasmids and transfection reagent which was dissolved in OptiMEM I reduced serum medium (InVitrogen), and then seeded to 384-well plates (Corning, Black, Clear bottom) in 40 μL/well containing 12,500 cells, 17.25 ng Gal4-Luc3, 5.75 ng either empty pM vector ('no receptor control' wells) or pM-Gal4RORgamma-LBD, and 0.11 μL Lipofectamine2000.

On day two of the assay, the cells were treated with compounds of the invention. Specifically, the treatment was started 20-24 hr after seeding and transfection of the cells. Compounds of the invention were serially diluted in a 384-well polypropylene plate with assay medium containing 0.5% (v/v) DMSO at 5× final assay concentration. 10 μL of the compounds (or 0.5% DMSO in assay medium for 'no compound control' wells) were transferred from the dilution plate to the 384-format cell plate such that final assay volume was 50 μL and final DMSO concentration was 0.1% (v/v), followed by incubation for 20-24 hr in humidified chambers at 37° C. and 5% $CO_2$.

On day three of the assay, luminescence was measured and the results analyzed. Specifically, 10 μL of SteadyLite Plus reagent (Perkin Elmer) was added to each well. The cell plates were incubated at room temperature for 15 min in the dark before reading of luminescence on the MicroBeta Trilux (Wallac). $IC_{50}$ values of the compounds tested were determined by the non-linear regression analysis of dose response curves.

References which relate to the above-referenced assay include: Stehlin-Gaon et al. Nature Structural Biology 2003, 10, 820-825; Wang et al. J Biol Chem. 2010, 285(7), 5013-5025; Kumar et al. Mol Pharmacol. 2010, 77(2), 228-36.

Example 38

Assay of IL-17 Production from Human Th17 Cells

The activity of compound of the invention can be also be determined by an IL-17 production from human Th17 cells assay. In general, this assay measures blockade of IL-17 production, the signature cytokine of T helper 17 (Th17) cells, by compounds. Purified human CD4+ T cells are stimulated with anti-CD3+anti-CD28 and incubated with a cytokine cocktail that induce their differentiation into Th17 in the absence or presence of various concentrations of compound. After 6 days, IL-17A concentration is measured in the cell culture supernatant with an ELISA kit (MSD).

Preparation of human CD4+ T cells. CD4+ T cells were purified from buffy coats from healthy donors (obtained from Massachusetts General Hospital) by negative selection the following procedure: Mixing 25 mL of blood with 1 mL of Rosette Sep CD4+ T cell enrichment cocktail (StemCell Technologies) followed by application of a layer of 14 mL Ficoll Paque Plus (Amersham GE Healthcare) and subsequent centrifugation at 1200 g for 20 min at room temperature. The Ficoll layer was then harvested and washed with phosphate saline buffer containing 2% (v/v) fetal bovine serum and cells were resuspended with RPMI medium containing 10% (v/v) fetal bovine serum and 10% (v/v) DMSO, frozen and kept in LN2 until used.

On the first day of the assay, a vial containing $10^7$ CD4+ T cells is thawed rapidly in 37° C. water bath, immediately transferred into 20 mL X-Vivo 15 medium (Lonza), is spun for 6 min at 300×g, the supernatant is discarded, and the resulting pellet is re-suspended at $10^6$ cells/mL in 50 mL fresh X-Vivo 15 medium, followed by storage overnight in a tissue culture vessel in a humidified chamber at 37° C. and 5% $CO_2$. Serial dilutions of compounds of the invention are prepared at 10× final concentration in X-Vivo15 medium containing 3% (v/v) DMSO.

On the second day of the assay, a 384-well tissue culture plate was coated with 10 μg/mL anti-hCD3 (eBioscience) at 50 μL/well. After 2 hr at 37° C., the supernatant is discarded and the coated plates are kept in a sterile tissue culture hood.

Cytokine plus anti-CD28 cocktail is prepared by mixing 25 ng/mL hIL-6 (Peprotech), 5 ng/mL hTGFbeta1 (Peprotech), 12.5 ng/mL IL-1beta (Peprotech), 25 ng/mL hIL-21, 25 ng/mL hIL-23 (R&D Systems), and 1 ug/mL anti-hCD28 (eBioscience) in X-Vivo 15 medium. The cytokine plus anti-CD28 cocktail with CD4+ cells is prepared such that the cocktail is diluted 10-fold and cell density is $0.22 \times 10^6$/mL. The mixture is incubated 1 hr at 37° C.

90 μL (20,000 cells) dispensed per well in the anti-hCD3 coated plate prepared as noted above.

10 μL 10× compound is added per well (final DMSO=0.3%) from the compound plate that was previously prepared, followed by 6 days of incubation in a tissue culture vessel in a humidified chamber at 37° C. and 5% $CO_2$.

On day six of the assay, production of IL-17A in 10 μL of the supernatant is determined by sandwich ELISA using 384w hIL17 MSD plates following the manufacturer's protocol. Measurement is carried out in a Sector Imager 6000 by the same manufacturer. Signal units from the instrument are converted to pg/mL using a calibration curve with known amounts of IL-17A. $IC_{50}$ values of test compounds (Table 2) are determined by the non-linear regression analysis of dose response curves.

A reference which relates to the above-referenced assay is: Yang et al. Nature 2008, 454, 350-352.

TABLE 2

| Example | $IC_{50}$ (nM) |
| --- | --- |
| 1 | 7.2 |
| 2 | 17.8 |
| 3 | 6.4 |
| 4 | 11.0 |
| 5 | 10.6 |
| 6 | 15.7 |

TABLE 2-continued

| Example | $IC_{50}$ (nM) |
| --- | --- |
| 7 | 28.3 |
| 8 | 29.8 |
| 9 | 77.1 |
| 10 | 105.7 |
| 11 | 50.7 |
| 12 | 59.8 |
| 13 | 9.5 |
| 14 | 42.1 |
| 15 | 23.5 |
| 16 | 36.5 |
| 17 | 82.0 |
| 18 | 6.5 |
| 19 | 22.3 |
| 20 | 112.5 |
| 21 | 21.3 |
| 22 | 22.7 |
| 23 | 38.0 |
| 24 | 25.0 |
| 25 | 12.0 |
| 26 | 6.4 |
| 27 | 11.3 |
| 28 | 21.2 |
| 29 | 8.9 |
| 30 | 6.7 |
| 31 | 7.2 |
| 32 | 11.0 |
| 33 | 15.6 |
| 34 | 23.1 |
| 35 | 12.7 |

Example 26

Inhibition of Superantigen-Induced Th17 Cytokine Production

Exotoxins called "superantigens" are among the most powerful T cell activators. Superantigens bind to the cell surface of major histocompatibilty complex (MHC) molecules, without intracellular processing. They stimulate T cells via the T cell receptor, irrespective of the antigen specificities. Therefore, bacterial superantigens are able to activate a large pool of CD4+ as well as CD8+ T cells in contrast to the low T cell frequency for conventional antigens. CD4+ T cells can be classified into various subsets (Th0, Th1, Th2, Th17) based on their respective cytokine secretion profiles. Th0 cells are uncommitted naïve precursor cells that primarily produce IL-2 upon stimulation. Th0 cells upon activation can differentiate into Th1, Th2, or the Th17 subset depending on the local cytokine milieu. Th1 cells mainly produce Inf-γ; Th2 cells, IL-4, IL-5, and IL-13, and Th17 cells, IL-17, and IL-22. During a classical immune response, the differentiation of T helper subset occurs over days, or longer. In the superantigen in-vivo model in mice injection of superantigen triggers a rapid transcription and translation of the various cytokines (i.e. IL-2, IL-4, Inf-γ, IL-17) of the different Th subsets after only 6 hr. A RORγt inhibitor given to animals prior to the superantigen stimulus would impair the Th17 cytokine profile without affecting the cytokine profile of the other Th subsets (Th0, Th1, Th2). The model uses approximately 8 week old C57BL/6, Balb/c, or C3H/HeJ mice which are dosed orally with compound 1 to 2 hr prior to superantigen injection on the day of the experiment (Day 0) based on the pharmacokinetic (PK) profile of the compound. An optional dose may be given the day before superantigen injection (Day −1) to further inhibit the response if necessary. C57BL/6 and Balb/c mice will be sensitized 1 hr prior to superantigen injection with approximately 25 mg/mouse D-Galactosamine intraperitoneally (C3H/HeJ mice do not need to be sensitized). Based on the literature superantigen is typically given at 10 µg/mouse intraperitoneally. Mice will be sacrificed at 3 hr for RNA analysis or up to 6 hr for cytokine analysis.

A reference which relates to the above-referenced assay is: Rajagopalan, G. et. al. Physiol Genomics 2009, 37, 279.

Example 27

Imiquimod Assay

Commercially available 5% imiquimod (IMQ) cream (3M Pharmaceuticals) is applied to the back and right ear of each experimental mouse for two consecutive days. Control mice are treated similarly with a commercially available vehicle cream. The experimental mice are then administered with RORγt inhibitors, and the control mice with vehicle, for 4 days. The ear thickness is measured on all days by digital micrometer (Mitutoyo). Tissues, such as ears and speens, are harvested on Day 5 for RNA analysis. Ear swelling and serum measurements are also made.

References describing aspects of this assay include: Van der Fits, L. et al. J. Immunol. 2009, 182(9), 5836-45; Van Belle, A. B. et al. J Immunol. 2012, 188(1), 462-9; Cai, Y. et al. Immunity 2011, 35(4), 596-610; Fanti, P. A. et al. Int. J. Dermatol. 2006, 45(12), 1464-5; Swindell, W. R. et al. PLoS One 2011, 6(4), e18266; and Roller, A. et al. J. Immunol. 2012, 189(9), 4612-20.

Example 28

IL-23 Injection Model of Mouse Skin Inflammation

Ears from BALB/c mice were each injected intra-dermally every other day with 150 ng of mouse recombinant IL-23 (eBiosciences) or PBS in a total volume of 25 µl. Ear swelling was measured in triplicate using a micrometer (Mitutoyo) right before each IL-23 challenge. On Day 14, mice were euthanized and ears were collected for measurement of cytokine levels, gene expression levels and hystopathological evaluation. Mice were administered 3-100 mg/kg of an RORC2 modulator or vehicle once daily orally for the duration of the study. Alternatively, the RORC2 modulator was applied topically once or twice daily using a standard formulation (EtOH:propylene glycol:dimethyl isosorbide:DMSO, 38:30:15:15) at a concentration of 0.1% to 5.0%.

References describing aspects of this assay include: Muramoto, K. et al. J. Pharmacol. Exp. Ther. 2010, 335(1), 23-31; Fridman, J. S. et al. J. Invest. Dermatol. 2011, 131(9), 1838-1844.

INCORPORATION BY REFERENCE

All publications, patents and patent applications mentioned in this specification are herein incorporated by reference to the same extent as if each individual publication, patent or patent application was specifically and individually indicated to be incorporated by reference.

We claim:

1. A compound of Formula I:

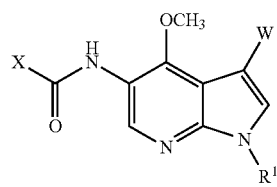

I or a pharmaceutically acceptable salt thereof, wherein,
X is phenyl optionally substituted with one, two, three, four or five substituents independently selected from the group consisting of —CH$_3$, —CH$_2$CH$_3$, —CH$_2$OH, —OH, —OCH$_3$, —SCH$_3$, —OCH$_2$CH$_3$, —OCH$_2$CH$_2$OH, —OCH$_2$CH$_2$OCH$_3$, —F, —Cl, —Br and —CN;
R$^1$ is —CH$_3$ or —CH$_2$CH$_3$;
W is

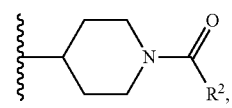

optionally substituted with one, two, three, four or five —CH$_3$; and
R$^2$ is (C$_1$-C$_6$)alkyl, (C$_3$-C$_{10}$)cycloalkyl, phenyl, tetrahydrothiophenyl, thietanyl or indanyl, optionally substituted with one, two, three, four or five substituents independently selected for each occurrence from the group consisting of —F, —Cl, —Br, —OH, ($C_1$-$C_3$)alkyl, ($C_1$-$C_3$)haloalkyl and ($C_3$-$C_{10}$)cycloalkyl.

2. The compound of claim 1, wherein $R^1$ is —$CH_3$.

3. The compound of claim 2, wherein W is

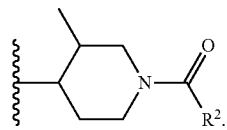

4. The compound of claim 2, wherein W is

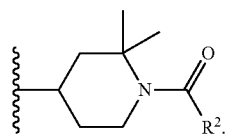

5. The compound of claim 4, wherein X is phenyl substituted with —CN and optionally substituted with one or two substituents independently selected from the group consisting of —$CH_3$, —$CH_2CH_3$, —$CH_2OH$, —OH, —$OCH_3$, —$SCH_3$, —$OCH_2CH_3$, —$OCH_2CH_2OH$, —$OCH_2CH_2OCH_3$, —F, —Cl, —Br and —CN.

6. The compound of claim 4, wherein X is

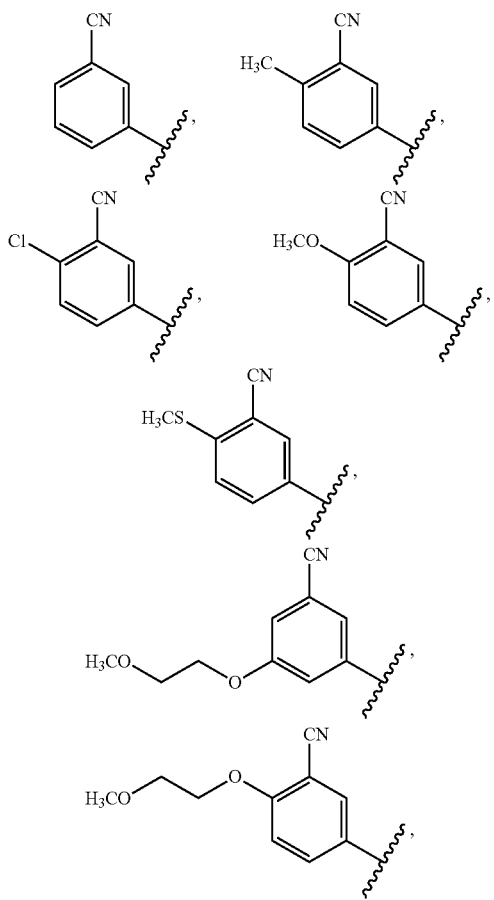

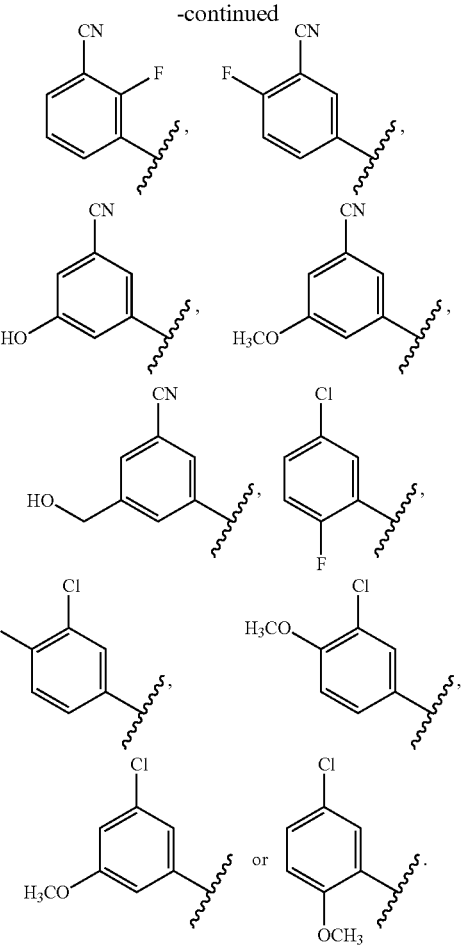

7. The compound of claim 6, wherein $R^2$ is ($C_1$-$C_6$)alkyl.

8. The compound of claim 6, wherein $R^2$ is unsubstituted ($C_3$-$C_{10}$)cycloalkyl.

9. The compound of claim 6, wherein $R^2$ is

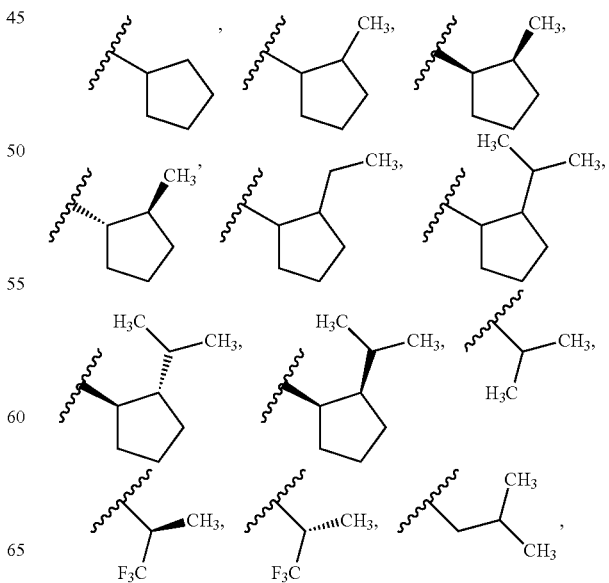

97
-continued
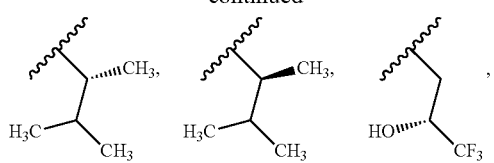
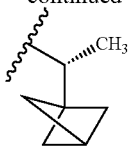
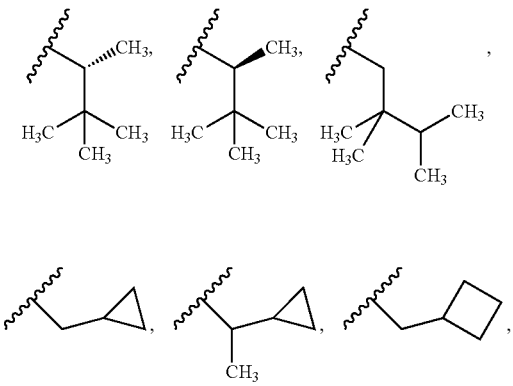
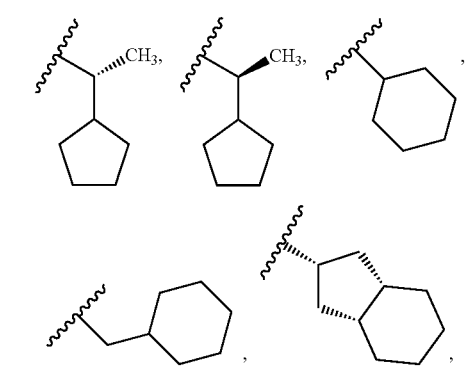
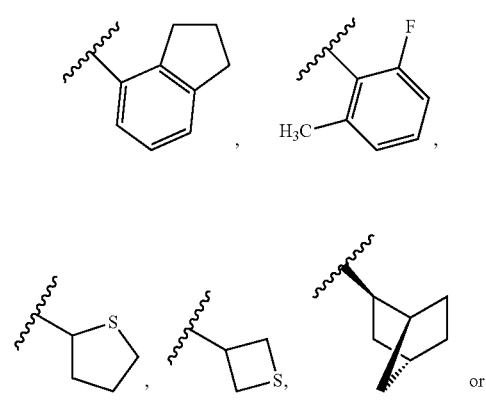
98
-continued
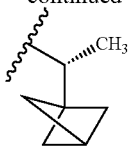
10. The compound of claim 1, selected from the group consisting of
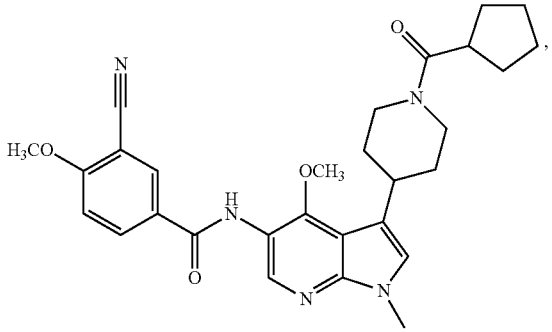
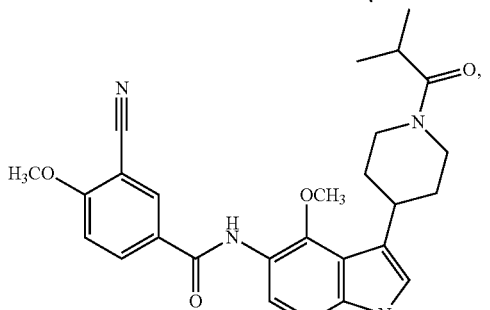
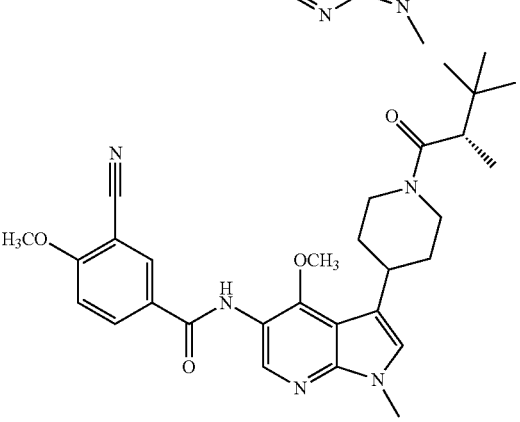
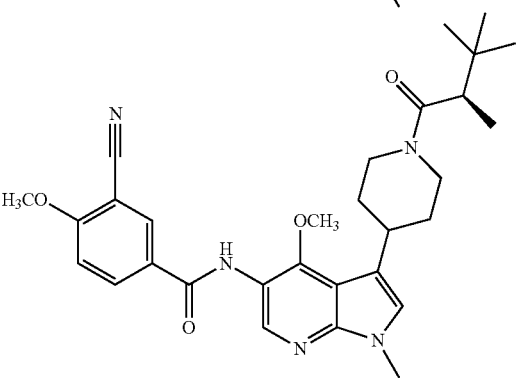

99
-continued
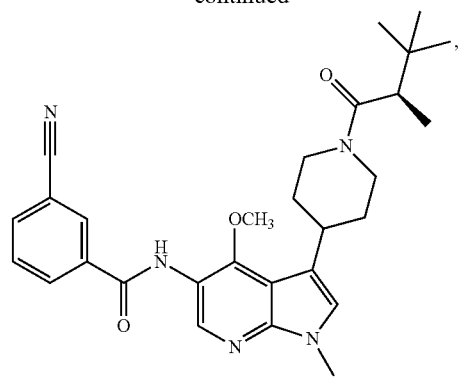
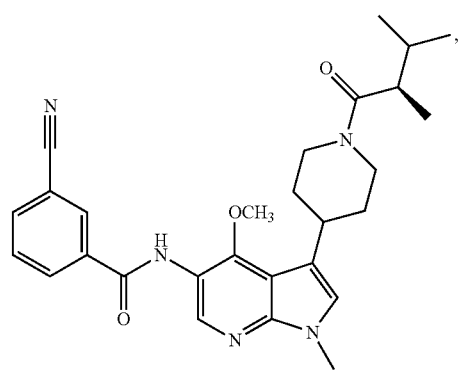
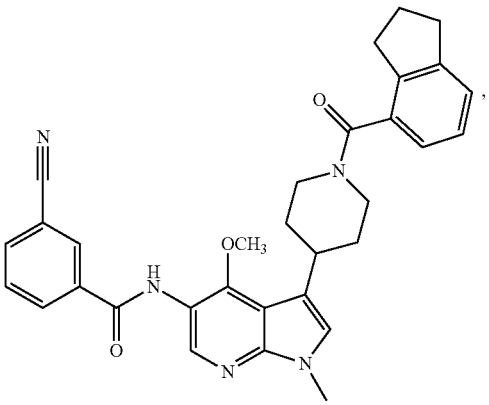
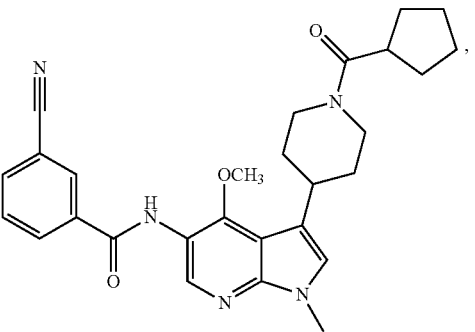
100
-continued
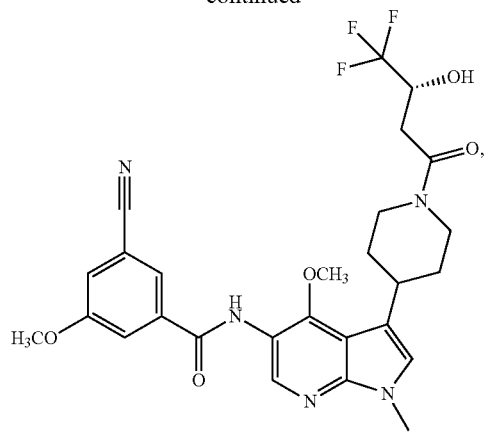
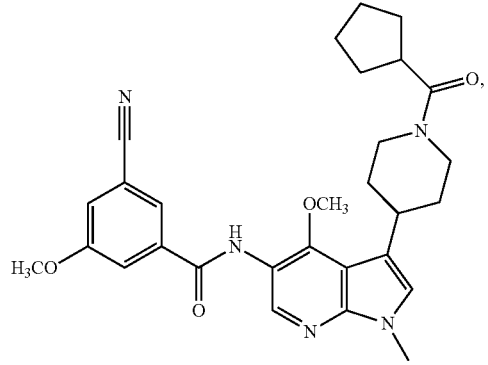
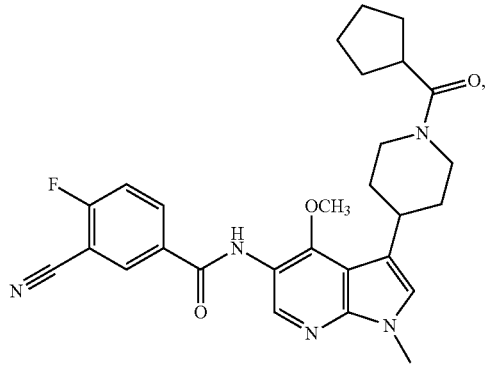
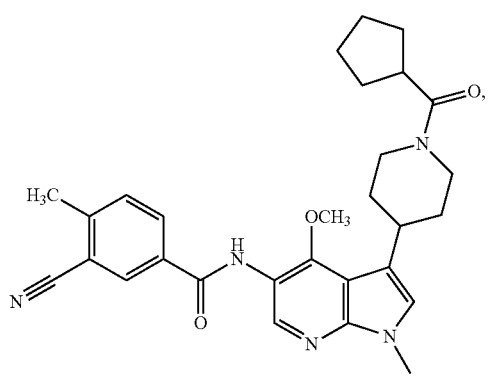

101
-continued
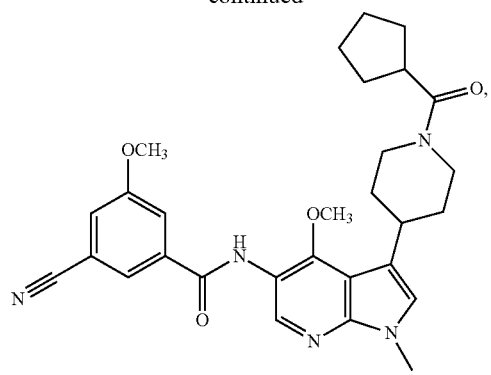
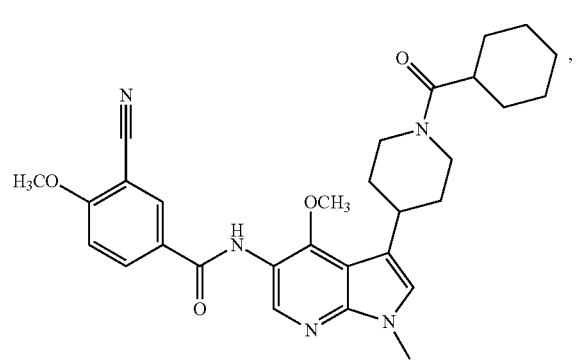
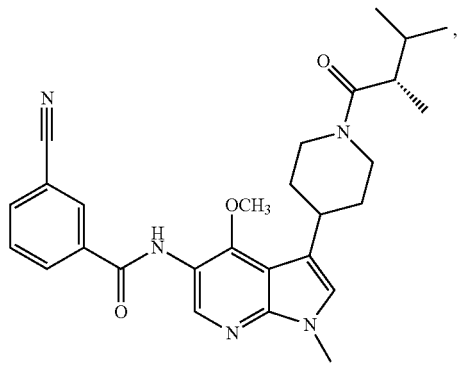
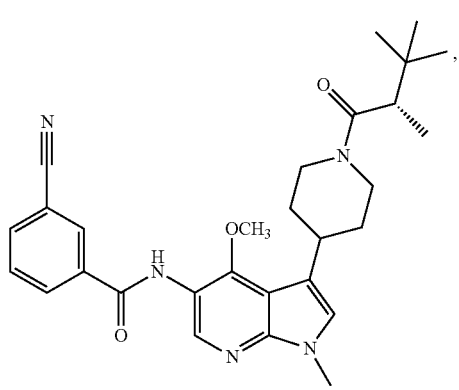
102
-continued
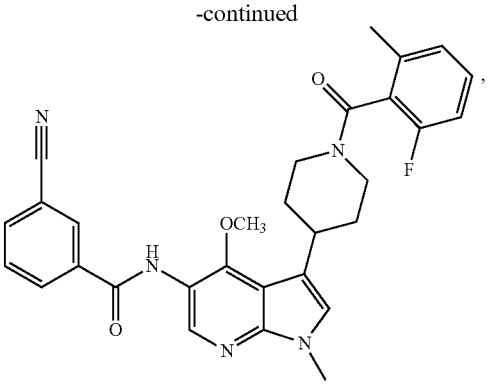
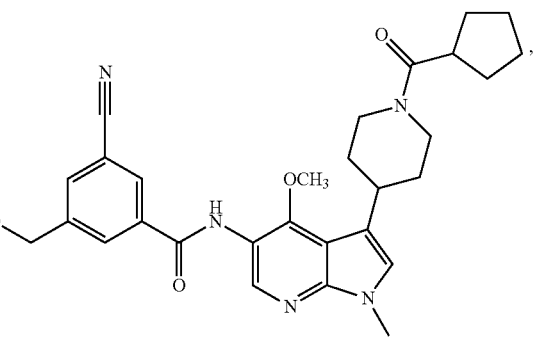
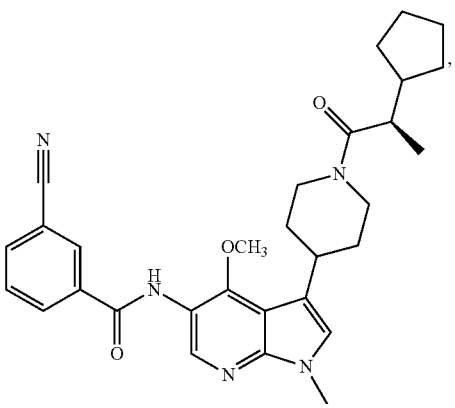
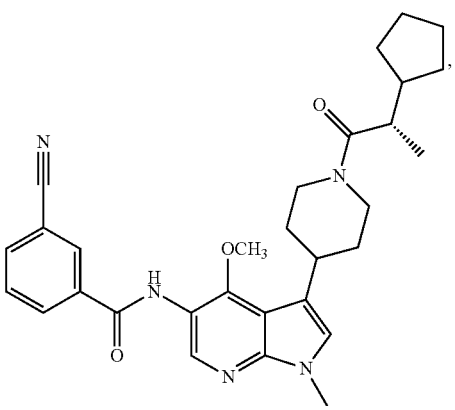

103
-continued
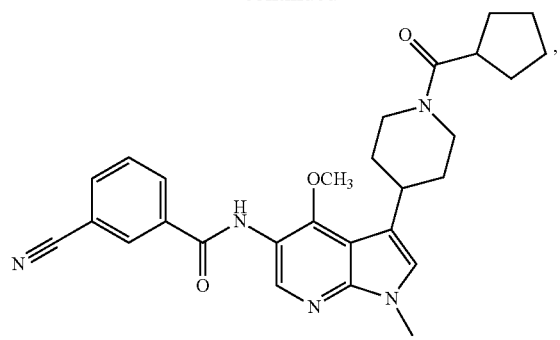
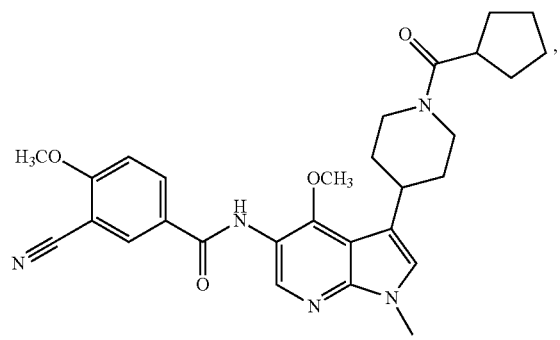
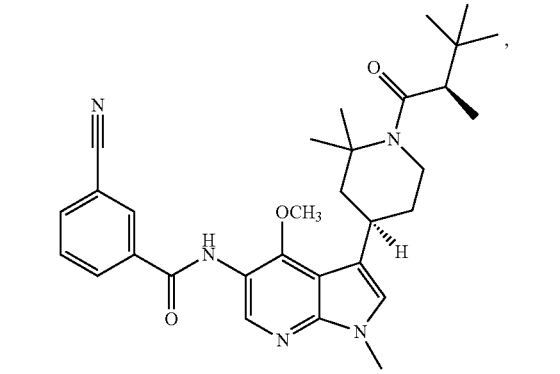
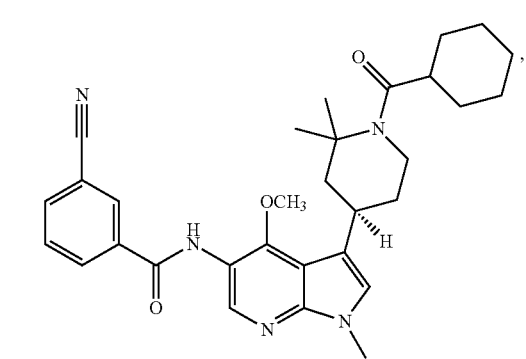
104
-continued
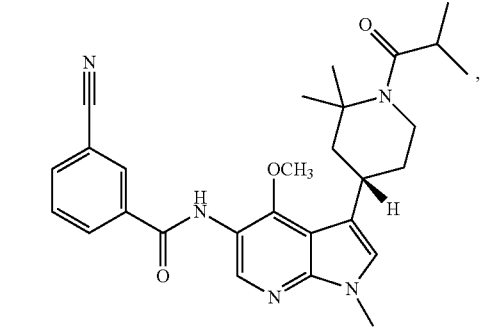
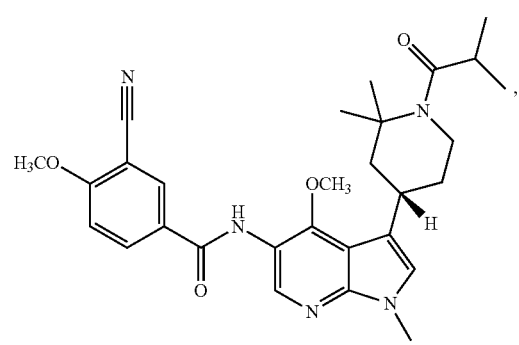
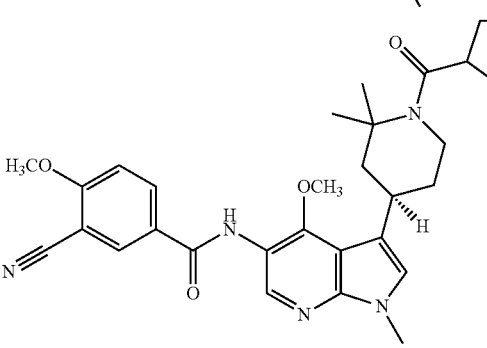
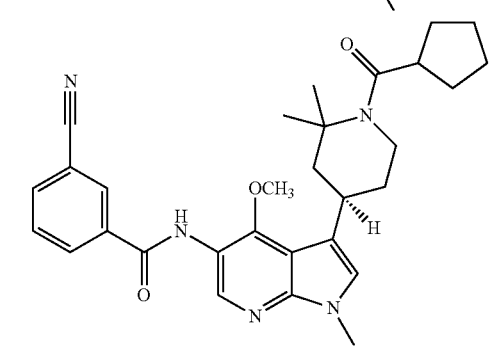
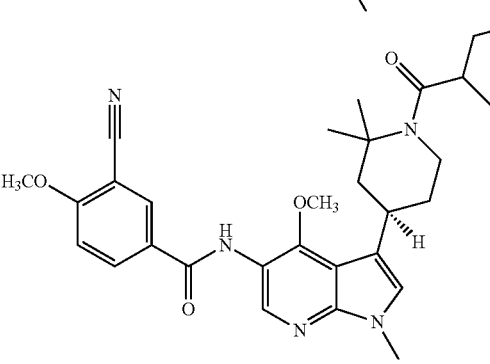

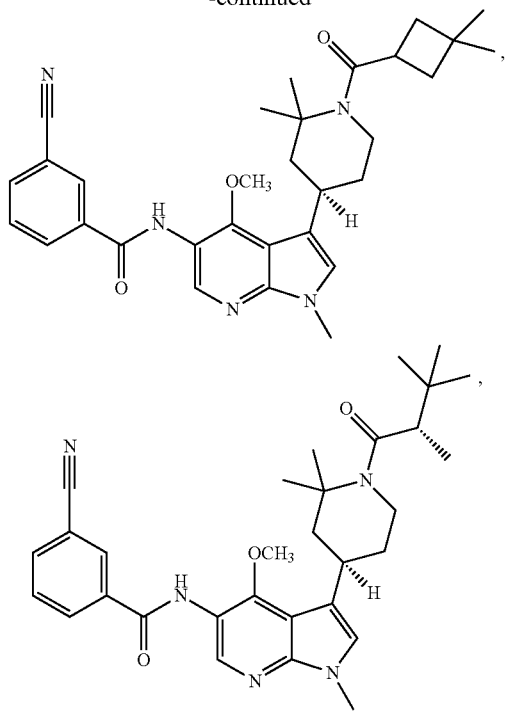
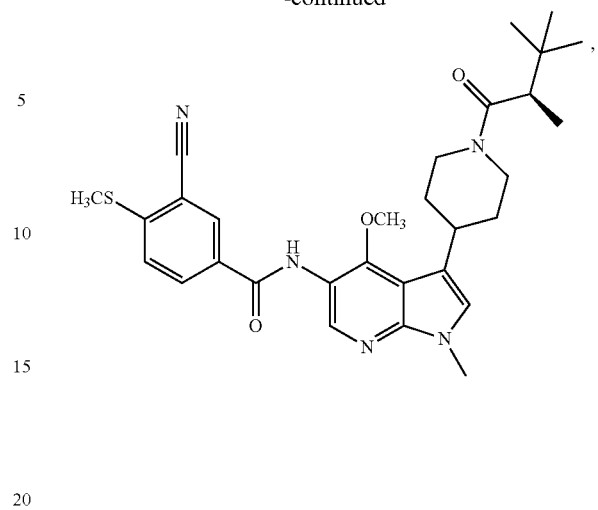
and pharmaceutically acceptable salts thereof.
11. A pharmaceutical composition comprising a compound according to claim 1, or a pharmaceutically acceptable salt thereof, admixed with a pharmaceutically acceptable carrier, excipient or diluent.
* * * * *